United States Patent [19]

Greengrass et al.

[11] Patent Number: 4,684,641

[45] Date of Patent: * Aug. 4, 1987

[54] 7-HYDROXYAMINOCEPHALOSPORIN ANTIBIOTICS

[75] Inventors: Colin W. Greengrass; David W. T. Hoople, both of Sandwich; Thomas T. Howarth, Margate, all of England

[73] Assignee: Pfizer Inc., New York, N.Y.

[*] Notice: The portion of the term of this patent subsequent to Aug. 4, 2004 has been disclaimed.

[21] Appl. No.: 749,915

[22] Filed: Jun. 27, 1985

[30] Foreign Application Priority Data

Jun. 28, 1984 [GB] United Kingdom ............... 8416498
Oct. 11, 1984 [GB] United Kingdom ............... 8425751

[51] Int. Cl.$^4$ ............... C07D 501/57; A61K 31/545
[52] U.S. Cl. .................................. 514/201; 540/219; 540/220; 540/221

[58] Field of Search ................ 544/21; 514/201; 540/221, 219

[56] References Cited

U.S. PATENT DOCUMENTS 4,297,488 10/1981 Christensen et al. ............... 544/21
4,609,652 9/1986 Milno ............................... 514/201

Primary Examiner—Nicholas S. Rizzo
Attorney, Agent, or Firm—Charles J. Knuth; Albert E. Frost; Robert K. Blackwood

[57] ABSTRACT

7α-Hydroxyamino-7β-[2-substituted-2-(acylamino)acetamido]-cephalosporin antibiotics, pharmaceutically-acceptable salts and in vivo hydrolyzable esters thereof, a method of treating susceptible infections therewith, and intermediates therefor.

20 Claims, No Drawings

7-HYDROXYAMINOCEPHALOSPORIN ANTIBIOTICS

BACKGROUND OF THE INVENTION

This invention relates to cephalosporin antibiotics, and in particular to cephalosporins having a 7α-hydroxyamino substituent.

U.S. Pat. No. 4,297,488, primarily directed to "7α-Methoxy Cephalosporins", broadly discloses a literal infinity of cephalosporin antibiotics of the formula

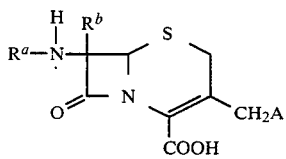

wherein $R^a$ represents any acyl group, A represents any organic radical or group, and $R^b$ represents any radical or group replacing hydrogen, and derivatives thereof such as esters, amides and salts. In extensive lists of possible groups which might correspond to $R^a$, $R^b$ and A in the above formula (still defining virtually infinite compounds) there is noted considerable overlap of possible groups A with present groups $R^2$ defined below. While for $R^a$ none of the present alpha-(acylamino)acyl groups.

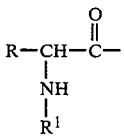

defined below, appear to be so listed, for $R^b$ one finds "hydroxiamino" listed among a list of some 100 different functional groups (which corresponds, through a wide variety of optional substituents, to an untold number of specific groups). No such compounds having $R^b$ as hydroxyamino are specifically disclosed or exemplified in this patent.

SUMMARY OF THE INVENTION

We have found a group of 7α-hydroxyamino cephalosporins which have unexpectedly good antibacterial properties, particularly against gram negative organisms, and including activity against beta-lactamase producing strains of bacteria.

Thus the present invention provides cephalosporin antibiotics of the formula

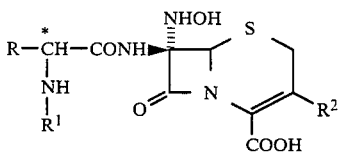

and their salts and esters. where R is phenyl, substituted phenyl, cyclohexenyl, cyclohexadienyl, $CH_3-CH(OH)-$, $CH_3-CH(OSO_3H)-$, $CH_3-CH(OCH_3)-$ or an optionally substituted aromatic 5- or 6-membered heterocyclic group containing 1, 2 or 3 heterotoms each independently selected from O, S and N; $R^2$ is —CH$_2$OCOCH$_3$, —CH$_2$OCONH$_2$, —Cl, —F, —OCH$_3$, —CH$_2$N$_3$, or a group of the formula:

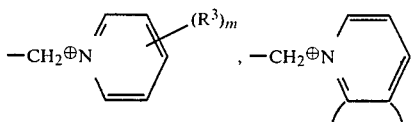

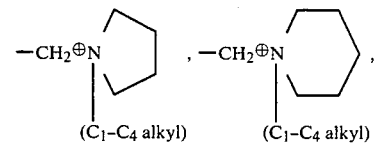

$-CH_2\overset{\oplus}{N}(C_1-C_4 \text{ alkyl})_3$, or $-CH_2S.Het$, where each $R^3$ is independently H or $C_1-C_4$ alkyl, m is 1 or 2, n is 3 or 4 and Het is an optionally substituted 5- or 6-membered heterocyclic group containing up to 4 heteroatoms selected from O, S and N, the heterocyclic group being optionally fused to an optionally substituted benzene ring or to a further 5- or 6-membered heterocyclic group containing up to 4 heterotoms selected from O, S and N; and $R^1$ is a group of the formula $-CONR^4R^5$ or $-COR^6$, where either (a) $R^4$ and $R^5$ are each independently H or $C_1-C_4$ alkyl, (b) $R^4$ is H or $C_1-C_4$ alkyl and $R^5$ is an optionally substituted 5 or 6 membered aromatic heterocyclic group containing 1 or 2 nitrogen atoms, or (c) $R^4$ and $R^5$ together with the nitrogen atom to which they are attached form an optionally substituted 5- or 6-membered heterocyclic group containing 1 or 2 N atoms, and $R^6$ is optionally substituted phenyl, or a substituted or unsubstituted optionally benzo-fused 5- or 6-membered heterocyclic group, or the group $-CH_2NH-C(=NH)(4-pyridyl)$.

When R is substituted phenyl, it is preferably phenyl substituted by 1, 2 or 3 substituents each independently selected from $-OH$, $C_1-C_4$ alkyl, $C_1-C_4$ alkoxy, $(C_1-C_4$ alkyl)CO.O—, halo, $CF_3$, $-NHSO_2 (C_1-C_4$ alkyl), $-NHCO(C_1-C_4$ alkyl), $-NH_2$, $-NH(C_1-C_4$ alkyl), $-N(C_1-C_4$ alkyl)$_2$, $-COOH$, $-CONH_2$, $-CONH(C_1-C_4$ alkyl), $-CON(C_1-C_4$ alkyl)$_2$, $-COO(C_1-C_4$ alkyl) and benzyloxycarbonyloxy.

Typical examples of R as substituted phenyl are 4-hydroxyphenyl, 3,4-dihydroxyphenyl, 3,4-diacetoxyphenyl, 3-chlorophenyl and 4-benzyloxycarbonyloxyphenyl.

When R is said optionally substituted aromatic 5- or 6-membered heterocyclic group, typical examples are 2- and 3-thienyl, 2-amino-4-thiazolyl, and 5-amino-1,2,4-thiadiazol-3-yl.

Preferably, R is phenyl, 3,4-dihydroxyphenyl, 4-hydroxyphenyl, 4-benzyloxycarbonyloxyphenyl, 2- or 3-thienyl, $CH_3CH(OH)-$, $CH_3CH(OCH_3)-$ or $CH_3CH(OSO_2OH)-$.

When $R^1$ is $-CONR^4R^5$, it is preferably a group of the formula:

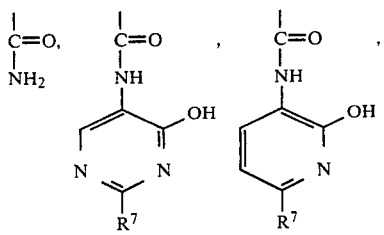

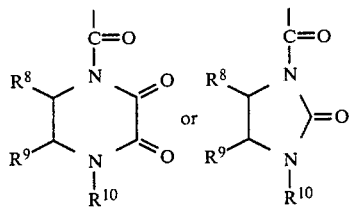

where $R^7$ is selected from (a) hydrogen, (b) cyclopropyl, (c) hydroxy, (d) $C_1$-$C_4$ alkoxy, (e) —$SO_2NH_2$, (f) —$NHR^{11}$ where $R^{11}$ is H, a $C_1$-$C_6$ alkyl group optionally containing a double or triple bond, or $C_3$-$C_6$ cycloalkyl, (g) —NH—alk—$R^{12}$ where alk is a straight or branched chain $C_1$-$C_4$ alkylene group and $R^{12}$ is —OH, —SH, —CN, —$CONH_2$, —$SO_2NH_2$, —$COCH_3$, —$NH_2$, —NH.($C_1$-$C_4$ alkyl), —N($C_1$-$C_4$ alkyl)$_2$, —NH.CHO, —NH.$COCH_3$, —$NHCONH_2$, $CH_3SO_2NH$—, —$OCH_3$, —$OC_2H_5$, —O.$COCH_3$, —S.$CH_3$, —SO.$CH_3$, —$SO_2CH_3$, —COOH, or —$COOCH_3$, (h)

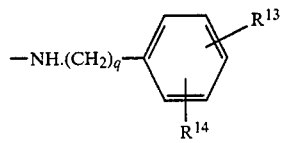

where q is 0 or 1 and $R^{13}$ and $R^{14}$ each independently represent H, halo, —OH, $C_1$-$C_4$ alkyl, $C_1$-$C_4$ alkoxy, —NHCO($C_1$-$C_4$ alkyl), —$NHCONH_2$, —NHCONH(-$C_1$-$C_4$ alkyl), —NHCON($C_1$-$C_4$ alkyl)$_2$, ($C_1$-$C_4$ alkyl)-$SO_2NH$—, —CO($C_1$-$C_4$ alkyl), —O.CO($C_1$-$C_4$ alkyl), —$CONH_2$, —CONH($C_1$-$C_4$ alkyl), —CON($C_1$-$C_4$ alkyl)$_2$, —$NO_2$, —CN, —S.$CH_3$, —$SOCH_3$, —$SO_2CH_3$, —$SO_2NH_2$, —$SO_2NH(C_1$-$C_4$ alkyl) or —$SO_2N(C_1$-$C_4$ alkyl)$_2$, and (i) —NH($CH_2$)$_q$.$R^{15}$ where q is 0 or 1 and $R^{15}$ is a substituted or unsubstituted 5- or 6-membered heterocycle containing 1 or 2 identical or different heteroatoms selected from O, S and N; $R^8$ and $R^9$ are each independently H or $C_1$-$C_4$ alkyl or together represent —($CH_2$)$_3$— or —($CH_2$)$_4$—; and $R^{10}$ is H, $C_1$-$C_8$ alkyl, —$SO_2(C_1$-$C_4$ alkyl), phenyl, benzyl, —N═CH.(2-furyl), —N═CH.(3,4-dihydroxyphenyl) or —($CH_2$)$_2$OH.

Preferred heterocyclic groups represented by $R^{15}$ are thienyl, furyl, pyrrolyl, oxazolyl, isoxazolyl, thiazolyl, isothiazolyl, imidazolyl, pyrazolyl, oxadiazolyl, thiadiazolyl, triazolyl, tetrazolyl, pyridyl, pyrazinyl, pyridazinyl or pyrimidinyl, all optionally substituted by, e.g., halo, $C_1$-$C_4$ alkyl, nitro, cyano, amino, —NHCO($C_1$-$C_4$ alkyl), —NH($C_1$-$C_4$ alkyl), —N($C_1$-$C_4$ alkyl)$_2$, —OH, $C_1$-$C_4$ alkoxy, $C_1$-$C_4$ alkylthio, $C_1$-$C_4$ alkylsulphinyl, —$NHSO_2(C_1$-$C_4$ alkyl), —$CONH_2$, —COO($C_1$-$C_4$ alkyl), —$SO_2NH_2$, —$SO_2NH.(C_1$-$C_4$ alkyl) or —$SO_2N(C_1$-$C_4$ alkyl)$_2$.

$R^6$ preferably either a phenyl group optionally substituted by 1 or 2 substituents each selected from —OH and $C_1$-$C_4$ alkyl, or is a 5- or 6-membered O or N containing heterocyclic group optionally benzo-fused and optionally substituted by —OH, $C_1$-$C_4$ alkyl, —$NH_2$ or oxo.

When $R^1$ is —$COR^6$, it is preferably a group of the formula:

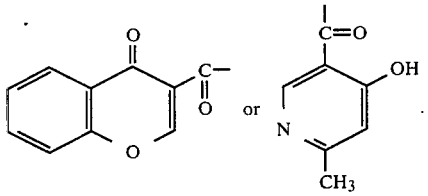

When $R^1$ is —$CONR^4R^5$, it is preferably a group of the formula:

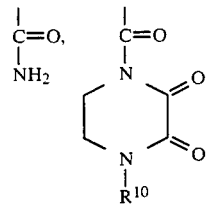

where $R^{10}$ is $C_1$-$C_8$ alkyl or benzyl,

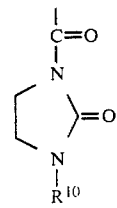

where $R^{10}$ is H, $C_1$-$C_6$ alkyl, —$SO_2(C_1$-$C_4$ alkyl) or —($CH_2$)$_2$OH.

When $R^2$ is —$CH_2SHet$, "Het" is preferably an optionally substituted triazolyl, tetrazolyl, thiazolyl, isothiazolyl, oxazolyl, oxadiazolyl, triazinyl, thiadiazolyl, benzoxazolyl, benzothiazolyl, or tetrazolopyridazinyl group. Preferred substituents are $C_1$-$C_4$ alkyl, $C_1$-$C_4$ alkoxy, halo, oxo or a group of the formula —($CH_2$)$_p R^{16}$ where p is 0, 1, 2 or 3 and $R^{16}$ is —COOH, —$OSO_2OH$, —$SO_2OH$, —$PO_3H_2$ or —OH, with the proviso that p is not zero when Het is tetrazolyl. With hydroxy and oxo substituents tautomerism may of course occur. "Halo" means F, Cl, Br or I.

The more preferred "Het" groups are attached to the adjacent S atom by a carbon atom of the heterocyclic ring and are (i) thiadiazolyl optionally substituted by $C_1$-$C_4$ alkyl or 2-hyroxyethyl (ii) tetrazolyl optionally substituted by $C_1$-$C_4$ alkyl, carboxymethyl, sulphomethyl, 2-hydroxyethyl or 2-(hydroxysulphonyloxy)ethyl (iii) thiazolyl optionally substituted by 1 or 2 substituents each selected from $C_1$-$C_4$ alkyl and carboxymethyl (iv) isothiazolyl optionally substituted by 1 or 2 substituents each selected from hydroxy and carboxy (v) benzothiazolyl or benzoxazolyl optionally substituted by hydroxy, $C_1$-$C_4$ alkoxy or halo (vi) tetrazolopyridazinyl optionally substituted by carboxy (vii) triazinyl optionally substituted by $C_1$-$C_4$ alkyl and/or by 1 or 2 oxo or hydroxy groups and (vii) triazolyl optionally substituted by carboxymethyl.

The preferred individual groups represented by "Het" are those given in the specific Examples.

Apart from —$CH_2SHet$, the preferred groups represented by $R^2$ are —$CH_2OCOCH_3$, —$CH_2OCONH_2$, —$CH_2N_3$ and a group of the formula:

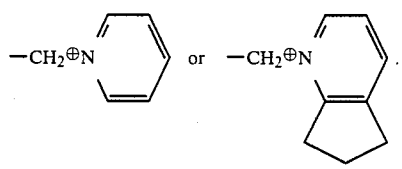

In the most preferred compounds of the formula (I), the substituents are as follows:
(a) R is unsubstituted phenyl or $CH_3CH(OH)$—
(b) $R^1$ is a group of the formula:

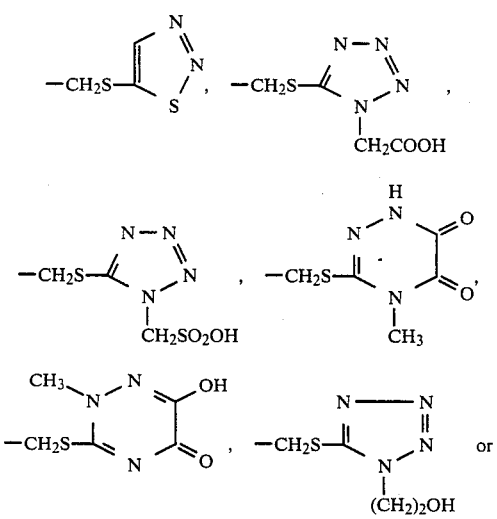

and
(c) $R^2$ is a group of the formula:

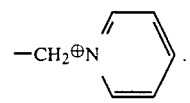

The preferred individual compounds of the formula (I) have the following substituents:
(a) R=$CH_3CH(OH)$—, $R^1$=

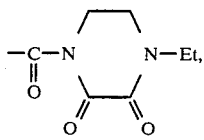

and $R^2$=

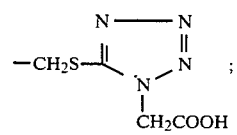

(b) R and $R^2$ is as in (a), and $R^1$=

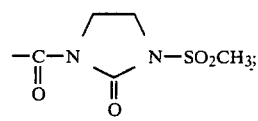

and
(c) R=Ph, $R^1$ is as in (a), and $R^2$=pyridiniummethyl.

The salts and esters (including in vivo hydrolysable esters) of the compounds of the formula (I) are well known to those skilled in the art. These salts include not only salts with —COOH, but also with —$OSO_2OH$ and —$SO_2OH$. The preferred salts are the sodium and potassium salts, and the triethylammonium salts. Some of the compounds may of course exist in zwitterionic form. The preferred in vivo hydrolysable esters are those of the formula:

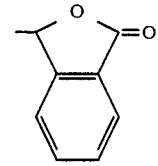

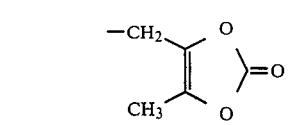

The preferred esters which are useful as intermediates are the t-butyl and benzhydryl esters.

In general, the DL- and D- form at the starred carbon atom of the compounds of the formula (I), or, when there is a side chain derived from threonine, the 2R, 3S-form, are preferred.

DETAILED DESCRIPTION OF THE INVENTION

The compounds of the formula (I) are preferably prepared by the replacement of —S.CH₃ in the 7α-position with —NHOH. This can be done on the 7α-methylthio-7β-acylamino compounds, i.e., after acylation is carried out to introduce the group RCH(NHR¹)CO—, or on compounds not having the acyl group present in the 7β-position. The desired 3-substituent can be introduced before or after the hydroxyamino substituent is present. In addition any O- or carboxy-protecting groups can be removed before or after the —NHOH group is in position.

Typically, the hydroxyamino substituent is introduced by reacting the appropriate methylthio compound with a mercuric salt, e.g. mercuric trifluoroacetate, mercuric chloride or mercuric acetate, and preferably with mercuric acetate, at low temperature, e.g. −50° C., in a suitable organic solvent, eg dimethylformamide (DMF). Hydroxylamine (preferably generated from hydroxylamine hydrochloride/triethylamine), again typically in DMF, is added, and the solution is slowly warmed to from −20° to +20° C. An acid addition salt of hydroxylamine, e.g. the hydrochloride, can be used in place of hydroxylamine itself. The 7β-hydroxyamino product can then be isolated conventionally. $C_2$-$C_4$alkylthio, phenylthio or benzylthio derivatives can be used in place of the methylthio starting materials. Similarly metal salts (e.g. acetates) such as silver, thallium, lead or copper salts can be used in place of mercuric salts.

The 7α-methylthio compounds are either known compounds or can be prepared conventionally.

Typical routes to the compounds of the formula (I) are illustrated schematically as follows:

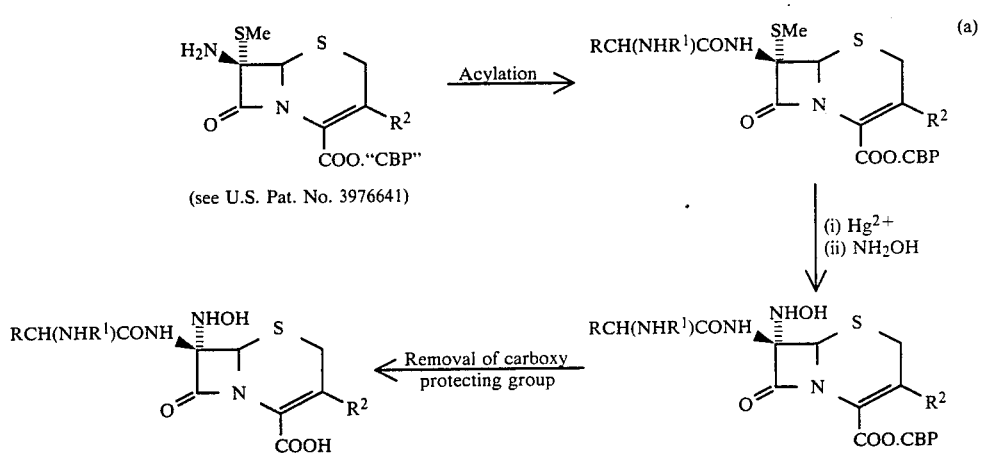

(see U.S. Pat. No. 3976641)

"CBP" = a carboxy protecting group.

Modifications at the 3-position (e.g. —CH₂OAc to —CH₂SHet) can if desired be carried out before or after introduction of the hydroxyamino substituent.

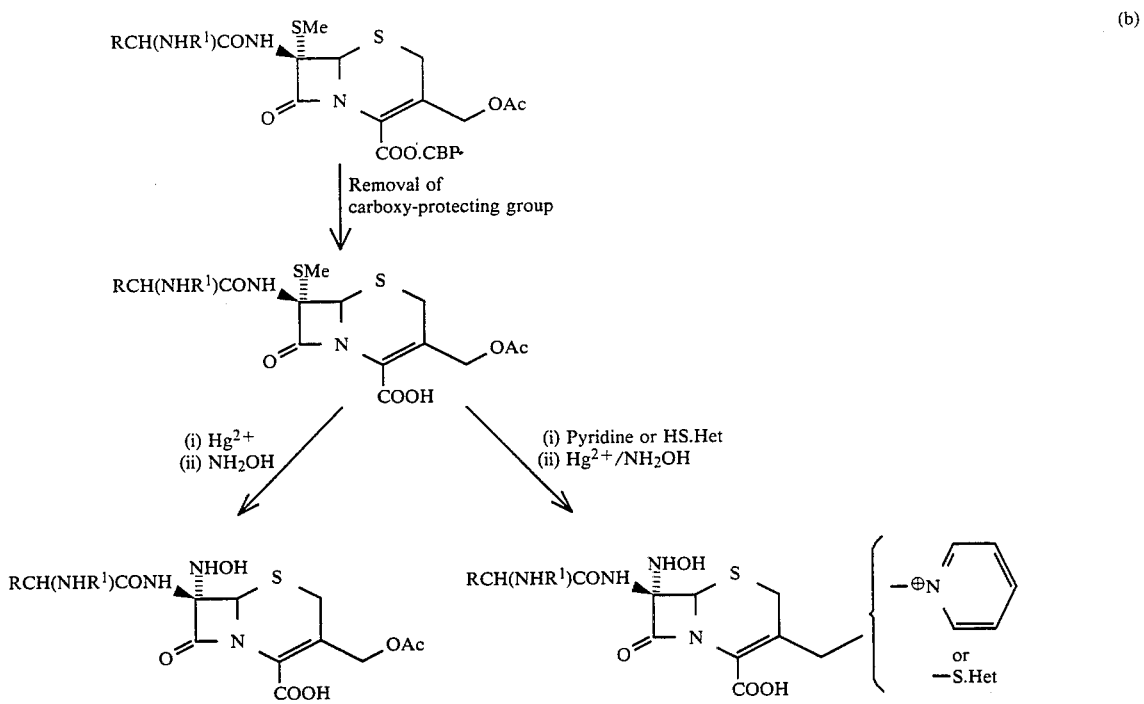

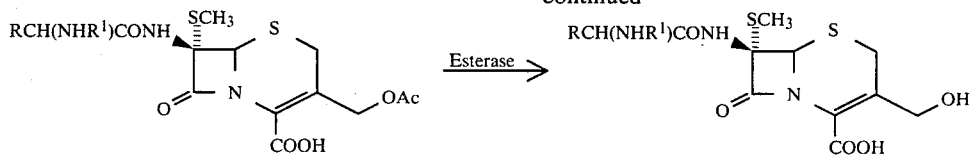

(c)

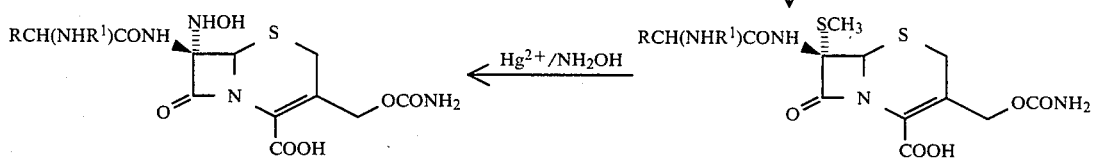

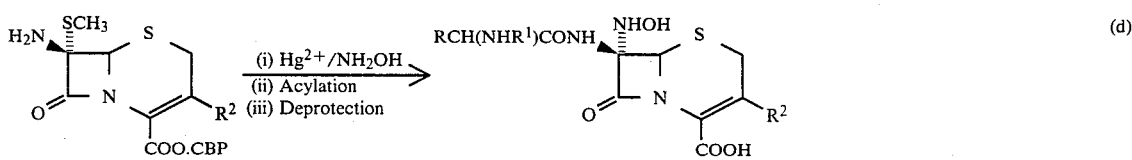

and (d)

(see eg GB 1526793).

Compounds in which $R^2$ is $-CH_2N_3$ can be prepared by conversion of $-CH_2OCOCH_3$ into $-CH_2N_3$ using an alkali metal azide, e.g. sodium azide.

Any hydroxy-protecting groups, if present, can again be removed before or after insertion of the hydroxyamino group.

Apart from the insertion of the hydroxyamino group, all the above steps are conventional (see eg British patent application publication No. 2107307A or U.S. Pat. No. 4,297,488).

Acylation is typically carried out using an acid chloride or bromide of the acid $RCH(NHR^1)COOH$ or an O-protected derivative thereof. Alternatives are of course activated esters, mixed anhydrides. The reaction is typically carried out at low temperature ($-10°$ to $0°$ C.) in a suitable organic solvent, eg dichloromethane. When an acid halide is used, the presence of an acid binding agent such as pyridine or triethylamine is preferred.

Many conventional carboxy protecting groups (CBP's) can be used, eg t-butyl, benzhydryl, benzyl, p-methoxybenzyl and p-nitrobenzyl. These can all be removed by conventional means. The preferred protecting groups are t-butyl, which is typically removed with trifluoroacetic acid, and benzhydryl, which is typically removed with anisole/AlCl$_3$ or trifluoroacetic acid.

Modifications at position 3 of the cephalosporin ring are carried out by conventional methods, e.g.:

(a)

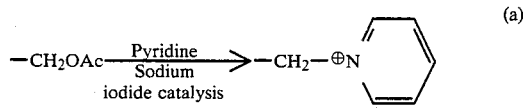

(Similarly for all compounds in which $R^2$ contains a quaternary group.)

(b)

$$\left. \begin{array}{l} CH_2OAc \\ CH_2I \\ CH_2Br \end{array} \right\} \xrightarrow[\text{(or salt [e.g. an alkali metal salt] thereof)}]{Het\ SH} -CH_2S.Het$$

(Other suitable leaving groups than $-OAc$, I or Br can be used.)

The $C_3$ acetoxymethyl group can be reacted with the thiol in the presence of a Lewis acid such as boron trifluoride, if desired (see J5 5020 724).

It should be mentioned that derivatives of hydroxylamine protected on oxygen can be used in place of hydroxylamine in the formation of the $-NHOH$ group, such derivatives including $H_2N-OSiMe_3$, $H_2N-OSiMe_2tBu$, $H_2N-OSiPh_2tBu$, $H_2N-OSi(C_1-C_4alkyl)_3$, $H_2N-O.benzyl$, $H_2N-0.COO.benzyl$, $H_2N-O.COOtBu$, $H_2N-O.COOCH_2CCl_3$, $H_2N-O.COOCH_2CH=CH_2$, $H_2N-OCH_2CH=CH_2$, $H_2N-O.COOCH_2-\bigcirc-NO_2$, $H_2N-O.COOCH_2-\bigcirc-OCH_3$, or $H_2N-O.COOCH_2CH_2Si(CH_3)_3$.

The O-protecting groups can be removed conventionally.

The same O-protecting groups can be used, if desired, to protect the hydroxy groups of $CH_3CH(OH)-$ (see R) and of any hydroxy or hydroxyalkyl substituents. The preferred O-protecting groups are t-butyldiphenylsilyl and t-butyldimethylsily, removed with aqueous hydrofluoric acid.

The salts and in vivo hydrolysable esters can be prepared conventionally.

An alternative method of introducing hydroxyamino can be represented as follows:

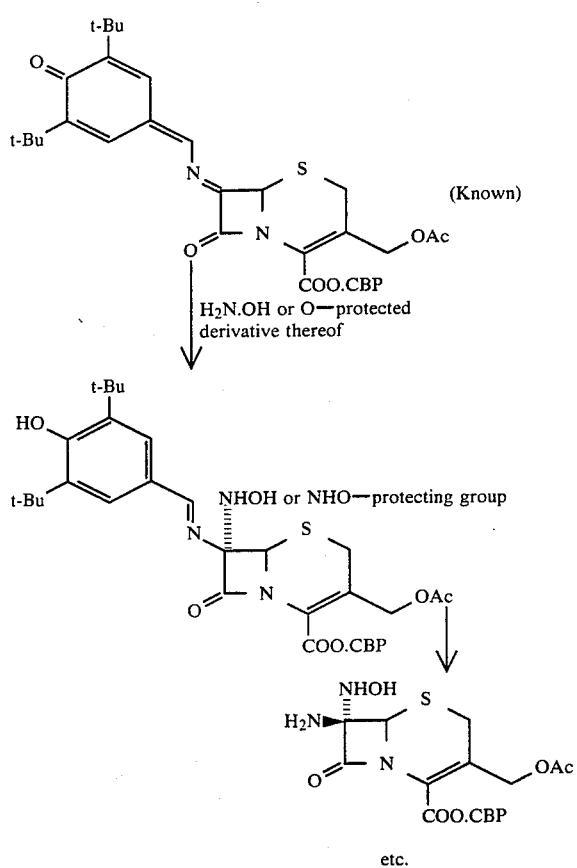

etc.

For administration to man in the curative or prophylactic treatment of bacterial infections, parenteral dosages of the compounds will typically be in the range of from 100 mg. to 8 g. daily for an average adult patient (70 kg), and, most commonly, from 1 g to 4 g daily. Thus for a typical adult patient, individual parenteral formulations will contain from 0.5 to 2 g. of active compound, in a suitable pharmaceutically acceptable vehicle. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered parenterally in admixture with a pharmaceutical diluent selected with regard to the intended route of administration and standard pharmaceutical practice. They can be injected intravenously, intramuscularly or subcutaneously. They are best used in the form of a sterile aqueous solution which may contain other substances, for example, enough salts or glucose to make the solution isotonic with blood, and the solution may also contain an anaesthetic such as lignocaine.

Thus in a further aspect the invention provides a pharmaceutical composition comprising a compound of the formula (I), or a pharmaceutically acceptable salt thereof, or in vivo hydrolysable ester thereof, together with a pharmaceutically acceptable diluent or carrier.

The compounds may also be administered in combination with other antibiotics and/or $\beta$-lactamase inhibitors such as sulbactam.

The invention also provides a compound of the formula (I), or a pharmaceutically acceptable salt or in vivo hydrolysable ester thereof, for use in medicine, in particular for use as an antibiotic.

The invention also provides a method of treating a bacterial infection in a human patient, which comprises administering to the patient an effective amount of a compound of the formula (I) or pharmaceutically acceptable salt or in vivo hydrolysable ester thereof.

The compounds of the formula (I) and their pharmaceutically acceptable salts and in vivo hydrolysable esters are antibiotics which have unexpectedly high activity. They are particularly active against gram negative organisms, such as *E. coli, Klebsiella pneumoniae, Proteus mirabilis, Proteus vulgaris, Proteus morganii, Providentia stuartii, Providentia rettgeri, Haemophilus influenzae* and *Bacteriodes fragilis*, assessed by usual methods.

The following Examples, in which all temperatures are in °C., illustrate the invention:

EXAMPLE 1

7$\beta$-[D-2-(4-Ethyl-2,3-dioxopiperazin-1-ylcarbonylamino)-2-phenylacetamido]-7$\alpha$-hydroxyamino-3-[(1,2,3-thiadiazol-5-yl)thiomethyl]ceph-3-em-4-carboxylic acid (a) t-Butyl 7$\beta$-amino-3-[(1,2,3-thiadiazol-5-yl)thiomethyl]ceph-3-em-4-carboxylate 7$\beta$-Amino-3-[1,2,3-thiadiazol-5-ylthio)methyl]ceph-3-em-4-carboxylic acid (2.0 g) was suspended in dry dichloroemthane (50 ml) and treated with O-t-butyl-N,N'-diisopropylisourea (4.0 g) in dichloromethane (20 ml) over 5 minutes. After 6 hours the solution was filtered and the filtrate was washed with saturated sodium bicarbonate (50 ml). The organic phase was dried (MgSO$_4$) and evaporated in vacuo to give the title compound as a brown foam (1.6 g).

I.R. (CH$_2$Cl$_2$) 1785 cm$^{-1}$.

N.M.R. (CDCl$_3$) $\delta$ = 1.53 (s, 9H); 3.45 and 3.68 (ABq, J = 16, 2H); 4.08 and 4.18 (ABq, J = 12, 2H); 4.95 (s, 1H); 5.32 (s, 1H); 8.52 (s, 1H).

(b) t-Butyl 7$\beta$-phenylimino-3-[(1,2,3-thiadiazol-5-yl)thiomethyl]ceph-3-em-4-carboxylate t-Butyl7$\beta$-amino-3-[(1,2,3-thiadizol-5-yl)thiomethyl]-ceph-3-em-4-carboxylate (1.6 g) was dissolved in methanol (50 ml) and treated with benzaldehyde (0.44 g) overnight. The solvent was evaporated in vacuo and the residue was dissolved in ethyl acetate. This was washed with aqueous sodium metabisulphite, water, dried (MgSO$_4$) and evaporated to a brown foam (1.7 g).

I.R. (CH$_2$Cl$_2$) 1780 cm$^{-1}$.

N.M.R. (CDCl$_3$) $\delta$ = 1.53 (s, 9H); 3.40 and 3.68 (ABq, J = 16, 2H); 4.05 and 4.22 (ABq, J = 13, 2H); 5.16 (d, J = 4, 1H); 5.44 (d, J = 4, 1H); 7.4–7.8 (m, 5H); 8.54 (s, 1H); 8.63 (s, 1H).

(c) t-Butyl 7$\beta$-amino-7$\alpha$-methylthio-3-[1,2,3-thiadiazol-5-yl)thiomethyl]ceph-3-em-4-carboxylate t-Butyl7$\beta$-phenylimino-3-[(1,2,3-thiadiazol-5-yl)thiomethyl]ceph-3-em-4-carboxylate (1.7 g) was dissolved in dry tetrahydrofuran (50 ml) and cooled to −70° C. under nitrogen. A solution of potassium t-butoxide (400 mg) in tetrahydrofuran (20 ml) was added in one portion and stirred for 5 minutes. Methyl thiomethane sulphonate [CH$_3$SO$_2$SCH$_3$] (435 $\mu$l) was added and the mixture was warmed to 0° C. during 3 hours. A pH 6.5 buffer solution (150 ml) was added and the whole was extracted with ethyl acetate (3×50 ml). The combined organic phases were dried (MgSO$_4$) and evaporated in vacuo to give a brown oil which was chromatographed on silica gel (dichloromethane:ethyl acetate 3:1) to give the 7α-methylthioimine (1.2 g). This was dissolved in ether (50 ml) and treated with a solution of p-toluenesulphonic acid in the minimum volume of acetone. After 30 minutes at room temperature and 30 minutes at 0° C., the p-toluenesulphonic acid salt of the title compound was filtered off. This salt was partitioned between saturated sodium bicarbonate and ethyl acetate and the organic phase was washed with water, dried (MgSO$_4$) and evaporated in vacuo to give the title compound.

I.R. (CH$_2$Cl$_2$) 1780 cm$^{-1}$.

N.M.R. (DMSO d$_6$) δ=1.40 (s, 9H); 2.12 (s, 3H); 2.95 (s, 2H); 3.5 and 3.72 (ABq, J=15, 2H); 4.18 (ABq, J=6, 2H); 5.01 (s, 1H); 8.9 (s, 1H).

(d) t-Butyl 7β-[D-2-(4-ethyl-2,3-dioxopiperazin-lylcarbonylamino)-2-phenylacetamido]-7α-methylthio-3-[(1,2,3-thiadiazol-5-yl)thiomethyl]ceph-3-em-4-carboxylate t-Butyl 7β-amino-7α-methylthio-3-[(1,2,3-thiadiazol-5-yl)thiomethyl]ceph-3-em-4-carboxylate (0.20 g) in dichloromethane (5 ml) was cooled to −20° C. and treated dropwise over 1 minute with a solution of D-2-[4-ethyl-2,3-dioxopiperazin-1-ylcarbonylamino]-2-phenyl-acetyl chloride (0.17 g) in dichloromethane (2 ml). Pyridine (40 µl) was added during 0.5 minutes, the solution was allowed to warm to 0° over 2 hours, washed with 1% hydrochloric acid (20 ml), saturated sodium bicarbonate (20 ml) and dried (MgSO$_4$). The solvent was evaporated in vacuo and the residue was chromatographed (silica gel/dichlormethane:ethyl acetate 7:3) to yield the title compound, (0.23 g).

I.R. (CH$_2$Cl$_2$) 1785 cm$^{-1}$.

N.M.R. (CDCl$_3$) δ=1.22 (t, J=7, 3H); 1.48 (s, 9H); 2.25 (s, 3H); 3.54–3.62 (m, 4H); 3.95–4.31 (m, 6H); 4.89 (s, 1H); 5.60 (d, J=6, 1H); 7.38–7.51 (m, 5H); 8.51 (s, 1H); 10.00 (d, J=6, 1H).

(e) t-Butyl 7β-[D-2-(4-ethyl-2,3-dioxopiperazin-1-ylcarbonylamino)-2-phenylacetamido]-7α-hydroxyamino-3-[(1,2,3-thiadiazol-5-yl)thiomethyl]ceph-3-em-4-carboxylate t-Butyl 7β-[D-2-(4-ethyl-2,3-dioxopiperazin-1-ylcarbonylamino)-2-phenylacetamido]-7α-methylthio-3-[(1,2,3-thiadiazol-5-yl)thiomethyl]ceph-3-em-4-carboxylate (0.23 g) in dimethylformamide (DMF) (3 ml) was cooled to −50° under nitrogen then treated successively with a solution of mercuric acetate (0.105 g) in dimethylformamide (1 ml) and hydroxylamine hydrochloride (0.03 g) in dimethylformamide (1 ml). The mixture was warmed to 0° C. over 1 hour and added to ethyl acetate (50 ml). The solution was washed with water (5×30 ml) dried and evaporated in vacuo. the residue was purified by chromatography (silica gel, dichloromethane-ethyl acetate gradient) to give the title compound, (0.20 g).

I.R. (CH$_2$Cl$_2$) 1785 cm$^{-1}$.

N.M.R. (CDCl$_3$) δ=1.15 (t, J=6, 3H); 1.5 (s, 9H); 2.95 and 3.08 (ABq, J=15, 2H); 3.59 (m, 4H); 3.92–4.2 (m, 4H); 5.23 (s, 1H); 5.6 (d, J=6, 1H); 7.3–7.7 (m, 5H); 8.5 (s, 1H); 10.08 (d, J=6, 1H).

(f) 7β-[D-2-(4-ethyl-2,3-dioxopiperazin-1-ylcarbonylamino)-2-phenylacetamido]-7α-hydroxyamino-3-[(1,2,3-thiadiazol-5-yl)thiomethyl]ceph-3-em-4-carboxylic acid t-Butyl 7β-[D-2-(4-ethyl-2,3-dioxopiperazin-1-ylcarbonylamino)-2-phenylacetamido]-7α-hydroxyamino-3-[1,2,3-thiadiazol-5-yl)thiomethyl]ceph-3-em-4-carboxylate (0.20 g) was dissolved in trifluoroacetic acid (3 ml) and allowed to react for 10 minutes before evaporation in vacuo. The residue was taken up in ethyl acetate (20 ml) and extracted with saturated aqueous sodium bicarbonate solution (2×20 ml). The combined aqueous extracts were back-washed with ethyl acetate and acidified with hydrochloric acid to pH 2. The acidified solution was extracted with ethyl acetate (3×30 ml), the combined organic phases washed, dried (MgSO$_4$) and evaporated in vacuo to give the title compound, (0.06 g).

I.R. (KBr) 1780 cm$^{-1}$.

N.M.R. (DMSO d$_6$-D$_2$O) δ=1.08 (t, J=6, 3H); 3.2–3.6 (m, 6H); 3.8–4.0 (m, 2H); 4.10 and 4.23 (ABq, J=13, 2H); 5.05 (s, 1H); 5.65 (d, J=7, 1H); 7.2–7.5 (m, 5H); 8.85 (s, 1H); 9.58 (s, 1H); 9.90 (d, J=7, 1H).

EXAMPLE 2

7β-[D-2-(4-Ethyl-2,3-dioxopiperazin-1-ylcarbonylamino)-2-phenylacetamido]-7α-hydroxyaminocephalosporanic acid (a) t-Butyl 7β-[D-2-(4-ethyl-2,3-dioxopiperazin-1-ylcarbonylamino)-2-phenylacetamido]-7α-methylthiocephalosporanate t-Butyl 7β-amino-7α-methylthiocephalosporanate (1.86 g) in dichloromethane (25 ml) was cooled to −10° C. and treated dropwise during 1 minute with a solution of D-2-[4-ethyl-2,3-dioxopiperazin-1-ylcarbonylamino]-2-phenylacetyl chloride (1.86 g) in dichloromethane (5 ml). Pyridine (440 µl) was added during 1 minute and the solution was stirred at −10° for 30 minutes, then washed with 1% hydrochloric acid (50 ml), saturated sodium bicarbonate (50 ml) and dried (Na$_2$SO$_4$). The solvent was removed in vacuo and the residue was chromatographed (silica gel, dichloromethane:ethyl acetate 1:1) to give the title compound (3.1 g).

I.R. (KBr) 1790 cm$^{-1}$.

N.M.R. (CDCl$_3$) δ=1.16 (t, J=7, 3H); 1.48 (s, 9H); 2.02 (s, 3H); 2.22 (s, 3H); 2.85–3.75 (m, 6H); 3.8–4.2 (m, 2H); 4.67 and 5.03 (ABq, J=13, 2H); 4.84 (s, 1H); 5.72 (d, J=7, 1H); 7.1–7.6 (m, 5H); 7.66 (Brs, NH); 9.95 (d, J=7, NH).

(b) t-Butyl 7β-[D-2-(4-ethyl-2,3-dioxopiperazin-1-ylcarbonylamino)-2-phenylacetamido]-7α-hydroxyaminocephalosporanate t-Butyl 7β-[D-2-(4-ethyl-2,3-dioxopiperazin-1-ylcarbonylamino)-2-phenylacetamido]-7α-methylthiocephalosporanate (1.35 g) in dimethylformamide (8 ml) was cooled to −50° C. under nitrogen then treated successively with a solution of mercuric acetate (0.64 g) in dimethylformamide (3 ml) followed by a solution of hydroxylamine in dimethylformamide, prepared from hydroxylamine hydrochloride (0.14 g), triethylamine (278 µl) and dimethylformamide (4 ml). The mixture was warmed to −20° C. during 30 minutes and added to ethyl acetate (100 ml). This solution was washed with water (3×50 ml), dried and evaporated in vacuo. The crude product produced (1.05 g) was purified by chromatography (silica gel, dichloromethane-ethylacetate gradient) to give the title compound (950 mg), m.p. 147° (dec).

IR (CH$_2$Cl$_2$) 1785 cm$^{-1}$.

N.M.R. (CDCl$_3$) δ=1.20 (t, J=7, 3H); 1.53 (s, 9H); 2.08 (s, 3H); 2.95 and 3.29 (ABq, J=17, 2H); 3.4–3.65

(m, 4H); 3.85-4.13 (m, 2H); 4.78 and 4.95 (ABq, J=13, 2H); 5.23 (s, 1H); 5.52 (d, J=6, 1H); 6.58 (d, J=3, 1H, exch)); 6.86 (brs, 1H, exch); 7.3-7.65 (m, 5H); 8.63 (brs, NH), 10.0 (d, J=6, NH).

Found: C, 52.37; H, 5.54; N, 12.04%. $C_{29}H_{36}N_6O_{10}S$ Requires: C, 52.72; H, 5.45; N, 12.72%.

(c) 7β-[D-2-(4-Ethyl-2,3-dioxopiperazin-1-ylcarbonylamino-2-phenylacetamido]-7α-hydroxyaminocephalosporanic acid t-Butyl 7β-[D-2-(4-ethyl-2,3-dioxopiperazin-1-ylcarbonylamino)-2-phenylacetamido]-7α-hydroxyaminocephalosporanate (660 mg) was dissolved in trifluoroacetic acid (3 ml) and allowed to react for 5 minutes before evaporation in vacuo T.l.c. monitoring indicated incomplete reaction and the reaction was repeated with fresh trifluoroacetic acid (3 ml). The residue was taken up in dichloromethane:carbon tetrachloride 1:1 and rotary evaporated. This evaporation was repeated and finally the product was triturated with dry diethyl ether to give the title compound as a nearly white solid (485 mg).

IR (KBr) 1780 cm$^{-1}$.

N.M.R. (DMSO d$_6$) δ=1.1 (t, 3H, J=6); 2.1 (s, 3H); 3.1-3.65 (m, 6H); 3.85-3.98 (m, 2H); 4.62 and 4.90 (ABq, J=12, 2H); 5.04 (s, 1H); 5.72 (d, J=7, 1H); 6.52 (brs, 1H); 7.25-7.55 (m, 5H); 8.20 (s, 1H); 9.56 (s, NH); 9.84 (COOH); 9.88 (d, J=7, NH).

EXAMPLE 3

7β-[DL-2-(4-ethyl-2,3-dioxopiperazin-1-ylcarbonylamino)-2-(2-thienylacetamido]-7α-hydroxyamino-3-[(1,2,3-thiadiazol-5-yl)thiomethyl]ceph-3-em-4-carboxylic acid (a) t-Butyl 7β-[DL-2-(4-ethyl-2,3-dioxopiperazin-1-ylcarbonylamino)-2-(2-thienyl)acetamido]-7α-methylthio-3-[(1,2,3-thiadiazol-5-yl)thiomethyl]ceph-3-em-4-carboxylate The 7α-methylthiocephem (from Example 1(c) (0.30 g) was converted into the title compound (0.37 g) by the method of example 1(d) using the appropriate acid chloride.

I.R. (CH$_2$Cl$_2$) 1785 cm$^{-1}$.

N.M.R. (CDCl$_3$) δ=1.25 (t, J=6, 3H); 1.50 (s, 9H); 2.25+2.33 (2s, 3H); 3.5-3.7 (m, 6H); 4.0-4.3 (m, 4H); 4.9+4.93 (2s, 1H); 5.9 (d, 1H, J=6); 7.0-7.40 (m, 3H); 8.55 (s, 1H); 9.9 (d, J=6, 1H).

(b) t-Butyl 7β-[DL-2-(4-ethyl-2,3-dioxopiperazin-1-ylcarbonylamino)-2-(2-thienyl)acetamido]-7α-hydroxyamino-3-[(1,2,3-thiadiazol-5-yl)thiomethyl]ceph-3-em-4-carboxylate t-Butyl 7β-[DL-2-(4-ethyl-2,3-dioxopiperazin-1-ylcarbonylamino)-2-(2-thienyl)acetamido]-7α-methylthio-3-[(1,2,3-thiadiazol-5-yl)thiomethyl]ceph-3-em-4-carboxylate (0.37 g) was converted to the title compound by the method of Example 1(e).

I.R. (CH$_2$Cl$_2$) 1780 cm$^{-1}$.

N.M.R. (CDCl$_3$) δ=1.24 (t, J=6, 3H); 1.42 (s, 9H); 3.2-3.8 (m, 6H); 3.9-4.4 (m, 4H); 5.26+5.30 (2s, 1H); 5.61 (d, J=6, 1H); 6.9-7.3 (m, 3H); 8.50 (s, 1H); 10.02 (d, J=6, 1H).

(c) 7β-[DL-2-(4-Ethyl-2,3-dioxopiperazin-1-ylcarbonylamino)-2-(2-thienyl)acetamido]-7α-hydroxyamino-3-[(1,2,3-thiadiazol-5-yl)thiomethyl]ceph-3-em-4-carboxylic acid t-Butyl 7β-[DL-2-(4-ethyl-2,3-dioxopiperazin-1-ylcarbonylamino)-2-(2-thienyl)acetamido]-7α-hydroxyamino-3-[(1,2,3-thiadiazol-5-yl)thiomethyl]ceph-3-em-4-carboxylate (0.25 g) was converted to the title compound by the method of Example 1(f) (0.05 g).

I.R. (KBr) 1780 cm$^{-1}$.

N.M.R. (DMSO d$_6$) δ=1.06 (t, J=6, 3H); 3.2-3.8 (m, 8H); 4.0-4.3 (m, 2H); 5.09 and 5.11 (2s, 1H); 5.96 (d, J=6, 1H); 6.94-7.47 (m, 3H); 8.12 (1H); 8.87 and 8.89 (2s, 1H); 9.53 and 9.58 (2s, 1H); 9.8 (d, J=6, 1H).

EXAMPLE 4

7β-[D-(4-Benzyl-2,3-dioxopiperazin-1-ylcarbonylamino)-2-phenylacetamido]-7α-hydroxyamino-3-[(1,2,3-thiadiazol-5-yl)thiomethyl]ceph-3-em-4-carboxylic acid (a) t-Butyl 7β-[D-(4-benzyl-2,3-dioxopiperazin-1-ylcarbonylamino)-2-phenylacetamido]-7α-methylthio-3-[(1,2,3-thiadiazol-5-yl)thiomethyl]ceph-3-em-4-carboxylic acid The 7α-methylthiocephem (from Example 1(c) (0.38 g) was converted to the title compound (0.32 g) by the method of Example 1(d) using the appropriate acid chloride.

I.R. (CH$_2$Cl$_2$) 1785 cm$^{-1}$.

N.M.R. (CDCl$_3$) δ=1.47 (s, 9H); 2.25 (s, 3H); 3.38-3.6 (m, 4H); 3.8-4.4 (m, 4H); 4.7 (s, 2H); 4.96 (s, 1H); 5.45 (d, J=6, 1H); 7.29-7.50 (m, 10H); 8.51 (s, 1H); 9.93 (d, J=6, 1H).

(b) t-Butyl 7β-[D-(4-benzyl-2,3-dioxopiperazin-1-ylcarbonylamino)-2-phenylacetamido]-7α-hydroxyamino-3-[(1,2,3-thiadiazol-5-yl)thiomethyl]ceph-3-em-4carboxylate t-Butyl 7β-[D-(4-benzyl-2,3-dioxopiperazin-1-ylcarbonylamino)-2-phenylacetamido]-7α-methylthio-3-[(1,2,3-thiadiazol-5-yl)thiomethyl]ceph-3-em-4-carboxylate (0.32 g) was converted to the title compound (0.21 g) by the method of Example 1(e).

I.R. (CH$_2$Cl$_2$) 1785 cm$^{-1}$.

N.M.R. (CDCl$_3$) δ=1.42 (s, 9H); 2.85 and 2.95 (ABq, J=13, 2H); 3.42 (m, 2H); 3.8-4.3 (m, 4H); 4.65 and 4.73 (ABq, 2H, J=14); 5.27 (s, 1H); 5.6 (d, J=6, 1H); 7.29-7.6 (m, 10H); 8.49 (s, 1H); 8.72 (s, 1H); 10.1 (d, J=6, 1H).

(c) 7β-[D-(4-benzyl-2,3-dioxopiperazin-1-ylcarbonylamino)-2-phenylacetamido]-7α-hydroxyamino-3-[(1,2,3-thiadiazol-5-yl)thiomethyl]ceph-3-em-4-carboxylic acid t-Butyl 7β-[D-(4-benzyl-2,3-dioxopiperazin-1-ylcarbonylamino)-2-phenylacetamido]-7α-hydroxyamino-3-[(1,2,3-thiadiazol-5-yl)thiomethyl]ceph-3-em-4-carboxylate (0.21 g) was treated with trifluoroacetic acid in the manner of Example 1(f) to give the title compound (0.13 g).

I.R. (KBr) 1785 cm$^{-1}$.

N.M.R. (DMSO d$_6$/D$_2$O) δ=3.2 and 3.5 (ABq, J=13, 2H); 3.5 (s, 2H); 3.85 (br.s, 2H); 4.12 and 4.25 (ABq, 2H, J=12); 4.55 (s, 2H); 5.07 (s, 1H); 5.7 (d, J=6, 1H); 7.2-7.5 (m, 10H); 8.85 (s, 1H); 9.55 (s, 1H); 9.9 (d, J=6, 1H).

EXAMPLE 5

7β-[DL-2-[4-Methyl-2,3-dioxopiperazin-1-ylcarbonylamino]-2-phenylacetamido]-7α-hydroxyamino-3-[(1,2,3-thiadiazol-5-yl)thiomethyl]-ceph-3-em-4-carboxylic acid (a) t-Butyl 7β-[DL-2-(4-methyl-2,3-dioxopiperazin-1-ylcarbonylamino)-2-phenylacetamido]-7α-methylthio-3-[(1,2,3-thiadiazol-5-yl)-thiomethyl]-ceph-3-em-4-carboxylate t-Butyl 7β-amino-7α-methylthio-3-[(1,2,3-thiadiazol-5-yl)thiomethyl]-ceph-3-em-4-carboxylate and D-2-[4-methyl-2,3-dioxopiperazin-1-ylcarbonylamino]-2-phenylacetyl chloride (Australian Pat. AU 518,792: 22nd Oct., 1981) were reacted together by the method of Example 1(d) to give the title compound.

I.R. (CH$_2$Cl$_2$) 1780 cm$^{-1}$.

N.M.R. (CDCl$_3$) δ=1.46 (s, 9H); 2.02 and 2.24 (2×s, 3H, DL); 3.12 (s, 3H); 3.3→3.7 (m, 4H); 4.0→4.3 (m, 4H); 4.85 and 4.87 (2×s, 1H, DL); 5.60 (d, 1H, J=7.0); 7.35→7.55 (m, 5H); 8.50 and 8.52 (2×s, 1H); 9.96 (d, 1H, J=7.0).

(b) t-Butyl 7β-[DL-2-(4-Methyl-2,3-dioxopiperazin-1-ylcarbonylamino)-2-phenylacetamido]-7α-hydroxyamino-3-[(1,2,3-thiadiazol-5-yl)thiomethyl]-ceph-3-em-4-carboxylate Reaction of the 7α-methylthio compound from part (a) with mercuric acetate and hydroxylamine hydrochloride by the method of Example 2(b) gave the title compound.

I.R. (CH$_2$Cl$_2$) 1780 cm$^{-1}$.

N.M.R. (CDCl$_3$) δ=1.41 and 1.46 (2×s, 9H); 3.10 and 3.13 (2×s; 3H); 3.2→3.7 (m, 4H); 3.8→4.2 (m, 4H); 5.23 and 5.27 (2×s, 1H); 5.60 (d, 1H, J=7.0); 7.3→7.6 (m, 5H); 8.01 (s, 1H); 8.49 and 8.51 (2×s, 1H); 10.05 (d, 1H, J=7.0).

(c) 7β-[DL-2-[4-methyl-2,3-dioxopiperazin-1-ylcarbonylamino]-2-phenylacetamido)-7α-hydroxyamino-3-[(1,2,3-thiadiazol-5-yl)thiomethyl]-ceph-3-em-4-carboxylic acid Deprotection of the cephem t-butylester from part (b) with trifluoroacetic acid by the method of Example 2(c) gave the title compound.

I.R. (KBr) 1785 cm$^{-1}$.

N.M.R. (DMSO d$_6$) δ=2.92 (s, 3H); 3.1→3.7 (m, 4H); 3.8→3.9 (m, 2H); 4.1→4.3 (m, 2H); 5.05 and 5.08 (2×s, 1H); 5.67 (m, 1H); 7.2→7.5 (m, 5H); 8.30 (s, 1H); 8.84 and 8.87 (2×s, 1H); 9.83 (m, 1H).

EXAMPLE 6

7β-[D-2-(4-Ethyl-2,3-dioxopiperazin-1-ylcarbonylamino)-2-phenylacetamido]-7α-hydroxyamino-3-[(1-methyl-1H-tetrazol-5-yl)thiomethyl]ceph-3-em-4-carboxylic acid, sodium salt (a) 7β-[(D-2-(4-Ethyl-2,3-dioxopiperazin-1-ylcarbonylamino)-2-phenylacetamido]-7α-methylthiocephalosporanic acid The t-butyl ester (from Example 2a) (1g) was dissolved in trifluoroacetic acid (3 ml). After 5 minutes at ambient temperature the trifluoroacetic acid was removed in vacuo. TLC monitoring indicated incomplete reaction and the process was repeated. The residue after removal of trifluoroacetic acid was dissolved in dichloromethane:carbon tetrachloride (1:1 mixture, 20 ml) and evaporated. Finally trituration with diethyl ether (10 ml) provided the title compound as an off-white solid (825 mg).

IR (KBr) 1780 cm$^{-1}$.

N.M.R. (DMSO d$_6$) δ=1.1 (t, J=6, 3H); 2.04 (s, 3H); 2.23 (s, 3H); 3.2-3.65 (m, 6H); 3.8-4.0 (m, 2H); 4.65 and 4.97 (2H, ABq, J=13); 5.1 (s, 1H); 5.67 (d, J=7, 1H); 7.25-7.55 (m, 5H); 9.69 (s, NH); 9.84 (d, J=7, NH); 13.77 (brs, COOH).

(b) 7β-[D-2-(4-Ethyl-2,3-dioxopiperazin-1-ylcarbonylamino)-2-phenylacetamido]-3-[(1-methyl-1H-tetrazol-5-yl)thiomethyl]-7α-methylthioceph-3-em-4-carboxylic acid A solution of 7β-[D-2-(4-ethyl-2,3-dioxopiperazin-1-ylcarbonylamino)-2-phenylacetamido]-7α-methylthiocephalosporanic acid (1.2 g) and 5-mercapto-1-methyltetrazole (0.45 g) in 1,2-dichloroethane (75 ml) was refluxed under nitrogen for 3 hours. The mixture was cooled to room temperature and the title compound filtered and dried in vacuo (0.32 g).

IR (KBr) 1780 cm$^{-1}$.

N.m.r. (DMSO-d$_6$) δ=1.10 (t, J=6, 3H); 2.23 (s, B 3H); 3.3-3.8 (m, 8H); 3.9 (s, 3H); 4.18 and 4.40 (2H, ABq, J=13); 5.05 (s, 1H); 5.66 (d, J=7, 1H); 7.3-7.5 (m, 5H); 9.68 (s, NH); 9.83 (d, J=7, NH).

(c) 7β-[D-2-[4-Ethyl-2,3-dioxopiperazin-1-ylcarbonylamino]-2-phenylacetamido]-7α-hydroxyamino-3-[(1-methyl-1H tetrazol-5-yl)thiomethyl]ceph-3-em-4-carboxylic acid, sodium salt The 7α-methylthiocephem from part (b) above (0.29 g) in dimethylformamide (20 ml) was cooled to −60° and a solution of mercuric acetate (137 mg) in dimethylformamide (5 ml) added. After 3 minutes a suspension of hydroxylamine hydrochloride (30 mg) and triethylamine (120 µl) in dimethylformamide (5 ml) was added. The mixture was warmed to 20° C. and stirred for 1 hour. Ethyl acetate and saturated brine were added and the mixture was acidified to pH2 with 2N hydrochloric acid and filtered through "Hyflo" (Registered Trade Mark). The organic layer was separated and washed thoroughly with brine, dried (Na$_2$SO$_4$) and evaporated in vacuo. The residue was suspended in water and neutralised with aqueous sodium bicarbonate (pH 7.5) then freeze dried to yield the title compound (56 mg).

I.R. (KBr) 1765 cm$^{-1}$.

N.M.R. (D$_2$O) δ=1.21 (t, J=7, 3H); 3.5-3.8 (m, 6H); 3.9-4.3 (m, 4H); 4.00 (s, 3H); 5.10 (s, 1H); 5.53 (s, 1H); 7.4-7.6 (m, 5H).

EXAMPLE 7

7β-[D-2-(4-Ethyl-2,3-dioxopiperazin-1-ylcarbonylamino)-2-phenylacetamido]-7α-hydroxyamino-3-(pyridiniummethyl)ceph-3-em-4-carboxylate (a) 7β-[D-2-(4-Ethyl-2,3-dioxopiperazin-1-ylcarbonylamino)-2-phenylacetamido]-7α-methylthio-3-(pyridiniummethyl)ceph-3-em-4-carboxylate 7β-[D-2-(4-Ethyl-2,3-dioxopiperazin-1-ylcarbonylamino)-2-phenylacetamido]-7α-methylthiocephalosporanic acid (Example 6a) (1.86 g) was dissolved in water (10 ml) containing sodium bicarbonate (250 mg) then potassium iodide (7.4 g) and pyridine (750 µl) were added. The solution was heated at 70° for 90 minutes then cooled and concentrated in vacuo to 5 ml. This was diluted with acetone (50 ml) and chromatographed over silica (75 g) eluting with acetone-water (3:1) to afford the crude title compound (1.2 g). This material was dissolved in water (5 ml), filtered through "Hyflo" and freeze dried to afford the title compound (650 mg).

I.R. (KBr) 1780 cm$^{-1}$.

N.M.R. (DMSO d$_6$ δ=1.08 (t, J=7.5, 3H); 2.27 (s, 3H); 2.85 and 3.00 (ABq, J=17, 2H, C(2)-CH$_2$); 3.4 (q, J=7.5, 2H); 3.5-4.0 (m, 4H); 4.95 (s, H); 5.13 and 5.56 (ABq, J=12.5, 2H); 5.65 (d, J=8.5, 1H); 7.2-7.5 (m, 5H); 8.1-9.45 (m, 5H); 9.6 (s, NH); 9.8 (d, J=8.5, NH).

(b) 7β-[D-2-(4-Ethyl-2,3-dioxopiperazin-1-ylcarbonylamino)-2-phenylacetamido]-7α-hydroxyamino-3-(pyridiniummethyl)ceph-3-em-4-carboxylate The product from Example 7a (640 mg) was dissolved in dry dimethylformamide (6 ml) and cooled under nitrogen to −50°. A solution of mercuric acetate (350 mg) in dimethylformamide (2 ml) was added followed by a slurry of hydroxylamine hydrochloride (77 mg) and triethylamine (153 μl) in dimethylformamide (1 ml). The reaction was stirred at −50° for 30 minutes and at −20° for 30 minutes then diluted with acetone (50 ml) and chromatographed over silica. Elution with acetone:water (3:1) provided the crude product. After evaporation of the solvents, the product was re-dissolved in water (5 ml), filtered through "Hyflo" and freeze dried to give the title compound (300 mg).

I.R. (KBr) 1780 cm$^{-1}$.

N.M.R. (DMSO d$_6$) δ=1.13 (t, 7.5, 3H); 2.84 and 2.96 (ABq, J=16, C-(2)-CH$_2$); 3.3–4.0 (m, 6H); 5.0 (s, 1H, C(6)-H); 5.1 and 5.6 (ABq, J=13.5 z, 2H); 5.7 (d, J=8.5, 1H, φ-CH-NH); 6.35 (s, 1H, exch); 7.2–7.6 (m, 5H); 8.1–9.4 (m, 6H, pyridine+1H, exch); 9.55 (s, NH); 9.9 (d, J=8.5, NH).

EXAMPLE 8

3-(2,3-Cyclopentenopyridiniummethyl)-7β-[D-2-(4-ethyl-2,3-dioxopiperazin-1-ylcarbonylamino)-2-phenylacetamido]-7α-hydroxyaminoceph-3-em-4-carboxylate (a) 3-(2,3-Cyclopentenopyridiniummethyl)-7β-[D-2-(4-ethyl-2,3-dioxopiperazin-1-ylcarbonylamino)-2-phenylacetamido]-7α-methylthioceph-3-em-4-carboxylate The above compound was prepared from the product of 6(a) by the method described in Example 7a using 2,3-cyclopentenopyridine in place of pyridine.

I.R. (KBr) 1775 cm$^{-1}$.

N.M.R. (DMSO-D$_6$) δ=1.1 (t, J=7.1, 3H); 2.28 (s, 3H); 2.8–4.0 (m, 14H); 4.92 (s, 1H, C(6)-H); 5.25 and 5.36 (ABq, J=14.4, 2H); 5.66 (d, J=7.2, 1H φ-CH-NH); 7.1–7.7 (m, 5H); 7.8–9.2 (m, 3H); 9.67 (s, NH); 9.82 (d, J=7.2, NH).

(b) 3-(2,3-Cyclopentenopyridiniummethyl)-7β-[D-2-(4-ethyl-2,3-dioxopiperazin-1-ylcarbonylamino)-2-phenylacetamido]-7α-hydroxyaminoceph-3-em-4-carboxylate The product from Example 8(a) (140 mg) was dissolved in dry dimethylformamide (5 ml) and cooled under nitrogen to −50°. A solution of mercuric acetate (72 mg) in dimethylformamide (0.5% ml) was added followed by a slurry of hydroxylamine hydrochloride (14 mg) and triethylamine (29 μl) in dimethylformamide (1 ml). The reaction was stirred at −20° for 30 minutes then diluted with diethyl ether (100 ml) and the crude product filtered and washed with diethyl ether (50 ml). The product was slurried in water (25 ml) and hydrogen sulphide bubbled through the suspension for 10 minutes. The slurry was filtered and the filtrate freeze dried to give the title compound (95 mg).

I.R. (KBr) 1770 cm$^{-1}$.

N.M.R. (DMSO-D$_6$) δ=1.1 (t, J=7.1, 3H); 3.1–4.0 (brm, 14H); 4.9 (s, 1H, C(6)-H); 5.1–5.4 (brm, 2H); 5.7 (d, J=7.2, 1H, φ-CH-NH); 6.4 (s, 1H, exch); 7.2–7.6 (m, 5H); 8.15 (s, 1H, exch); 7.9, 8.35 and 9.15 (m, 3H, pyridine); 9.5–9.6 (brs, NH); 9.88 (d, J=7.2, NH).

EXAMPLE 9

3-[(1-Carboxymethyl-1H-tetrazol-5-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid (a) 3-[(1-Carboxymethyl-1H-tetrazol-5-yl)thiomethyl]-7β-[D-2-(4-ethyl-2,3-dioxopiperazin-1-ylcarbonylamino)-2-phenylacetamido]-7α-methylthioceph-3-em-4-carboxylic acid 7-β-[D-2-(4-Ethyl-2,3-dioxopiperazin-1-ylcarbonylamino)-2-phenylacetamido]-7α-methylthiocephalosporanic acid (Example 6(a)) (1.3 g) was dissolved in water (20 ml) containing sodium bicarbonate (565 mg) then 1-carboxymethyl-1H-tetrazole-5-thiol (403 mg) was added. The solution was heated at 65° for 6 hours under a nitrogen atmosphere then cooled and stirred with decolourising charcoal (0.5 g) for 0.5 hours. After filtration the solution was cooled to 5° and acidified to pH 2 with concentrated hydrochloric acid. The precipitated solid was filtered, washed with water (10 ml) and dried under vacuum to yield the title compound (1.05 g).

I.R. (KBr) 1775 cm$^{-1}$.

N.M.R. (DMSO-D$_6$) δ=1.09 (t, J=7, 3H); 2.22 (s, 3H); 3.25–3.70 (m, 6H); 3.87–3.95 (m, 2H); 4.14 and 4.52 (ABq, J=13, 2H); 5.01 (s, 1H); 5.26 and 5.35 (ABq, J=18, 2 H); 5.65 (d, J=7, 1H); 7.28–7.50 (m, 5H); 9.69 (s, NH); 9.82 (d, J=7, NH).

(b) 3-[(1-Carboxymethyl-1H-tetrazol-5-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid The 7α-methylthiocephem (from Example 9(a)) (144 mg) in dimethylformamide (3 ml) was cooled to −60° and treated successively with solutions of mercuric acetate (127 mg) in dimethylformamide (1 ml), hydroxylamine hydrochloride (15.3 mg) in dimethylformamide (1 ml) and triethylamine (31 μl). The resultant clear solution was warmed to 0° over 1 hour and added slowly to diethyl ether (100 ml) with stirring. After filtration, the ether-damp solid was suspended in methanol (15 ml) and saturated with hydrogen sulphide. The mixture was filtered and evaporated under vacuum. The residue was triturated with methylene chloride (10 ml) to give the title compound as a white solid (98 mg).

I.R. (KBr) 1775 cm$^{-1}$.

N.M.R. (DMSO-D$_6$) δ=1.09 (t, J=7, 3H); 3.05–3.82 (m, 6H); 3.85–4.00 (m, 2H); 4.12 and B 4.46 (ABq, J=13, 2H); 4.98 (s, 1H); 5.22–5.28 (m, 2H); 5.69 (d, J=7, 1H); 6.51 (brs, 1H); 7.22–7.54 (m, 5H); 8.17 (s, 1H); 9.55 (s, NH); 9.87 (d, J=7, NH).

EXAMPLES 10 TO 13

The following compounds of the formula (I) were prepared from the appropriate starting materials by the methods described in Example 9 parts (a) and (b).

| Example No. and side chain stereo-chemistry | R | R¹ | R² | I.R. (KBr) cm⁻¹ | N.M.R. (DMSO—d₆) |
|---|---|---|---|---|---|
| 10 2R, 3S— | CH₃CH(OH)— | 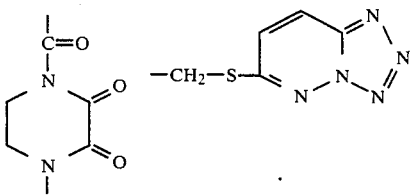 | —CH₂—S—  | 1775 | δ = 1.1–122 (m, 6H); 3.2–3.6 (m, 6H); 3.9 (m, 2H); 4.15 and 4.5 (ABq, 2H, J = 15); 4.36 (m, 2H); 5.02 (d, 1H, J = 4); 5.08 (s, 1H); 6.38 (s, 1H); 7.75 (d, 1H, J = 10); 7.93 (s, 1H); 8.1 (s, 1H); 8.56 (d, 1H, J = 10); 8.89 (s, 1H); 9.28 (d, 1H, J = 7). |
| 11 2R, 3S— | CH₃CH(OH)— | 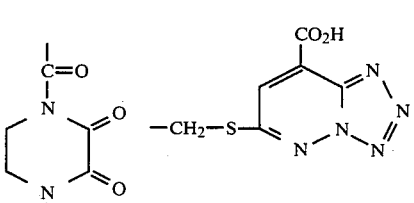 | —CH₂—S—  | 1775 | δ = 1.05–1.1 (m, 6H); 3.18–3.7 (m, 6H); 3.9 (m, 2H); 4.1 and 4.52 (ABq, 2H, J = 14); 4.34 (m, 2H); 5.02 (broad s, 1H); 5.09 (s, 1H); 6.4 (broad s, 1H); 7.93 (s, 1H); 8.1 (s, 1H); 8.9 (s, 1H); 9.27 (d, 1H, J = 7). |
| 12 2R, 3S— | CH₃CH(OH)— | 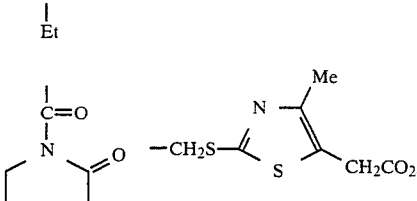 | —CH₂S—  | 1780 | δ = 1.05–1.12 (m, 6H); 2.22 (s, 3H); 3.2–3.78 (m, 8H); 3.9 (m, 2H); 4.02 and 4.41 (ABq, 2H, J = 14); 5.02 (broad s, 1H); 5.06 (s, 1H); 7.93 (s, 1H); 8.1 (s, 1H); 8.89 (s, 1H); 9.28 (d, 1H, J = 7). |
| 13 D— | Ph— | 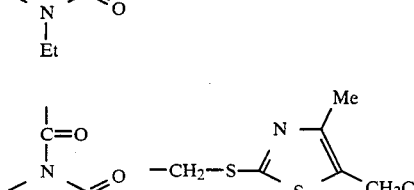 | —CH₂—S—  | 1780 | δ = 1.07 (t, J = 7, 3H); 2.19 (s, 3H); 3.06–3.52 (m, 6H); 3.72 (s, 2H); 3.86 (m, 2H); 3.95 and 4.41 (ABq, J = 13, 2H); 4.97 (s, 1H); 5.65 (d, J = 7, CHNH); 6.46 (brs., 1H); 7.28–7.44 (m, 5H); 8.13 (s, 1H); 9.52 (s, 1H); 9.85 (d, J = 7, NH). |

EXAMPLE 14

3-[2,5-Dihydro-6-hydroxy-2-methyl-5-oxo-1,2,4-triazin-3-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid (a) 3-[(2,5-Dihydro-6-hydroxy-2-methyl-5-oxo-1,2,4-triazin-3-yl)thiomethyl]-7β-[D-2-(4-ethyl-2,3-dioxopiperazin-1-ylcarbonylamino)-2-phenylacetamido]-7α-methylthioceph-3-em-4-carboxylic acid 7β-[D-2-(4-Ethyl-2,3-dioxopiperazin-1-ylcarbonylamino)-2-phenylacetamido]-7α-methylthiocephalosporanic acid (Example 6(a)) (619 mg) was dissolved in water (20 ml) containing sodium bicarbonate (185 mg) then 2,5-dihydro-6-hydroxy-2-methyl-5-oxo-1,2,4-triazine-3-thiol (191 mg) was added. The solution was preheated at 65° for 5 hours under a nitrogen atmosphere, with addition of 5% aqueous sodium bicarbonate solution as necessary to maintain the pH at 6.0–6.5. After cooling to 5° concentrated hydrochloric acid was added to pH 2 and the mixture was filtered. Washing with water (2 ml), followed by drying under vacuum gave the title compound (531 mg).

I.R. (KBr) 1775 cm⁻¹.

N.M.R. (DMSO-D₆) δ=1.09 (t, J=7, 3H); 2.24 (s, 3H); 3.20–3.75 (m, 6H); 3.59 (s, 3H); 3.85–3.97 (m, 2H); 4.06 and 4.35 (ABq, J=13, 2H); 5.05 (s, 1H); 5.65 (d, J=7, 1H); 7.22–7.56 (m, 5H); 9.67 (s, NH); 9.82 (d, J=7, NH).

(b) 3-[2,5-Dihydro-6-hydroxy-2-methyl-5-oxo-1,2,4-triazin-3-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid was prepared from the 7α-methylthiocephem of part (a) using the method of Example 9(b).

I.R. (KBr) 1775 cm⁻¹.

N.M.R. (DMSO-D₆) δ=1.09 (t, J=7, 3H); 3.05–3.75 (m, 6H); 3.59 (s, 3H); 3.83–3.97 (m, 2H); 4.03 and 4.33 (ABq, J=13, 2H); 5.03 (s, 1H); 5.69 (d, J=7, 1H); 6.52 (brs, 1H); 7.20–7.56 (m, 5H); 8.18 (s, 1H); 9.55 (s, NH); 9.87 (d, J=7, NH).

EXAMPLE 15

3-[(5,6-Dioxo-4-methyl-1,4,5,6-tetrahydro-1,2,4-triazin-3-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid (a) 3-[(5,6-Dioxo-4-methyl-1,4,5,6-tetrahydro-1,2,4-triazin-3-yl)thiomethyl]-7β-[D-2-(4-ethyl-2,3-dioxopiperazin-1-ylcarbonylamino)-2-phenylacetamido]-7α-methylthioceph-3-em-4-carboxylic acid 7β-[D-2-(4-Ethyl-2,3-dioxopiperazin-1-ylcarbonylamino)-2-phenylacetamido]-7α-methylthiocephalosporanic acid [Example 6(a)] (619 mg) was treated with 5,6-dioxo-4-methyl-1,4,5,6-tetrahydro-1,2,4-triazine-3-thiol (191 mg) in a similar manner to that described in Example 14(a) to give the title compound, (470 mg).

I.R. (KBr) 1775 cm$^{-1}$.

N.M.R. (DMSO d$_6$) δ=1.09 (t, J=7, 3H); 2.23 (s, 3H); 3.27 (s, 3H); 3.29 (m, 6H); 3.91 (m, 2H); 3.97 and 4.16 (ABq, J=13, 2H); 5.06 (s, 1H); 5.65 (d, J=7, 1H); 7.35–7.48 (m, 5H); 9.69 (s, 1H); 9.83 (d, J=7, 1H); 12.45 (s, 1H).

(b) 3-[(5,6-Dioxo-4-methyl-1,4,5,6-tetrahydro-1,2,4-triazin-3-yl)thiomethyl]-7β-[D-2-(4-ethyl-2,3-dioxopiperazin-1-ylcarbonylamino)-2-phenylacetamido]-7α-hydroxyaminoceph-3-em-4-carboxylic acid The title compound (330 mg) was prepared from the 7α-methylthiocephem of part (a) above (420 mg) by the method of Example 9(b).

I.R. (KBr) 1780 cm$^{-1}$.

N.M.R. (DMSO d$_6$) δ=1.09 (t, J=7, 3H); 3.26 (s, 3H); 3.24–3.57 (m, 6H); 3.89 (m, 2H); 3.94 and 4.13 (ABq, J=13, 2H); 5.03 (s, 1H); 5.70 (d, J=7, 1H); 7.28–7.47 (m, 5H); 9.56 (s, 1H); 9.87 (d, J=7, 1H); 12.43 (s, 1H).

EXAMPLE 16

7β-[D-2-(4-Ethyl-2,3-dioxopiperazin-1-ylcarbonylamino)-2-phenylacetamido]-7α-hydroxyamino-3-[(1-(2-hydroxyethyl)-1H-tetrazol-5-yl)thiomethyl]ceph-3-em-4-carboxylic acid (a) 7β-[D-2-(4-Ethyl-2,3-dioxopiperazin-1-ylcarbonylamino)-2-phenylacetamido]-3-[(1-(2-hydroxyethyl)-1H-tetrazol-5-yl)thiomethyl]-7α-methylthioceph-3-em-4-carboxylic acid 7β-[D-2-(4-Ethyl-2,3-dioxopiperazin-1-ylcarbonylamino)-2-phenylacetamido]-7α-methylthiocephalosporanic acid [Example 6(a)] (1.18 g) was treated with 1-(2-hydroxyethyl)-1H-tetrazole-5-thiol (835 mg) in a similar manner to that described in Example 6(b) to give the title compound (810 mg).

I.R. (KBr) 1780 cm$^{-1}$.

N.M.R. (DMSO-D$_6$) δ=1.09 (t, J=7.5, 3H); 2.22 (s, 3H); 3.31–3.65 (m, 6H); 3.75 (t, J=5, 2H); 3.91 (m, 2H); 4.16 and 4.42 (ABq, J=13, 2H); 4.32 (t, J=5, 2H); 5.01 (s, 1H); 5.65 (d, J=7, 1H); 7.28–7.47 (m, 5H); 9.68 (s, 1H); 9.83 (d, J=7, 1H).

(b) 7β-[D-2-(4-Ethyl-2,3-dioxopiperazin-1-ylcarbonylamino)-2-phenylacetamido]-7α-hydroxyamino-3-[(1-(2-hydroxyethyl)-1H-tetrazol-5-yl)thiomethyl]ceph-3-em-4-carboxylic acid The title compound (160 mg) was prepared from the 7α-methylthiocephem (from Example 16(a) above) (200 mg) by treatment with mercuric acetate and hydroxylamine hydrochloride as described in Example 9(b).

I.R. (KBr) 1775 cm$^{-1}$.

N.M.R. (DMSO-D$_6$) δ=1.09 (t, J=7, 3H); 3.24–3.62 (m, 6H); 3.74 (t, J=5, 2H); 3.89 (m, 2H); 4.13 and 4.42 (ABq, J=13, 2H); 4.33 (t, J=5, 2H); 5.00 (s, 1H); 5.70 (d, J=7, 1H); 7.25–7.49 (m, 5H); 8.19 (broad s, 1H); 9.57 (s, 1H); 9.89 (d, J=7, 1H); 10.27 (broad s, 1H).

EXAMPLES 17 TO 35

The following compounds of the formula (I) were prepared from the appropriate starting materials using the methods of Example 16 parts (a) and (b). In part (a) generally reflux was carried out for 14–16 hours. [CBZ=benzyloxycarbonyl.]

| Example No. and side chain stereochemistry | R | R$^1$ | R$^2$ |
|---|---|---|---|
| 17<br>2R, 3S— | CH$_3$CH(OH)— | —C(=O)—N(piperazine)N—Et (2,3-dioxo) | —CH$_2$—S—(tetrazole N-Me) |
| 18<br>2R, 3S— | CH$_3$CH(OH)— | —C(=O)—N(piperazine)N—Et (2,3-dioxo) | —CH$_2$—S—(triazine NH, N-Me, dioxo) |
| 19<br>DL- | CBZ—O—C$_6$H$_4$— | —C(=O)—N(piperazine)N—Et (2,3-dioxo) | —CH$_2$—S—(triazine NH, N-Me, dioxo) |

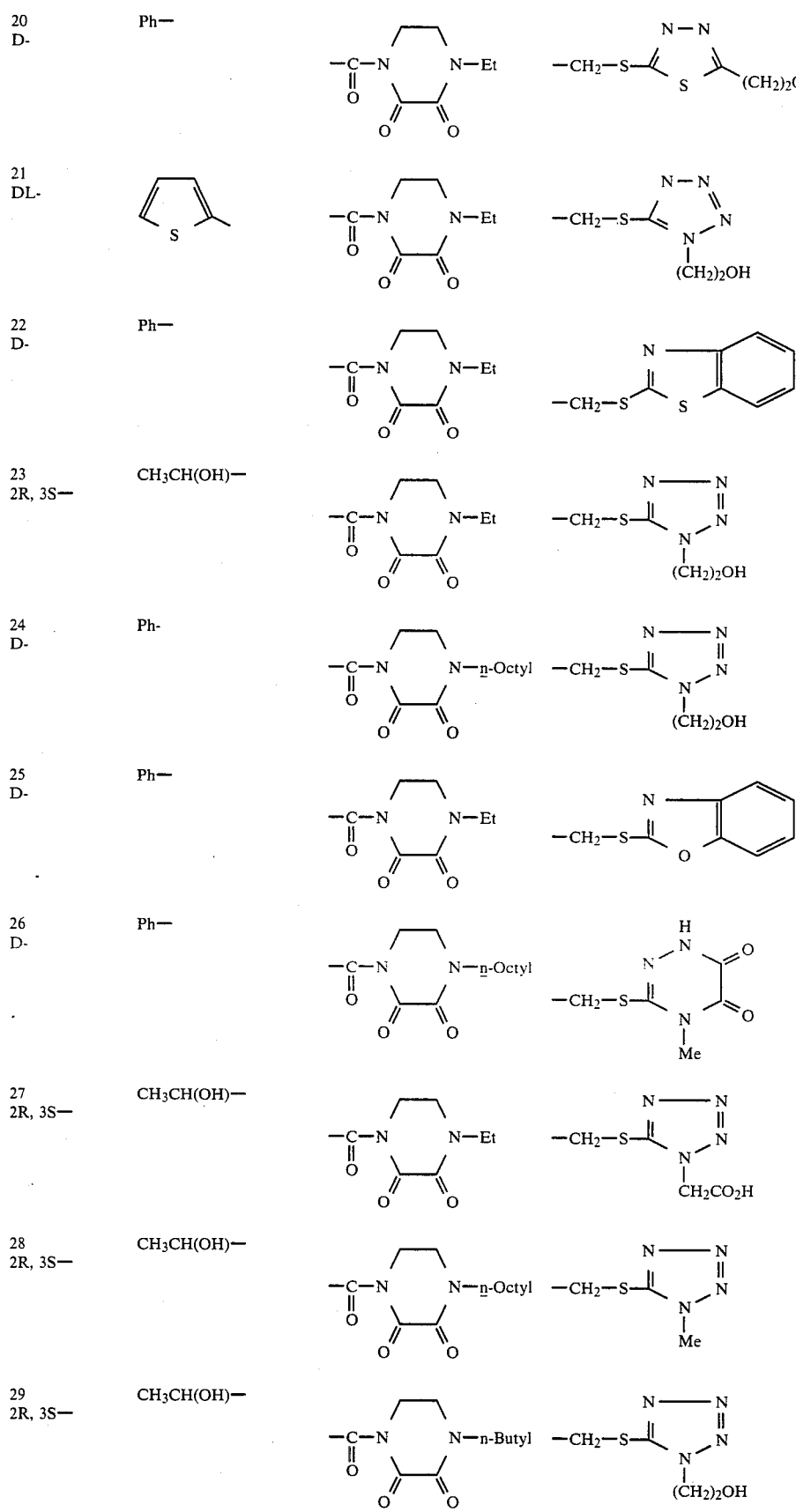

-continued
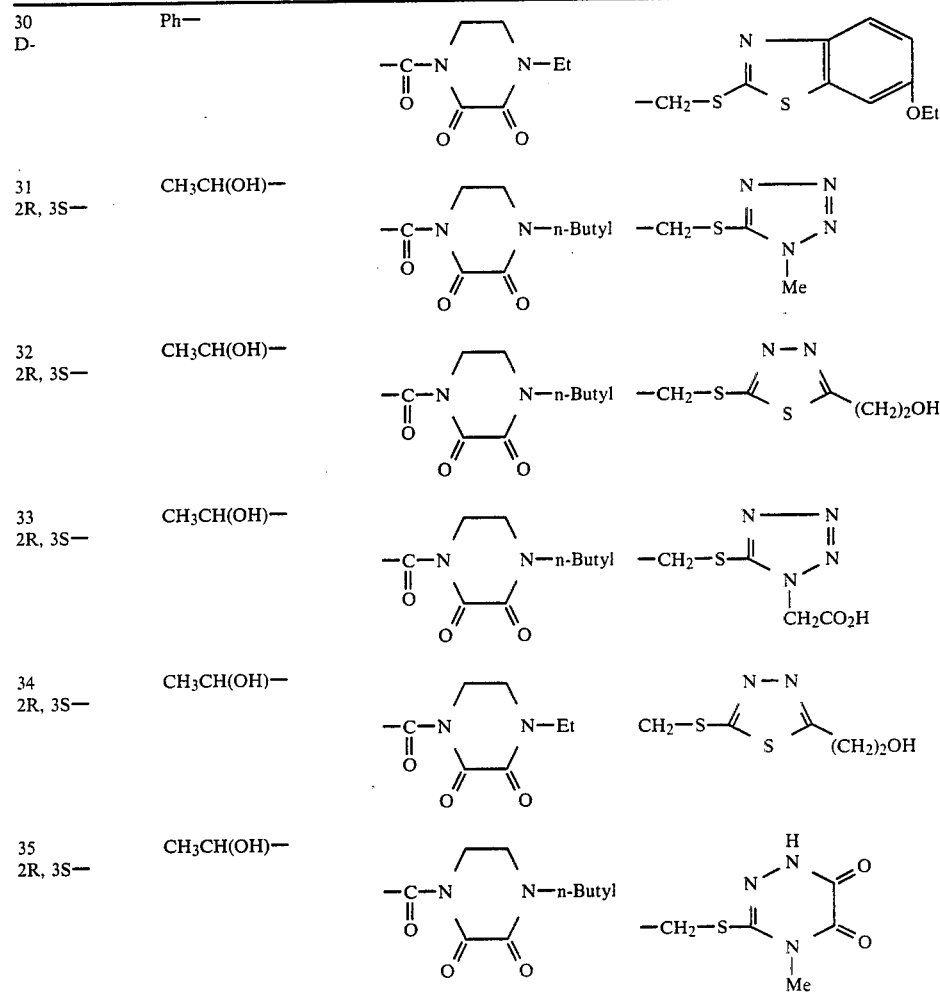
| Example No. and side chain stereo-chemistry | I.R. (KBr) cm$^{-1}$ | N.M.R. (DMSO—d$_6$) |
|---|---|---|
| 17 2R, 3S— | 1777 | δ = 1.1 (m, 6H); 3.32 to 3.76 (m, 6H); 3.91 (s, 3H); 3.97 (m, 2H); 4.15 and 4.35 (ABq, 2H, J = 12); 4.31 (m, 2H), 5.05 (s, 1H); 8.88 (s, 1H); 9.27 (d, 1H, J = 6). |
| 18 2R, 3S— | 1775 | δ = 1.08 (m, 6H); 3.27 (s, 3H); 3.29 to 4.14 (m, 10H); 4.36 (m, 2H); 5.09 (s, 1H); 8.91 (s, 1H); 9.28 (d, 1H, J = 9). |
| 19 DL- | 1775 | δ = 1.07 (t, J = 7, 3H); 3.24 and 3.26 (2 × s, 3H); 3.20–3.67 (m, 6H); 3.82–4.13 (m, 4H); 5.00 and 5.06 (2 × s, C$_6$—H); 5.23 and 5.24 (2 × s, 2H); 5.70 (d, J = 7, C̲HNH); 7.18–7.50 (m, 9H); 8.12 (brs., 1H); 9.50 and 9.56 (2 × s, 1H); 9.83 and 9.86 (2 × d, J = 7, NH). |
| 20 D- | 1778 | δ = 1.15 (t, 3H, J = 6); 2.95 (t, 2H, J = 6); 3.00 to 3.95 (m, 10H); 4.10 and 4.48 (ABq, 2H, J = 15); 5.01 (s, 1H); 5.68 (d, 1H, J = 6); 7.10 to 7.50 (m, 5H); 9.52 (s, 1H); 9.83 (d, 1H, J = 6). |
| 21 DL- | 1780 | δ = 1.08 (t, 3H, J = 6); 3.25 to 4.05 (m, 10H); 4.10 to 4.44 (m, 4H); 5.01 and 5.03 (2 × s, 1H, D and L forms); 5.97 (m, 1H); 6.90 to 7.55 (m, 3H); 9.67 and 9.69 (2 × s, 1H, D and L NH̲); 9.79 (m, 1H). |
| 22 D- | 1780 | δ = 1.05 (t, J = 3Hz, 3H); 3.1–3.65 (m, 6H); 3.85 (m, 2H); 4.12 and 4.73 |

-continued

| | | |
|---|---|---|
| | | (ABq., J = 12 Hz, 2H); 4.98 (s, 1H); 5.65 (d, J = 6Hz, 1H); 6.48 (s, 1H); 7.24-7.45 (m, 8H); 7.85 (d, J = 12Hz, 1H); 7.99 (d, J = 12Hz, 1H); 8.13 (s, 1H); 9.53 (s, 1H); 9.84 (d, J = 6Hz, 1H). |
| 23 2R, 3S— | 1775 | δ = 1.05-1.15 (m, 6H); 3.35-4 (m, 10H); 4.1-4.4 (m, 6H); 5.05 (s, 1H); 8.9 (s, 1H); 9.25 (d, 1H, J = 7). |
| 24 D- | 1780 | δ = 0.85 (t, J = 7, 3H); 1.24 (s, 10H); 1.48 (brs., 2H); 3.25 and 3.57 (Abq, J = 18, 2H); 3.33-3.38 (m, 2H); 3.53 (m, 2H); 3.72 (m, 2H); 3.86 (m, 2H); 4.18 and 4.41 (ABq, J = 12, 2H); 4.32 (m, 2H); 4.97 (s, 1H); 5.08 (brs., 1H); 5.68 (d, J = 8, C̲H̲NH); 6.50 (brs., 1H); 7.29-7.45 (m, 5H); 8.18 (s, 1H); 9.42 (brs., 1H); 9.54 (s, 1H); 9.86 (d, J = 8, NH). |
| 25 D- | 1780 | δ = 1.06 (t, J = 6Hz, 3H); 3.53 (m, 2H); 3.25-3.45 (m, 4H); 3.88 (m, 2H); 4.13 and 4.62 (ABq, J = 12Hz, 2H); 5.00 (s, 1H); 5.66 (d, J = 6Hz, 1H); 6.50 (ex); 7.24-7.63 (m, 10H); 8.15 (ex); 9.54 (ex); 9.86 (d, J = 6Hz, 1H). |
| 26 D- | 1780 | δ = 0.83 (t, J = 6, 3H); 1.22 (s, 10H); 1.46 (s, 2H); 3.23 (s, 3H); 3.25-3.58 (m, 6H); 3.86 (m, 2H); 3.90 and 4.08 (ABq, J = 12, 2H); 4.99 (s, 1H); 5.66 (d, J = 8, C̲H̲NH); 5.64 (brs., 1H); 6.48 (s, 1H); 7.25-7.44 (m, 5H); 8.16 (s, 1H); 9.54 (s, 1H); 9.78 (brs., 1H); 9.85 (d, J = 8, NH). |
| 27 2R, 3S— | 1777 | δ = 1.06 (m, 6H); 3.20 to 3.61 (m, 6H); 3.91 (m, 2H); 4.15 and 4.38 (ABq, 2H, J = 15); 4.36 (m, 2H); 4.93 (s, 1H); 5.26 (s, 2H); 8.09 (s, 1H); 8.89 (s, 1H); 9.26 (d, 1H, J = 6). |
| 28 2R, 3S— | 1775 | δ = 0.83 (t, J = 6, 3H); 1.06 (d, J = 6, 3H); 1.23 (m, 10H); 1.47 (m, 2H); 3.0-4.0 (m, 8H and s, 3H(δ = 3.9); 4.10-4.40 (m, 3H); 5.02 (m, 2H); 6.40 (s, NH); 8.10 (s, NH—O̲H̲); 8.88 (s, NH); 9.30 (d, J = 6, NH). |
| 29 2R, 3S— | 1778 | δ = 0.86 (t, 3H, J = 7.5); 1.07 (d, 3H, J = 6); 1.25 (m, 2H); 1.47 (m, 2H); 3.23 to 3.77 (m, 8H); 3.89 (m, 2H); 4.03 (m, 2H); 4.14 and 4.36 (ABq, 2H, J = 12); 4.22 (t, 2H, J = 6); 5.04 (s, 1H); 6.41 (broad s, 1H); 8.10 (s, 1H); 8.89 (s, 1H); 9.27 (d, 1H, J = 6). |
| 30 D- | 1780 | δ = 1.04 (t, J = 6Hz, 3H); 1.32 (t, J = 6Hz, 3H); 3.35 (ABq, J = 4Hz, 2H); 3.52 (br, 2H); [broad HOD peak obscuring protons between 3.9-4.8]; 4.98 (s, 1H); 5.64 (d, J = 6Hz, 1H); 7.03-7.73 (m, 9H); 9.53 (s, 1H); 9.84 (d, J = 6Hz, 1H). |
| 31 2R, 3S— | 1778 | δ = 0.86 (t, 3H, J = 7.5); 1.07 (d, 3H, J = 6); 1.25 (m, 2H); 1.47 (m, 2H); 3.32 to 4.10 (m, 8H); 3.91 (s, 3H); 4.14 and 4.34 (ABq, 2H, J = 12); 4.33 (m, 2H); 5.05 (s, 1H); 8.89 (s, 1H); 9.27 (d, 2H, J = 6). |
| 32 2R, 3S— | 1777 | δ = 0.86 (t, 3H, J = 7.5); 1.07 (d, 3H, J = 6); 1.24 (m, 2H); 1.47 (m, 2H); 3.13 (t, 2H, J = 4.5); 3.34 to 3.74 (m, 6H); 3.89 (m, 2H); 4.03 (m, 2H); 4.16 and 4.48 (ABq, 2H, J = 15); 4.34 (m, 2H); 5.01 (d, 1H, J = 3); 5.07 (s, 1H); 6.41 (broad s, 1H); 8.10 (s, 1H); 8.89 (s, 1H); 9.27 (d, 1H, J = 6). |
| 33 2R, 3S— | 1768 | δ = 0.88 (t, 3H, J = 4.5); 1.08 (d, 3H, J = 6); 1.13 (m, 2H); 1.46 (m, 2H); 3.21 to 4.08 (m, 8H); 4.15 and 4.38 (ABq, 2H, J = 15); 4.31 (m, |

| | | |
|---|---|---|
| | | 2H); 4.91 (s, 1H); 5.05 (s, 1H); 5.17 (m, 2H); 6.41 (broad s, 1H); 8.11 (s, 1H); 8.98 (s, 1H); 9.31 (d, 1H, J = 6). |
| 34 2R, 3S— | 1780 | δ = 1.11 (m, 6H); 2.80 to 4.10 (m, 12H); 4.15 and 4.45 (ABq, 2H, J = 15); 4.31 (m, 2H); 5.05 (s, 1H); 8.88 (s, 1H); 9.31 (d, 1H, J = 6). |
| 35 2R, 3S— | 1778 | δ = 0.87 (t, 3H, J = 6); 1.08 (d, 3H, J = 6); 1.25 (m, 2H); 1.46 (m, 2H); 3.26 (s, 3H); 3.33 to 3.72 (m, 6H); 3.90 to 4.13 (m, 4H); 4.35 (m, 2H); 5.03 (m, 1H); 5.07 (s, 1H); 8.12 (s, 1H); 8.90 (s, 1H); 9.27 (d, 1H, J = 9). |

EXAMPLE 36

7β-[D-2-(4-Ethyl-2,3-dioxopiperazin-1-ylcarbonylamino)-2-phenylacetamido]-7α-hydroxyamino-3-[(1-potassiumsulphomethyl-1H-tetrazol-5-yl)thiomethyl]ceph-3-em-carboxylic acid
[Potassiumsulphomethyl=—CH$_2$SO$_2$O$^\ominus$K$^\oplus$]

(a) 7β-[D-2-(4-Ethyl-2,3-dioxopiperazin-1-ylcarbonylamino)-2-phenylacetamido]-7α-methylthio-3-[(1-potassiumsulphomethyl-1H-tetrazol-5-yl)thiomethyl]-ceph-3-em-4-carboxylic acid Tetrabutylammonium hydrogen sulphate (1.65 g) was added to a suspension of 1-sulphomethyltetrazole-5-thiol sodium salt (1.05 g) in 1,2-dichloroethane (30 ml) at room temperature and the mixture stirred for 15 minutes. Filtration gave a clear colourless solution of 1-sulphomethyltetrazole-5-thiol tetrabutylammonium salt which was added to a suspension of 7β-[D-2-(4-ethyl-2,3-dioxopiperazin-1-ylcarbonylamino)-2-phenylacetamido]-7α-methylthiocephalosporanic acid (Example 6(a)) (1.0 g) in 1,2-dichloroethane (200 ml) and the mixture warmed to reflux temperature. The resulting clear solution was stirred under reflux for 17 hours, cooled, filtered and evaporated under vacuum. The residual oil was taken up in acetone (100 ml and a solution of potassium nonafluorobutanesulphonate (1.64 g) in acetone (20 ml) was added and the resulting slurry stirred for 15 minutes. The acetone was decanted, the solid was washed with acetone (3×50 ml) and dried under vacuum to give the title compound (1.04 g).

I.R. (KBr) 1776 cm$^{-1}$.

N.M.R. (DMSO-D$_6$) δ=1.09 (t, J=7, 3H); 2.22 (s, 3H); 3.36–3.64 (m, 6H); 3.92 (m, 2H); 4.05 and 4.47 (ABq, J=13, 2H); 4.94–5.10 (m, 3H); 5.65 (d, J=7, 2H); 7.31–7.47 (m, 5H); 9.68 (s, 1H); 9.82 (d, J=7, 1H).

(b) 7β-[D-2-(4-Ethyl-2,3-dioxopiperazin-1-ylcarbonylamino)-2-phenylacetamido]-7α-hydroxyamino-3-[(1-potassiumsulphomethyl-1H-tetrazol-5-yl)thiomethyl]ceph-3-em-4-carboxylate, triethylammonium salt The title compound (124 mg) was prepared from the 7α-methylthiocephem (from Example 36(a)) (200 mg) by the method described in Example 9(b) except that two equivalents each of hydroxylamine hydrochloride and triethylamine were used.

IR (KBr) 1775 cm$^{-1}$.

N.M.R. (DMSO-D$_6$) δ=1.09 (t, J=7, 3H); 1.20 (t, J=7, 9H); 3.09 (q, J=7, 6H); 3.19–3.63 (m, 6H)); 3.91 (m, 2H); 4.03 and 4.43 (ABq, J=13, 2H); 4.97–5.06 (m, 3H); 5.68 (d, J=7, 1H); 7.29–7.48 (m, 5H); 8.16 (broad, 1H); 9.56 (s, 1H); 9.88 (d, J=7, 1H).

EXAMPLE 37

7β-[2-(R)-(4-ethyl-2,3-dioxopiperazin-1-ylcarbonylamino)-3-(S)-methoxybutanamido]-7α-hydroxyamino-3-[1-potassiumsulphomethyltetrazol-5-yl)thiomethyl]ceph-3-em-4-carboxylic acid (a) 7β-[2-(R)-(4-ethyl-2,3-dioxopiperazin-1-ylcarbonylamino)-3-(S)-methoxybutanamido]-3-[(1-potassiumsulphomethyltetrazol-5-yl)thiomethyl]-7α-methylthioceph-3-em-4-carboxylic acid 7β-[2-(R)-(4-ethyl-2,3-dioxopiperazin-1-ylcarbonylamino)-3-(S)-methoxybutamamido]-7α-methylthiocephalosporanic acid was converted to the title compound using the method of Example 36(a) using appropriate starting materials.

I.R. 1780 cm$^{-1}$.

N.M.R. 300 MHz (dmso) δ=1.05–1.17 (m, 6H); 2.24 (s, 3H); 3.1–3.92 (m, 9H); 3.25 (s, 3H); 4.08 and 4.43 (ABq, 2H, J=7 Hz); 4.4–4.5 (m, 1H); 4.95-5.02 (m, 3H); 9.23 (d, 1H, J=6 Hz); 9.27 (s, 1H).

(b) 7β-[2-(R)-(4-Ethyl-2,3-dioxopiperazin-1-ylcarbonylamino)-3-(S)-methoxybutanamido]-7α-hydroxyamino-3-[(1-potassiumsulphomethyltetrazol-5-yl)-thiomethyl]ceph-3-em-4-carboxylic acid The 7α-methylthiocephalosporin from part (a) was converted to the title compound using the method of Example 9(b).

I.R. 1780 cm$^{-1}$.

N.M.R. 300 MHz (dmso), δ=1–1.1 (m, 6H); 3–3.95 (m, 9H); 3.24 (s, 3H); 4.06 and 4.38 (ABq, 2H, J=8 Hz); 4.42–4.5 (m, 1H); 4.9–5.04 (m, 3H); 9.02 (s, H); 9.24 (d, 1H, J=6 Hz).

EXAMPLE 38

7β-[D-2-Ureido-2-phenylacetamido]-7α-hydroxyaminocephalosporanic acid (a) Benzhydryl 7β-[D-2-ureido-2-phenylacetamido]-7α-methylthiocephalosporanate D-2-Amino-4-phenyl-5(4H)-oxazolone hydrochloride was prepared from D-phenyl glycine using the general method described by Breuer et al in *J. Antibiotics*, 31 (6), 546, (1978).

IR (nujol) 1870, 1720 br. cm$^{-1}$.

The oxazolone hydrochloride (2.12 g) was added to a cold (−60°) solution of benzhydryl 7β-amino-7α-methylthiocephalosporanate (1.94 g) and propylene oxide (3.5 ml) in dichloromethane (20 ml) and dimethylformamide (20 ml). Aftr stirring for 3 hours at this temperature the suspension was warmed to −20° over 0.5 hours giving a clear solution. Ethyl acetate (100 ml) and water (100 ml) were added, the aqueous layer separated and re-extracted with ethyl acetate (50 ml). The combined organic extracts were washed with 5% aqueous sodium bicarbonate (50 ml), 0.01M hydrochloric acid (50 ml) and dried over sodium sulphate. Evaporation of the solvent under vacuum gave a yellow oil which was purified by silica-gel chromatography (dichloromethane-ethylacetate gradient) to give the title compound as a white solid after trituration with dichloromethane (25 ml). (1.08 g).

IR (KBr) 1780 cm$^{-1}$.

(b) Benzhydryl 7β-[D-2-ureido-2-phenylacetamido]-7α-hydroxyaminocephalosporanate The 7α-methylthiocephem (from Example 38(a)) (330 mg) in dimethylformamide (5 ml) was cooled to −55° and treated with a solution of mercuric acetate (159 mg) in dimethylformamide (1 ml), followed by hydroxylamine hydrochloride (38 mg) in dimethylformamide (1 ml). The solution was warmed to 0° over 1 hour with stirring then added to ethyl acetate (50 ml) and water (25 ml). The organic phase was washed with water (2×25 ml), dried and evaporated under vacuum. The crude product obtained was purified by silica-gel chromatography (dichloromethane-ethyl acetate gradient) to give the title compound (225 mg).

IR 1775 cm$^{-1}$.

(c) 7β-[D-2-Ureido-2-phenylacetamido]-7α-hydroxyaminocephalosporanic acid

The benzhydryl ester (from Example 38(b)) (220 mg) in dichloromethane (5 ml) containing anisole (220 mg) was pre-cooled to −65° and treated with a solution of aluminium chloride (136 mg) in nitromethane (1 ml). The resulting dark brown suspension was stirred for 10 minutes at this temperature then added to saturated aqueous sodium bicarbonate (15 ml) and ethyl acetate (25 ml). After filtration, the aqueous layer was separated and acidified to pH 2 with concentrated hydrochloric acid. Extraction with ethyl acetate (3×25 ml), followed by drying evaporation of the solvent and trituration with dichloromethane gave the title compound as a white solid (52 mg).

IR (KBr) 1770 cm$^{-1}$.

N.M.R. (DMSO-D$_6$) δ=2.13 (s, 3H); 3.32 and 3.62 (ABq, J=17, 2H); 4.70 and 4.98 (ABq, J=13, 2H); 5.17 (s, 1H); 5.64 (d, J=7, 1H); 5.82 (s, NH$_2$); 6.61 (s, 1H); 6.91 (d, J=7, NH), 7.30–7.63 (m, 5H); 8.27 (s, 1H); 9.48 (s, 1H); 13.78 (brs, 1H).

EXAMPLE 39

7β-[D-2-(4-Ethyl-2,3-dioxopiperazin-1-ylcarbonylamino)-2-phenylacetamido]-7α-hydroxyamino-3-[(5-methyl-1,3,4-thiadiazol-2-yl)thiomethyl]ceph-3-em-4-carboxylic acid (a) 7β-[D-2-(4-ethyl-2,3-dioxopiperazin-1-ylcarbonylamino)-2-phenylacetamido]-3-[(2-methyl-1,3,4-thiadiazol-5-yl)thiomethyl]-7α-methylthioceph-3-em-4-carboxylic acid A solution of 7β-[D-2-(4-ethyl-2,3-dioxopiperazin-1-ylcarbonylamino)-2-phenylacetamido]-7α-methylthiocephalosporanic acid (Example 6(a)) (0.50 g) and 5-mercapto-2-methyl-1,3,4-thiadiazole (0.20 g) in 1,2-dichloroethane (50 ml) was refluxed under nitrogen for 4 hours. The mixture was cooled and a little insoluble material filtered off. The filtrate was evaporated to dryness and the residue partitioned between ethyl acetate (50 ml) and saturated sodium bicarbonate solution (50 ml). The saturated sodium bicarbonate layer was washed with ethyl acetate (2×25 ml) and acidified to pH 2 with concentrated hydrochloric acid. The aqueous phase was extracted with ethyl acetate (2×50 ml) washed with brine and dried over sodium sulphate to yield on evaporation a yellow solid (0.42 g).

I.R. (KBr) 1780 cm$^{-1}$.

N.M.R. (acetone D$_6$) δ=1.17 (t, J=7, 3H); 2.26 (s, 3H); 2.7 (s, 3H); 3.2–3.85 (m, 6H); 3.85–4.16 (m, 2H); 4.18 and 4.62 (2H, ABq. J=13); 4.92 (s, 1H); 5.7 (d, J=7, 1H); 7.15–7.8 (m, 5H); 8.45 (s, 1H); 9.84 (d, J=7, NH).

(b) Benzhydryl 7β-[D-2-(4-ethyl-2,3-dioxopiperazin-1-ylcarbonylamino)-2-phenylacetamido]-3-[(2-methyl-1,3,4-thiadiazol-5-yl)thiomethyl]-7α-methylthioceph-3-em-4-carboxylate To a solution of 7β-[D-2-(4-ethyl-2,3-dioxopiperazin-1-ylcarbonylamino)-2-phenylacetamido]-3-[(2-methyl-1,3,4-thiadiazol-5-yl)thiomethyl]-7α-methylthioceph-3-em-4-carboxylic acid (0.42 g) in dichloromethane (20 ml) at room temperature was added excess diphenyldiazomethane with stirring. After 0.5 hour the resulting pale pink solution was evaporated to yield a yellow foam (0.16 g).

I.R. (KBr) 1780 cm$^{-1}$.

N.M.R. (DMSO-D$_6$) δ=1.14 (t, J=6, 3H); 2.18 (s, 3H); 2.6 (s, 3H); 3.2–3.55 (m, 6H); 3.80–4.20 (m, 2H); 4.22 and 4.6 (2H, ABq J=13); 4.85 (s, 1H); 5.64 (d, J=7, 1H); 6.8 (s, 1H); 7.1–7.55 (m, 15H); 9.85 (d, J=7, NH).

(c) Benzhydryl 7β-[D-2-(4-ethyl-2,3-dioxopiperazin-1-ylcarbonylamino)-2-phenyl-acetamido]-7α-hydroxyamino-3-[(2-methyl-1,3,4-thiadiazol-5-yl)thiomethyl]-ceph-3-em-4-carboxylate To a solution of benzhydryl 7β-[D-2-(4-ethyl-2,3-dioxopiperazin-1-ylcarbonylamino)-2-phenyl-acetamido]-3-[(2-methyl-1,3,4-thiadiazol-5-yl)thiomethyl]-7α-methylthioceph-3-em-4-carboxylate (0.276 g) in DMF (20 ml) at −60° C. under nitrogen was added a solution of mercuric acetate (0.103 g) in dimethylformamide (5 ml) with stirring. After 5 minutes a solution of hydroxylamine hydrochloride (0.023 g) in dimethylformamide (2 ml) was added and the mixture stirred to 0° over 1 hour. Water (50 ml) and ethylacetate (50 ml) were added and stirring continued for 15 minutes. The mixture was filtered and the ethyl acetate layer separated, washed with brine and dried over sodium sulphate and evaporated to yield a yellow oil. Re-evaporation from dichloroethane gave the product as a white foam (0.26 g).

I.R. (KBr) 1780 cm$^{-1}$.

N.M.R. (CDCl$_3$) δ=1.23 (t, J=7, 3H); 2.62 (s, 3H); 2.9–3.64 (m, 6H); 3.75–3.95 (m, 2H); 4.28 and 4.52 (2H, ABq J=13); 5.22 (s, 1H); 5.5 (d, J=7, 1H); 6.45 (brs, H); 6.8 (s, 1H); 7.0–7.55 (m, 15H); 8.4 (brs, 1H); 9.82 (d, J=7, NH).

(d) 7β-[D-2-(4-ethyl-2,3-dioxopiperazin-1-ylcarbonylamino)-2-phenyl acetamido]-7α-hydroxyamino-3-[(2-methyl-1,3,4-thiadiazol-5-yl)thiomethyl]ceph-3-em-4-carboxylic acid To a solution of benzhydryl 7β-[D-2-(4-ethyl-2,3-dioxopiperazin-1-ylcarbonylamino)-2-phenyl-acetamido]-7α-hydroxyamino-3-[(2-methyl-1,3,4-thiadiazol-5-yl)thiomethyl]ceph-3-em-4-carboxylate (0.260 g) in dichloromethane (5 ml) at −70° C. under nitrogen was added anisole (0.20 g) followed by a solution of aluminium chloride (0.124 g) in nitromethane (2 ml) with stirring. After 5 minutes, ethyl acetate (40 ml) and saturated sodium bicarbonate solution (40 ml) were added and stirring continued at 0° for 15 minutes. After filtration through "Hyflo" the sodium bicarbonate layer was separated and washed with ethyl acetate (20 ml)

and acidified to pH 2 with concentrated hydrochloric acid. The aqueous layer was extracted with ethyl acetate (3×20 ml), and the combined extracts were washed with brine and dried over sodium sulphate. Evaporation yielded the product as a white solid (66 mg).

I.R. (KBr) 1780 cm$^{-1}$.

N.M.R. (DMSO-D$_6$) δ=1.1 (t, J=7, 3H); 2.7 (s, 3H); 3.2–3.65 (m, 6H); 3.85–3.95 (m, 2H); 4.15 and 4.5 (2H, ABq J=13); 5.05 (s, 1H); 5.70 (d, J=7, 1H); 6.51 (brs, 1H); 7.28–7.52 (m, 5H); 8.18 (s, 1H); 9.56 (s, NH); 9.90 (d, J=7, NH).

EXAMPLE 40

7α-Hydroxyamino-7β-[DL-2-(2-methyl-4-hydroxypyrid-5-ylcarbonylamino)-2-phenylacetamido]cephalosporanic acid (a) Benzhydryl 7β-[DL-2-(2-methyl-4-hydroxypyrid-5-ylcarbonylamino)-2-phenylacetamido]-7α-methylthiocephalosporanate Benzhydryl 7β-amino-7α-methylthiocephalosporanate (507 mg) in dichloromethane (30 ml) was cooled to −10° C. and treated dropwise during 1 minutes with a solution of D-2-[2-methyl-4-hydroxypyrid-5-ylcarbonylamino]-2-phenylacetyl chloride (333 mg) in dichloromethane (10 ml). Pyridine (85 μl) was added during 1 minute and the solution was stirred at −10° C. for 1 hour, then washed with 1% hydrochloric acid (50 ml), saturated sodium bicarbonate (50 ml) and dried (MgSO$_4$). The solvent was removed under vacuum and the residue was chromatographed on silica gel, eluting with methanol/ethylacetate 1:9 to give the title compound (130 mg).

I.R. (KBr) 1780 cm$^{-1}$.

N.M.R. (DMSO-D$_6$) δ=2.02 (s, 3H); 2.08 (s, 3H); 2.18 (s, 3H); 3.2–3.4 (m, 2H); 4.62–5.14 (m, 3H); 5.72 (d, J=6, 1H); 6.13 (s, 1H); 6.85 (s, 1H); 7.15–7.75 (m, 15H); 8.38 (d, J=6, 1H); 10.86 (s, 1H); 11.43 (d, J=6, 1H).

(b) 7β-[DL-2-(2-Methyl-4-hydroxypyrid-5-ylcarbonylamino)-2-phenylacetamido]-7α-methylthiocephalosporanic acid was prepared from the product of Example 40a by the method described in Example 39(d).

I.R. (KBr) 1776 cm$^{-1}$.

N.M.R. (DMSO-D$_6$) δ=2.05 and 2.06 (2×s, 3H); 2.22 and 2.26 (2×s, 3H); 3.2–3.8 (m, 2H); 4.6–5.05 (m, 2H); 5.05 and 5.06 (2×s, 1H); 5.82+5.9 (2×d, J=7 Hz, 1H); 6.27 (s, 1H); 7.22–7.53 (m, 5H); 8.22–8.32 (m, 1H); 9.6–9.65 (m, 1H); 11.18 and 11.21 (2×d, J=7 Hz, 1H); 12.18 (s, 1H); 13.75 (brs, 1H).

(c) 7α-Hydroxyamino-7β-[DL-2-(2-methyl-4-hydroxypyrid-5-ylcarbonylamino)-2-phenylacetamido]cephalosporanic acid The title compound (88 mg) was prepared from the 7α-methylthiocephem (Example 40(b)) (100 mg) by the method previously described in Example 9(b).

I.R. (KBr) 1770 cm$^{-1}$.

N.M.R. (DMSO-D$_6$) δ=2.02 (s, 3H); 2.28 (s, 3H); 3.16–3.58 (m, 2H); 4.58–4.95 (m, 2H); 5.0 and 5.06 (2×s, 1H, 6-H); 5.9 and 5.98 (2×d, J=7 Hz, 1H); 6.27 and 6.4 (2×s, 1H); 7.22–7.56 (m, 5H); 8.06 and 8.13 (2×s, 1H); 8.27 and 8.29 (2×s, 1H); 9.29 and 9.45 (2×s, 1H); 11.18–11.35 (m, 1H); 12.43 (brs, 1H).

EXAMPLES 41 AND 42

These compounds of the formula (I) were prepared from the appropriate starting materials using the method described in Example 40 parts (a) to (c).

| Example No. and side chain stereochemistry | R | R$^1$ | R$^2$ | I.R. (KBr) cm$^{-1}$ | N.M.R. (DMSO—d$_6$) |
|---|---|---|---|---|---|
| 41 DL— | thienyl-methyl | −C(=O)−N(piperazinedione)N−Et | −CH$_2$OAc | 1778 | δ = 1.09 (m, 2H); 2.04 and 2.06 (2 × s, 3H, D and L OCOC$\underline{H}_3$); 3.18 to 3.54 (m, 6H); 3.86 to 3.98 (m, 2H); 4.58 to 5.02 (m, 2H); 5.08 to 5.14 (2 × s, 1H, D and L C6$\underline{H}$); 5.95 to 6.00 (m, 1H); 6.96 to 7.54 (m, 3H); 8.15 and 8.22 (2 × s, 1H, D and L forms); 9.55 and 9.58 (2 × s, 1H); D and L forms); 9.75 to 9.84 (m, 1H). |
| 42 DL— | methylthienyl | −C(=O)−N(piperazinedione)N−Et | −CH$_2$OAc | 1784 | δ = 1.11 (m, 3H); 2.05 and 2.06 (2 × s, 3H, D and L forms); 3.25 to 3.70 (m, 6H); 3.92 (m, 2H); 4.61 to 4.98 (m, 2H); 5.06 and 5.09 (2 × s, 1H, DL forms); 5.68 (m, 1H); 7.11 (m, 1H); 7.48 (m, 2H); 7.96 (s, 1H); 9.46 and 9.54 (2 × s, 1H, DL forms); 9.76 (m, 1H). |

EXAMPLE 43

7β-[D-2-(4-Ethyl-2,3-dioxopiperazin-1-ylcarbonylamino)-2-phenylacetamido]-7α-hydroxyamino-3-[(1-(2-potassium sulphoxyethyl)-1H-tetrazol-5-yl)-thiomethyl]ceph-3-em-4-carboxylic acid

[2-Potassiumsulphoxyethyl=—(CH$_2$)$_2$OSO$_2$O$^\ominus$K$^\oplus$]

(a) 7β-[D-2-(4-Ethyl-2,3-dioxopiperazin-1-ylcarbonylamino)-2-phenylacetamido]-7α-methylthio-3-[(1-(2-potassium sulphoxyethyl)-1H-tetrazol-5-yl)thiomethyl]ceph-3-em-4-carboxylic acid A solution of 7β-[D-2-(4-ethyl-2,3-dioxopiperazin-1-ylcarbonylamino)-2-phenylacetamido]-3-[(1-(2-hydroxyethyl)-1H-tetrazol-5-yl)-thiomethyl]-7α-methylthioceph-3-em-4-carboxylic acid (Example 16(a)) (300 mg) stirred under nitrogen at 0° C. was treated with a solution of dimethylformamide-sulphur trioxide complex (prepared from trimethylsilylchlorosulphonate and dimethylformamide) (1.5 ml). The temperature was stirred for 20 minutes, poured into a 0.5N solution of potassium dihydrogen orthophosphate (50 ml) and the solution extracted with methylene chloride (2×50 ml). The aqueous phase was treated with tetrabutylammonium hydrogen sulphate (289 mg) and extracted with methylene chloride (2×50 ml). The extract was washed with 0.5N potassium dihydrogen orthophosphate solution (50 ml), dried over magnesium sulphate, filtered and evaporated to dryness under vacuum. The oily residue was taken up in acetone (20 ml) and a solution of potassium nonafluorobutane sulphonate (288 mg) in acetone (10 ml) added in a dropwise manner to give a white precipitate. Diethyl ether (100 ml) was added to give further precipitate which was separated by filtration and dried under vacuum to give the title compound (270 mg).

I.R. (KBr) 1778 cm$^{-1}$.

N.M.R. (DMSO-D$_6$) δ=1.08 (t, J=7, 3H); 2.22 (s, 3H); 3.20–3.75 (m, 6H); 3.93 (m, 2H); 4.13 (m, 3H); 4.47 (m, 3H); 5.03 (s, 1H); 5.66 (d, J=7, 1H); 7.30–7.55 (m, 5H); 9.77 (s, 1H); 9.85 (d, J=7, 1H).

(b) 7β-[D-2-(4-Ethyl-2,3-dioxopiperazin-1-ylcarbonylamino)-2-phenylacetamido]-7α-hydroxyamino-3-[(1-(2-potassiumsulphoxyethyl)-1H-tetrazol-5-yl)thiomethyl]ceph-3-em-4-carboxylic acid The title compound (19 mg) was prepared from the 7α-methylthiocephem (Example 43(a)) (260 mg) by the method previously described in Example 9(b).

I.R. (KBr) 1780 cm$^{-1}$.

N.M.R. (DMSO-D$_6$) δ=1.09 (t, J=7, 3H); 3.23–3.66 (m, 6H); 3.92 (m, 2H); 4.12 (m, 3H); 4.51 (m, 3H); 5.01 (s, 1H); 5.72 (d, J=7, 1H); 7.27–7.55 (m, 5H); 9.60 (s, 1H); 9.89 (d, J=7, 1H).

EXAMPLE 44

7β-[2-(R)-(4-Ethyl-2,3-dioxopiperazin-1-ylcarbonylamino)-3-(S)-(potassium sulphoxy)-butanamido]-7α-hydroxyaminocephalosporanic acid (a) 7β-[2-(R)-(4-Ethyl-2,3-dioxopiperazin-1-ylcarbonylamino)-3-(S)-(potassium sulphoxy)-butanamido]-7α-methylthiocephalosporanic acid The title compound (195 mg) was prepared from 7β-[2-(R)-(4-ethyl-2,3-dioxopiperazin-1-ylcarbonylamino)-3-(S)-hydroxybutanamido]-7α-methylthiocephalosporanic acid (330 mg) and dimethylformamide-sulphur trioxide complex by the method of Example 43(a).

I.R. (KBr) 1780 cm$^{-1}$.

N.M.R. (DMSO d$_6$) δ=1.06 (t, 3H, J=4.5); 1.18 (d, 3H, J=6); 2.00 (s, 3H); 2.29 (s, 3H); 3.2–3.4 (m, 4H); 3.54 (m, 2H); 3.90 (m, 2H); 4.38 (m, 1H); 4.64 and 4.98 (ABq, 2H, J=15); 4.80 (m, 1H); 5.01 (s, 1H); 9.11 (s, 1H); 9.24 (d, 1H, J=6).

(b) 7β-[2-(R)-(4-Ethyl-2,3-dioxopiperazin-1-ylcarbonylamino)-3-(S)-(potassium sulphoxy)-butanamido]-7α-hydroxyaminocephalosporanic acid The title compound (115 mg) was prepared from the 7α-methylthiocephem of Example 44(a) (182 mg) by the method of Example 9(b).

I.R. (KBr) 1780 cm$^{-1}$.

N.M.R. (DMSO d$_6$) δ=1.06 (t, 3H, J=4.5); 1.18 (d, 3H, J=6); 2.01 (s, 3H); 3.21 to 3.63 (6H); 3.91 (m, 2H); 4.39 (m, 1H); 4.65 and 4.97 (ABq, 2H, J=15); 4.68 (m, 1H); 5.06 (s, 1H); 8.83 (s, 1H); 9.23 (d, 1H, J=6).

EXAMPLE 45

3-Acetoxymethyl-7β-[DL-2-(4-ethyl-2,3-dioxopiperazin-1-ylcarbonylamino)-2-(4-hydroxyphenyl)acetamido]-7α-hydroxyaminoceph-3-em-4-carboxylic acid sodium salt (a) Benzhydryl 3-acetoxymethyl-7β-[DL-2-(4-benzyloxycarbonyloxyphenyl)-2-(4-ethyl-2,3-dioxopiperazin-1-ylcarbonylamino)acetamido]-7α-methylthioceph-3-em-4-carboxylate D-2-(4-Benzyloxycarbonyloxyphenyl)-2-(4-ethyl-2,3-dioxopiperazin-1-ylcarbonylamino)acetic acid (1.25 g) in dichloromethane (20 ml) was treated with oxalyl chloride (1.36 g) followed after 5 minutes by dimethylformamide (1 drop). After stirring at room temperature for 1 hour the solution was evaporated to dryness, the residue was dissolved in a mixture of dichloromethane and carbon tetrachloride and re-evaporated. The resulting acid chloride in dichloromethane (5 ml) was added dropwise over 2 minutes to a pre-cooled (−60°) solution of benzhydryl 7β-amino-7α-methylthiocephalosporanate (1.3 g) and propylene oxide (3 ml) in dichloromethane (20 ml). After 1 hour at −60° the solution was brought to 20° over 2 hours then allowed to stand for 18 hours at room temperature. Ethyl acetate (100 ml) was added and the solution washed with 5% aqueous sodium bicarbonate (20 ml), followed by 0.01M hydrochloric acid (50 ml) and finally dried over sodium sulphate. Evaporation of the solvent gave the crude product which after chromatography on silica gel (eluting with a dichloromethane-ethyl acetate gradient), afforded the title compound (1.1 g).

I.R. (KBr) 1780 cm$^{-1}$.

N.M.R. (CDCl$_3$) δ=1.21 (t, J=7, 3H); 2.02, 2.04, 2.07 and 2.26 (4×s, 6H, SCH$_3$ and OCOCH$_3$); 3.18–3.63 (m, 6H); 3.93–4.16 (m, 2H); 4.86 and 5.12, 4.89 and 5.12 (2×ABq, J=14, 2H); 4.89 and 4.92 (2×s, 1H); 5.26 and 5.27 (2×s, 2H); 5.50–5.58 (m, 1H), 6.57 and 6.66 (2×s, NH); 6.88 (s, 1H); 7.15–7.56 (m, 19H); 9.98 (d, J=7, NH).

(b) Benzhydryl 3-acetoxymethyl-7β-[DL-2-(4-benzyloxycarbonyloxyphenyl)-2-(4-ethyl-2,3-dioxopiperazin-1-ylcarbonylamino)acetamido]-7α-hydroxyaminoceph-3-em-4-carboxylate This compound was prepared from the 7α-methylthiocephem (Example 45(a)) (1.1 g) by the method described for Example 38(b). Silica gel chromatography (eluting with dichloromethane-ethyl acetate) gave the title compound as a white solid (0.95 g).

I.R. (KBr) 1775 cm$^{-1}$.

N.M.R. (CDCl$_3$) δ=1.07–1.22 (m, 3H); 1.97 (s, 3H); 2.68 and 3.07 (2H, ABq, J=14); 3.27–3.63 (m, 4H); 3.78–4.14 (m, 2H); 4.80–5.35 (m, CH$_2$OAc, OCH$_2$Ph, C$_6$-H and 1H exch.); 5.53–5.65 (m, CHNH); 6.85–7.65; (m, 19H); 8.02 (s, NH); 8.15 and 8.80 (2 brs, 1H exch.); 10.08 (d, J=7, NH).

(c) 3-Acetoxymethyl-7β-[DL-2-(4-benzyloxycarbonyloxyphenyl)-2-(4-ethyl-2,3-dioxopiperazin-1-ylcarbonylamino)acetamido]-7α-hydroxyaminoceph-3-em-4-carboxylic acid The benzhydryl ester (0.95 g) obtained in the previous stage was treated with aluminum chloride-anisole as described for Example 38(c). The crude product was triturated with diethylether (15 ml) to afford the title compound (545 mg).

I.R. (KBr) 1765 cm$^{-1}$.

N.M.R. (DMSO-d$_6$) δ=1.09 (t, J=7, 3H); 2.02 and 2.04 (2×s, OCOCH$_3$); 3.08–3.66 (m, 6H); 3.84–4.00 (m, 2H); 4.63 and 4.92, 4.67 and 4.95 (2H, 2 ABq, J=14); 5.05 and 5.11 (2×s, C$_6$-H); 5.29 (s, CH$_2$Ph); 5.73 (d, J=7, CHNH)); 6.55 (brs, 1H); 7.23–7.62 (m, 9H); 8.11 and 8.21 (2×s, 1H); 9.52 and 9.58 (2×s, 1H); 9.88 and 9.93 (2d, J=7, NHCH).

(d) 3-Acetoxymethyl-7β-[DL-2-(4-ethyl-2,3-dioxopiperazin-1-ylcarbonylamino)-2-(4-hydroxyphenyl- )acetamido]-7α-hydroxyaminoceph-3-em-4-carboxylic acid, sodium salt The cephalosporanic acid (300 mg) from the previous example was stirred in a solution of sodium hydrogen carbonate (33.6 mg) in water (15 ml) until dissolved. 10% Palladium on carbon (100 mg) was added and the mixture shaken under 10 p.s.i. of hydrogen at room temperature for 0.5 hours. Filtration, followed by lyophilisation gave the title compound as an amorphous solid (215 mg).

I.R. (KBr) 1765 cm$^{-1}$.

N.M.R. (D$_2$O) δ=1.21 (t, J=7, 3H); 2.08 and 2.11 (2×s, OCOCH$_3$); 3.10-3.82 (m, C$_2$-2H, CH$_2$CH$_3$ and piperazine CH$_2$); 3.92-4.15 (m, piperazine CH$_2$); 4.62-5.15 (m, CH$_2$OAc and C$_6$-H); 5.43 and 5.47 (2×s, CHNH); 6.85-7.50 (m, 4H).

EXAMPLE 46

7β-[2-(R)-(4-Ethyl-2,3-dioxopiperazin-1-ylcarbonylamino)-3-(S)-hydroxybutanamido]-7α-hydroxyaminocephalosporanic acid (a) Benzhydryl 7β-[2-(R)-(4-ethyl-2,3-dioxopiperazin-1-ylcarbonylamino)-3-(S)-hydroxybutanamido]-7α-methylthiocephalosporanate 2-(R)-(4-Ethyl-2,3-dioxopiperazin-1-ylcarbonylamino)-3-(S)-hydroxybutyric acid (11.4 g) was suspended in CH$_2$Cl$_2$ (120 cm$^3$) and N-methylpiperidine (3.93 g) was added thereto to convert the suspension to a solution. The solution was cooled to −20° C. under nitrogen and ethyl chloroformate (4.2 g) was added. The mixture was stirred for 30 minutes and a solution of benzhydryl 7β-amino-7α-methylthiocephalosporanate (19.2 g) in methylene chloride (30 cm$^3$) was added. The mixture was allowed to attain room temperature, stirred for 64 hours, washed with 0.2N hydrochloric acid (2×50 cm$^3$) and saturated sodium bicarbonate solution (2×50 cm$^3$), dried over magnesium sulphate and evaporated to dryness. The residue was purified by a column chromatography (silica gel, eluted with 5% methanol in ethyl acetate) to give the title compound, (15.8 g).

I.R. (KBr disc) 1783 cm$^{-1}$, 1737 cm$^{-1}$, 1715 cm$^{-1}$, 1688 cm$^{-1}$.

N.M.R. (DMSO) δ=1.13 (t, 3H, J=7); 1.30 (d, 3H, J=6); 2.05 (s, 3H); 2.35 (s, 3H); 3.46 (m, 6H); 4.10 (m, 2H); 4.47 (m, 2H); 4.93 and 5.15 (ABq, 2H, J=12); 4.96 (s, 1H); 6.89 (s, 1H); 7.27-7.48 (m, 10H); 7.99 (s, 1H); 9.58 (d, 1H, J=9).

(b) 7β-[2-(R)-(4-Ethyl-2,3-dioxopiperazin-1-ylcarbonylamino)-3-(S)-hydroxybutanamido]-7α-methylthiocephalosporanic acid The title compound (2.5 g) was prepared from the product of Example 46(a) (5.0 g) using the method of Example 39(d).

I.R. (KBr disc) 1778 cm$^{-1}$, 1711 cm$^{-1}$, 1675 cm$^{-1}$.

N.M.R. (DMSO d$_6$) δ=1.07 (m, 6H); 2.00 (s, 3H); 2.25 (s, 3H); 3.33 to 3.61 (m, 6H); 3.90 (m, 3H); 4.33 (m, 1H); 4.64 and 4.94 (ABq, 2H, J=13); 5.05 (s, 1H); 5.07 (d, 1H, J=6); 9.15 (s, 1H); 9.26 (d, 1H, J=6).

(c) 7β-[2-(R)-(4-Ethyl-2,3-dioxo-1-piperazin-1-ylcarbonylamino)-3-(S)-hydroxybutanamido]-7α-hydroxyaminocephalosporanic acid The 7α-methylthiocephem (from Example 46(b) (250 mg) was converted to the title compound (142 mg) by the method of Example 9(b).

I.R. (KBr) 1776 cm$^{-1}$.

N.M.R. (dmso d$_6$) δ=1.10 (m, 6H); 2.07 (s, 3H); 3.2-4.2 (m, 9H); 4.35 (m, 1H); 4.61 and 4.90 (ABq, 2H, J=10); 5.10 (s, 1H); 8.91 (s, 1H); 9.30 (d, 1H, J=7).

EXAMPLE 47

7α-Hydroxyamino-7B-(D-2-[2-oxoimidazolidin-1-ylcarbonylamino]-2-phenylacetamido)cephalosporanic acid (a) Diphenylmethyl 7α-methylthio-7B-[D-2-(2-oxoimidazolidin-1-ylcarbonylamino)-2-phenylacetamido]cephalosporanate Diphenylmethyl 7β-amino-7α-methylthiocephalosporanate (0.48 g) in dry dichloromethane (5 ml) was cooled to −20° C. and treated over one minute with a solution of D-2-(2-oxoimidazolidin-1-ylcarbonylamino)-2-phenylacetylchloride (0.26 g) in dry dichloromethane (2 ml). Pyridine (80 μl) was added over 1 minute and the reaction was then allowed to warm to +10° C. over 30 minutes. The solution was then washed with 1% hydrochloric acid (20 ml), saturated sodium bicarbonate (20 ml) and dried (MgSO$_4$). The solvent was removed in vacuo and the residue was chromatogdraphed (silica gel, dichloromethane:ethyl acetate, 7:3) to give the title compound, (0.37 g).

I.R. (CH$_2$Cl$_2$ soln) 1780 cm$^{-1}$.

N.M.R. (CHCl$_3$) δ=1.98 (s, 3H); 2.28 (s, 3H); 3.4-3.6 (m, 4H); 3.9-4.1 (m, 2H); 4.95-5.15 (ABq, J=13 Hz, 2H); 5.2 (s, 1H); 6.9 (s, 1H); 7.2-7.6 (m, 15H); 9.1 (tr, 1H).

(b) Diphenylmethyl 7α-hydroxyamino-7β-[D-2-(2-oxoimidazolidin-1-ylcarbonylamino)-2-phenylacetamido]cephalosporanate Diphenylmethyl 7α-methylthio-β-[D-2-(2-oxoimidazolidin-1-yl)carbonylamino)-2-phenylacetamido]cephalosporanate (0.37 g) was dissolved in dry DMF (5 ml), cooled to −50° C. under nitrogen and treated successively with a solution of mercuric acetate (170 μg) in DMF (1 ml) followed by hydroxylamine hydrochloride in DMF (1 ml). The mixture was allowed to warm to 0° C. over 1.5 hours and then added to ethyl acetate (50 ml). The solution was washed with water (5×50 ml) dried and evaporated in vacuo. The residue was chromatographed (silica gel/dichloromethane:ethyl acetate, 6:4) to give the title compound, (0.31 g).

I.R. (CH$_2$Cl$_2$ solution) 1790 cm$^{-1}$.

N.M.R. (CDCl$_3$) δ=2.03 (s, 3H); 2.75 and 2.98 (ABq, J=16, 2H); 3.5 (m, 2H); 3.8-4.1 (m, 2H); 4.85-5.1 (m, 2H); 5.4 (s, 1H); 5.6 (s, 1H exch.); 5.7 (d, J=6, 1H); 6.2 (s, 1H exch.); 6.9 (s, 1H); 7.1-7.6 (m, 15H); 8.7 (s, 1H exch.); 9.3 (d, J=6, 1H).

(c) 7α-Hydroxyamino-7β-[D-2-(2-oxoimidazolidin-1-ylcarbonylamino)-2-phenylacetamido]cephalosporanic acid was prepared from the product of Example 47(b) (85 mg) by the method of Example 38(c).

I.R. (KBr) 1780 cm$^{-1}$.

N.M.R. (DMSO d$_6$) δ=2.07 (s, 3H); 3.18 and 3.45 (ABq, J=16 Hz, 2H); 3.3 (m, 2H); 3.7 (m, 2H); 4.57 and 4.86 (Abq, 2H, J=12); 5.0 (s, 1H); 5.62 (d, J=6, 1H); 6.5 (s, 1H); 7.2-7.6 (m, 5H); 8.15 (s, 1H); 9.10 (d, J=6, 1H); 9.45 (s, 1H).

EXAMPLE 48

7β-[DL-2-(4-Benzyloxycarbonyloxyphenyl)-2-(4-ethyl-2,3-dioxopiperazin-1-ylcarbonylamino)acetamido]-7α-hydroxyamino-3-[(1-methyl-1H-tetrazol-5-yl)thiomethyl]ceph-3-em-4-carboxylic acid (a) 3-Acetoxymethyl-7β-[DL-2-(4-Benzyloxycarbonyloxyphenyl)-2-(4-ethyl-2,3-dioxopiperazin-1-ylcarbonylamino)acetamido]-7α-methylthioceph-3-em-4-carboxylic acid The benzhydryl ester (from Example 45a)) (4.67 g) was treated with aluminium chloride and anisole as described previously for Example 39(d), giving the title compound (3.1 g) as a white solid.

I.R. (KBr) 1780 cm$^{-1}$.

N.M.R. (DMSO-d$_6$) δ=1.07 (t, J=7, 3H); 1.89, 2.01, 2.03 and 2.21 (4×s, 6H, SCH$_3$ and OCOCH$_3$); 3.22–3.64 (m, 6H); 3.87–3.91 (m, 2H); 4.64 and 4.95, 4.67 and 5.00 (2×ABq, J=13, 2H); 5.09 (s, 1H); 5.27 (s, 2H); 5.66 (d, J=7, 1H); 7.23–7.51 (m, 9H); 9.74 (s, 1H); 9.85 and 9.92 (2×d, J=7, 1H).

(b) 7β-[DL-2-(4-Benzyloxycarbonyloxyphenyl)-2-(4-ethyl-2,3-dioxopiperazin-1-ylcarbonylamino)acetamido]-3-[(1-methyl-1H-tetrazol-5-yl)thiomethyl]-7α-methylthioceph-3-em-4-carboxylic acid The 3-acetoxymethylcephem (from Example 48(a)) (335 mg) and 5-mercapto-1-methyl-1H-tetrazole (116 mg) in 1,2-dichloroethane were heated at reflux under nitrogen for 6 hours. The mixture was evaporated to dryness in vacuo and the residue was triturated with isopropanol (10 ml) to give the title compound, (325 mg).

I.R. (KBr) 1775 cm$^{-1}$.

N.M.R. (DMSO-d$_6$) δ=1.07 (t, J=7, 3H); 1.87 and 2.21 (2×s, SCH$_3$); 3.32–3.82 (m, 6H); 3.88 (m, 2H); 3.91 and 3.94 (2×s, 3H); 4.12–4.42 (m, CH$_2$OAc); 5.06 (2×s, C$_6$-H); 5.27 (s, 2H); 5.67 (d, J=7, $\overline{\text{CHNH}}$); 7.25–7.52 (m, 9H); 9.74 (s, 1H); 9.85 and 9.91 ($\overline{\text{2×d}}$, J=7, NH).

(c) 7β-[DL-2-(4-Benzyloxycarbonyloxyphenyl)-2-(4-ethyl-2,3-dioxopiperazin-1-ylcarbonylamino)acetamido]-7α-hydroxyamino-3-[(1-methyl-1H-tetrazol-5-yl)thiomethyl]ceph-3-em-4-carboxylic acid This compound was prepared from the 7α-methylthiocephem (Example 48(b)) (320 mg) by the method described for Example 9(b). Trituration of the crude product with isopropanol (10 ml) gave the title compound, (270 mg).

I.R. (KBr) 1775 cm$^{-1}$.

N.M.R. (DMSO d$_6$) δ=1.07 (t, J=7, 3H); 3.23–3.72 (m, 6H); 3.89 (m, 2H); 3.91 and 3.94 (2×s, 3H); 4.11 and 4.34, 4.17 and 4.35 (2×ABq, J=14, 2H); 4.99 and 5.05 (2×s, 1H); 5.26 and 5.27 (2×s, 2H); 5.70 and 5.71 (2×d, J=7, $\overline{\text{CHNH}}$); 6.55 (br.s., 1H); 7.22–7.52 (m, 9H); 8.06 and 8.17 (2×s, 1H); 9.48 and 9.55 (2×s, 1H); 9.85 and 9.88 (2×d, J=7, NH).

EXAMPLE 49

7β-[D-2-(4-Ethyl-2,3-Dioxopiperazin-1-ylcarbonylamino)-2-phenylacetamido]-7α-hydroxyamino-3-[(1,3,4-thiadiazol-2-yl)thiomethyl]ceph-3-em-4-carboxylic acid sodium salt (a) 7β-[D-2-(4-Ethyl-2,3-dioxopiperazin-1-ylcarbonylamino)-2-phenylacetamido]-3-[(1,3,4-thiadiazol-2-yl)thiomethyl]-7-methylthioceph-3-em-4-carboxylic acid 7β-[D-2-(4-Ethyl-2,3-dioxopiperazin-1-ylcarbonylamino)-2-phenylacetamido]-7α-methylthiocephalosporanic acid (Example 6(a)) (1.0 g) was treated with 2-mercapto-1,3,4-thiadiazole (0.38 g) in a similar manner to that described in Example 39(a) to give the title compound, (0.45 g).

I.R. (KBr) 1780 cm$^{-1}$.

N.M.R. (DMSO d$_6$) δ=1.08 (t, J=7, 3H); 2.22 (s, 3H); 3.10–3.71 (m, 6H); 3.81–4.00 (m, 2H); 4.20 and 4.59 (ABq, J=13, 2H); 5.06 (s, 1H); 5.66 (d, J=7, 1H); 7.25–7.56 (m, 5H); 9.56 (s, 1H);
9.69 (s, 1H); 9.84 (d, J=7, NH).

(b) 7β-[D-2-(4-Ethyl-2,3-dioxopiperazin-1-ylcarbonylamino)-2-phenylacetamido]-7α-hydroxyamino-3-[(1,3,4-thiadiazol-2-yl)thiomethyl]ceph-3-em-4-carboxylic acid, sodium salt The title salt (285 mg) was prepared from the 7α-methylthiocephem (from Example 49(a) above) (400 mg) by treatment with mercuric acetate and hydroxylamine as described on Example 9(b). The sodium salt was then obtained by treatment of the acid with sodium bicarbonate (36 mg) in water followed by freeze drying.

I.R. (KBr) 1780 cm$^{-1}$.

N.M.R. (D$_2$O) δ−1.19 (t, J=6, 3H); 3.11–4.63 (m, 10H); 5.08 (s, 1H); 5.52 (s, 1H); 7.39–7.62 (m, 5H); 9.38 (s, 1H).

EXAMPLE 50

3-Acetoxymethyl-7α-hydroxyamino-7β-[D-2-(3-methanesulphonyl-2-oxoimidazolidin-1-ylcarbonylamino)-2-phenylacetamido]ceph-3-em-4-carboxylic acid (a) Benzhydryl 3-acetoxymethyl-7β-[D-2-(3-methanesulphonyl-2-oxoimidazolidin-1-ylcarbonylamino)-2-phenylacetamido]-7α-methylthioceph-3-em-4-carboxylate A suspension of D-2-(3-methanesulphonyl-2-oxoimidazolidin-1-ylcarbonylamino)-2-phenylacetic acid (1.18 g) in dichloromethane (25 ml) was treated with pyridine (280 μl). After stirring at room temperature for 5 minutes, the almost clear solution was cooled to −60° and trichloroacetyl chloride (387 μl) was added. The solution was then gradually warmed to −40° C. over 1 hour, re-cooled to −60° C. and a solution of benzhydryl 7β-amino-7-methylthiocephalosporanate (1.67 g) in dichloromethane (5 ml) was added. The reaction mixture was warmed to room temperature over 1 hour, stirred for a further 18 hours, and then washed with water (2×30 ml). Drying followed by evaporation of the solvent in vacuo gave the crude product which after chromatography on silica gel (eluting with a dichloromethane-ethyl acetate gradient), afforded the title compound as a light yellow solid, (815 mg).

I.R. (KBr) 1785 cm$^{-1}$.

N.M.R. (CDCl$_3$) δ=2.02 (s, 3H); 2.25 (s, 3H); 3.31 (s, 3H); 3.24–3.34 (m, 2H); 3.88–3.94 (m, 4H); 4.85 and 5.09 (ABq, J=14, 2H); 4.92 (s, 1H); 5.50 (d, J=7, $\overline{\text{CHNH}}$); 6.53 (s, NH); 6.89 (s, 1H); 7.29–7.48 (m, 15H); $\overline{\text{8.85}}$ (d, J=7, $\overline{\text{CHNH}}$).

(b) 3-Acetoxymethyl-7β-[D-2-(3-methanesulphonyl-2-oxo-imidazolidin-1-ylcarbonylamino)-2-phenylacetamido]-7α-methylthioceph-3-em-4-carboxylic acid The benzhydryl ester from the previous step [50(a)] (403 mg) was treated with aluminium chloride and anisole as described previously for Example 39(d). Re-evaporation of the crude product from 2:1 dichloromethane-carbon tetrachloride afforded the title compound as a white solid, (255 mg).

I.R. (KBr) 1780 cm$^{-1}$.

N.M.R. (CDCl$_3$) δ=2.10 (s, 3H); 2.37 (s, 3H); 3.26 and 3.47 (ABq, J=18, 2H); 3.55 (s, 3H); 3.91-3.92 (m, 4H); 4.89 and 5.15 (ABq, J=13, 2H); 5.01 (s, 1H); 5.57 (d, J=7, C$\underline{H}$NH); 7.22-7.65 (m, 6H, CON$\underline{H}$ and C$_6$H$_5$); 9.15 (d, J=7, NH).

(c) 3-Acetoxymethyl-7α-hydroxyamino-7β-[D-2-(3-methanesulphonyl-2-oxoimidazolidin-1-ylcarbonylamino)-2-phenylacetamido]-ceph-3-em-4-carboxylic acid The 7α-methylthiocephem from the previous Example [50(b)] (250 mg) was treated with mercuric acetate and hydroxylamine hydrochloride as previously described for Example 9(b). Trituration of the crude product with isopropanol (3 ml) gave the title compound, (166 mg).

I.R. (KBr) 1780 cm$^{-1}$.

N.M.R. (DMSO-d$_6$) δ=1.98 (s, 3H); 3.16 and 3.48 (ABq, J=18, 2H); 3.33 (s, 3H); 3.67-3.81 (m, 4H); 4.56 and 4.86 (ABq, J=12, 2H); 5.01 (s, 1H); 5.64 (d, J=7, C$\underline{H}$NH); 6.49 (s, 1H); 7.26-7.43 (m, 5H); 8.17 (s, 1H); $\overline{8.77}$ (d, J=7, NH); 9.51 (s, 1H).

EXAMPLE 51

7β-[D-2-(4-Ethyl-2,3-dioxopiperazin-1-ylcarbonylamino)-2-phenylacetamido]-7α-hydroxyamino-3-azidomethylceph-3-em-4-carboxylic acid (a) 7β-[D-2-(4-Ethyl-2,3-dioxopiperazin-1-ylcarbonylamino)-2-phenylacetamido]-7α-methylthio-3-azidomethylceph-3-em-4-carboxylic acid 7β-[D-2-(4-Ethyl-2,3-dioxopiperazin-1-ylcarbonylamino)-2-phenylacetamido]-7α-methylthiocephalosporanic acid (0.880 g) was dissolved in a saturated aqueous solution of sodium hydrogen carbonate [20 ml] and adjusted to pH 6.5 with 2N hydrochloric acid. Lithium azide (0.105 g) was added and the reaction mixture was stirred at 60° C. for 4 hours. The mixture was allowed to cool, overlaid with ethyl acetate [100 ml] and adjusted to pH 2. The layers were separated, the aqueous layer was extracted with ethyl acetate [2×100 ml], and the organic layers were combined, dried over magnesium sulphate and the solvent was removed in vacuo. The crude product was chromatographed over silica [gradient elution isopropyl alcohol-:acetic acid:dichloromethane]. Collection and evaporation of appropriate fractions gave the title compound, (0.340 g).

I.R. (KBr) 1780 cm$^{-1}$.

N.M.R. (DMSO-d$_6$) δ=1.06 (t, J=6 Hz, 3H); 2.21 (s, 3H); 3.2-3.6 (m, 6H); 3.89 (m, 2H); 3.98 and 4.29 (ABq, J=14 Hz, 2H); 5.07 (s, 1H); 5.63 (d, J=6 Hz, 1H); 7.28-7.48 (m, 6H); 9.69 (s, 1H); 9.80 (d, J=6 Hz, 1H).

(b) 7β-[D-2-(4-Ethyl-2,3-dioxopiperazin-1-ylcarbonylamino)-2-phenylacetamido]-7-α-hydroxyamino-3-azidomethylceph-3-em-4-carboxylic acid The 7α-methylthiocephem (from Example 51(a) above) (0.230 g) in dimethylformamide (4 ml) was cooled to −60° C. A solution of mercuric acetate (0.266 g) in dimethylformamide (2 ml) was added followed immediately by hydroxylamine hydrochloride (0.030 g) in dimethylformamide (2 ml) and triethylamine. The reaction mixture was stirred for 1½ hours while allowing the temperature to rise to +10° C. The mixture was then added dropwise to ether (400 ml) and the solid was filtered off and suspended in methanol (40 ml). Hydrogen sulphide was bubbled through the suspension for 10 minutes with stirring, the mixture was filtered through "Hyflo" (Trade Mark) and the solvent was removed in vacuo yielding the title compound, (0.205 g).

I.R. (KBr) 1780 cm$^{-1}$.

N.M.R. (DMSO-d$_6$) δ=1.06 (t, J=6 Hz, 3H); 3.10-3.55 (m, 6H); 3.88 (m, 2H); 3.94 and 4.23 (ABq, J=12 Hz, 2H); 5.02 (s, 1H); 5.67 (d, J 6 Hz, 1H); 6.50 (s, 1H); 7.30-7.50 (m, 5H); 7.84 (s, 1H); 8.20 (s, 1H); 9.58 (s, 1H); 9.87 (d, J=6 Hz, 1H).

EXAMPLE 52

7β-[D-2-(4-Benzyl-2,3-dioxopiperazin-1-ylcarbonylamino)-2-phenylacetamido]-7α-hydroxyaminocephalosporanic acid (a) Benzhydryl 7β-[D-2-(4-benzyl-2,3-dioxopiperazin-1-ylcarbonylamino)-2-phenylacetamido]-7α-methylthiocephalosporonate Benzhydryl 7β-amino-7α-methylthiocephalosporanate (1.38 g) in dichloromethane (25 ml) was cooled to −30° C. and treated dropwise over 1 minute with a solution of D-2-(4-benzyl-2,3-dioxopiperazin-1-ylcarbonylamino)-2-phenylacetyl chloride (1.22 g) in dichloromethane (25 ml). Pyridine (237 μl) was added during 1 minute and the solution was stirred over 30 minutes whilst allowing the temperature to rise to 0° C., then washed with 2N hydrochloric acid (50 ml), saturated sodium bicarbonate (50 ml) and saturated sodium chloride solution (50 ml). The reaction mixture was then dried (Na$_2$SO$_4$), the solvent was removed in vacuo and the residue was chromatographed (silica gel, dichloromethane: ethylacetate) to give the title compound, (1.3 g).

I.R. (KBr) 1785 cm$^{-1}$.

N.M.R. (CDCl$_3$) δ=2.04 (s, 3H); 2.25 (s, 3H); 3.28 and 3.38 (ABq, J=13, 2H); 3.35-3.52 (m, 2H); 3.84-4.10 (m, 2H); 4.63 and 4.72 (ABq, J=12, 2H); 4.63 and 4.71 (ABq, J=10, 2H); 4.95 (s, 1H); 5.58 (d, J=7, 1H); 6.82 (s, NH); 6.90 (s, 1H); 7.18-7.68 (m, 20H); 9.98 (d, J=7, NH).

(b) Benzhydryl 7β-[D-2-(4-benzyl-2,3-dioxopiperazin-1-ylcarbonylamino)-2-phenylacetamido]-7α-hydroxyaminocephalosporanate The title compound (0.36 g) was prepared from the 7α-methylthiocephem (from Example 52(a) above) (0.85 g) similarly to the procedure of Example 38(b).

I.R. (KBr) 1780 cm$^{-1}$.

N.M.R. (CDCl$_3$) δ=2.09 (s, 3H); 2.78 and 3.02 (ABq, J=12, 2H); 3.24-3.48 (m, 2H); 3.72-4.04 (m, 2H); 4.58 and 4.72 (ABq, 2H); 4.88 and 4.98 (ABq, J=12, 2H); 5.37 (s, 1H); 5.54 (d, J=6, 1H); 6.67 (brs, NH); 6.92 (s, 1H); 7.04 (brs, 1H, exch.); 6.99-7.64 (m, 20H); 8.72 (brs, 1H, exch.); 10.04 (d, J=6, NH).

(c) 7β-[D-2-(4-benzyl-2,3-dioxopiperazin-1-ylcarbonylamino)-2-phenylacetamido]-7α-hydroxyaminocephalosporanic acid The title compound (95 mg) was prepared from the benzhydryl ester [from Example 52(b) above] (360 mg) similarly to the procedure of Example 38(c).

I.R. (KBr) 1780 cm$^{-1}$.

N.M.R. (DMSO d$_6$) δ=2.02 (s, 3H); 3.21-3.65 (m, 4H); 3.81-4.01 (m, 2H); 4.61 and 4.91 (ABq, J=12, 2H); 4.62 (s, 2H); 5.07 (s, 1H); 5.71 (d, J=6, 1H); 6.54 (brs, 1H, exch.); 7.24-7.58 (m, 10H); 8.21 (s, 1H); 9.56 (s, 1H); 9.90 (d, J=6, NH).

EXAMPLES 53 and 54

The following compounds of the formula (I) were prepared from the appropriate starting materials using the process of Example 52 parts (a) and (b).

Mark], the aqueous layer was separated, washed with ethyl acetate (50 ml), overlaid with n-butanol:ethyl acetate (1:3) (200 ml) and adjusted to pH 2 with 2N hydrochloric acid. The layers were separated, the aqueous layer extracted again with n-butanol:ethyl acetate

| Example No. and side chain stereochemistry | R | R$^1$ | R$^2$ | I.R. (KBr) cm$^{-1}$ | N.M.R. (DMSO—d$_6$) |
|---|---|---|---|---|---|
| 53 D- | Ph— | —C(=O)—N(piperazine-2,3-dione)N—n-Octyl | —CH$_2$—OAc | 1780 | δ = 0.88 (t,J = 6,3H); 1.16–1.40 (m, 10H); 1.42–1.64 (m, 2H); 2.02 (s, 3H); 3.08–3.68 (m, 6H); 3.79–4.06 (m, 2H); 4.60 and 4.89 (ABq, J = 12, 2H); 5.04 (s, 1H); 5.70 (d, J = 6, 1H); 6.52 (br.s., 1H); 7.23–7.59 (m, 5H); 8.20 (s, 1H); 9.56 (s, 1H); 9.88 (d, J = 6, NH). |
| 54 D- | Ph— | —C(=O)—N(piperazine-2,3-dione)N—n-Butyl | —CH$_2$—OAc | 1780 | δ = 0.87 (t, J = 6, 3H); 1.18–1.26 (m, 2H); 1.39–1.59 (m, 2H); 1.99 (s, 3H); 3.05–3.69 (m, 6H); 3.78–4.02 (m, 2H); 4.56 and 4.87 (ABq, J = 12, 2H); 5.02 (s, 1H); 5.66 (d, J = 6, 1H); 6.49 (s, 1H); 7.14–7.61 (m, 5H); 8.18 (s, 1H); 9.54 (s, 1H); 9.85 (d, J = 6, NH). |

EXAMPLE 55

7β-[D-2-(3-Ethyl-2-oxo-imidazolidin-1-ylcarbonylamino)-2-phenylacetamido]-7α-hydroxyaminocephalosporanic acid (a) Benzhydryl 7β-[D-2-(3-ethyl-2-oxo-imidazolidin-1-ylcarbonylamino)-2-phenylacetamido]-7α-methylthiocephaloposranate A solution of D-2-[3-ethyl-2-oxo-imidazolidin-1-ylcarbonylamino]phenylacetic acid (0.800 g) (German OLS 2,152,968) and pyridine (0.208 ml) in dichloromethane (24 ml) was cooled to −40° C. and trichloroacetyl chloride (0.288 ml) was added. The reaction mixture was stirred for 15 minutes, cooled to −60° C. and benzhydryl 7β-amino-7α-methylthiocephalosporanate (1.28 g) in dichloromethane (24 ml) was added over 3 minutes. The mixture was then stirred for 1 hour while allowing it to warm to +20° C., washed with saturated sodium hydrogen carbonate solution (20 ml), the organic phase dried over magnesium sulphate, and the solvent removed in vacuo. The crude product was purified by chromatography over silica. Elution was carried out with dichloromethane:ethyl acetate (4:1) and collection and evaporation of appropriate fractions yielded the title compound, (1.24 g).

I.R. (KBr) 1780 cm$^{-1}$.

N.M.R. (CDCl$_3$) δ=1.19 (t, J=6 Hz, 3H); 2.06 (s, 3H); 2.32 (s, 3H); 3.29–3.50 (m, 6H); 3.90 (m, 2H); 4.89 and 5.15 (ABq, J=12 Hz, 2H); 4.96 (s, 1H); 5.60 (d, J=6 Hz, 1H); 6.92 (s, 1H); 6.94 (s, 1H); 7.30–7.53 (m, 15H); 9.22 (d, J=6 Hz, NH).

(b) 7β-[D-2-(3-Ethyl-2-oxo-imidazolidin-1-ylcarbonylamino)-2-phenylacetamido]-7α-methylthiocephalosporanic acid The benzhydryl cephalosporonate (0.83 g) (from Example 55(a) in dry dichloromethane (560 ml) was cooled to −60° C. Anisole (0.715 ml) was added followed by aluminium trichloride (0.440 g) in nitromethane (2 ml). The mixture was stirred for 20 minutes and then partitioned between saturated sodium hydrogen carbonate solution (30 ml) and ethyl acetate (300 ml). The mixture was filtered through "Hyflo" [Trade (150 ml), the organic layers were combined, dried over magnesium sulphate and the solvents removed in vacuo giving the title compound, (0.34 g).

I.R. (KBr) 1785 cm$^{-1}$.

N.M.R. (CDCl$_3$) δ=1.17 (t, J=6 Hz, 3H); 2.10 (s, 3H); 2.39 (s, 3H); 3.20–3.50 (m, 7H); 3.83 (m, 2H); 4.89 and 5.15 (ABq, J=13 Hz, 2H); 5.04 (s, 1H); 5.60 (d, J=6 Hz, 1H); 7.36–7.53 (m, 5H); 7.97 (s, NH); 9.60 (d, J=6 Hz, NH).

(c) 7β-[D-2-(3-Ethyl-2-oxo-imidazolidin-1-ylcarbonylamino)-2-phenylacetamido]-7α-hydroxyaminocephalosporanic acid The compound from the previous step (55(b)) was reacted with hydroxylamine in a similar manner to the method of 51(b) to yield the title compound.

I.R. (KBr) 1775 cm$^{-1}$.

N.M.R. (DMSO-d$_6$) δ=1.08 (t, J=6 Hz, 3H); 2.00 (s, 3H); 3.20–3.50 (m, 6H); 3.62 (m, 2H); 4.57 and 4.86 (ABq, J=13 Hz, 2H); 4.99 (s, 1H); 5.63 (d, J=6 Hz, 1H); 6.43 (s, NH); 7.26–7.42 (m, 6H); 8.13 (s, OH); 9.08 (d, J=6 Hz, NH); 9.46 (s, OH).

EXAMPLE 56

7β-[D-2-(4-Ethyl-2,3-dioxopiperazin-1-ylcarbonylamino)-2-(3,4-dihydroxyphenyl)acetamido]-7α-hydroxyaminocephalosporanic acid (a) Diphenylmethyl 7β-[DL-2-(4-ethyl-2,3-dioxopiperazin-1-ylcarbonylamino)-2-(3,4-diacetoxyphenyl)acetamido]-7α-methylthiocephalosporanate DL-2-(4-Ethyl-2,3-dioxopiperazin-1-ylcarbonylamino)-2-(3,4-diacetoxyphenyl)acetic acid [EP 0071395 Example 18(b)] (2.3 g) was treated with trichloroacetyl chloride (0.96 g), triethylamine (740 μl) and diphenylmethyl 7β-amino-7α-methylthiocephalosporanate (2.56 g) similarly to the procedure of Example 50(a) to give the crude title compound. Chromatography over silica (20 g) eluting with a n-hexane to ethyl acetate gradient afforded the pure title compound (1.6 g).

I.R. (film) 1775 cm$^{-1}$.

N.M.R. (CDCl₃) δ=1.1 (t, J=7, 3H); 2.0 (s, 3H); 2.25 (m, 9H); 3.0-4.2 (m, 8H); 4.6-5.1 (m, 3H); 5.8+6.2 (d+brs, J=6, 1H); 6.8 (s, 1H); 7.0-7.6 (m, 13H); 7.9 and 8.1 (2×s, NH); 9.7-10.1 (m, NH). (60 MHz).

(b) Diphenylmethyl 7β-[D-2-(4-ethyl-2,3-dioxopiperazin-1-ylcarbonylamino)-2-(3,4-diacetoxyphenyl)acetamido]-7α-t-butyldiphenylsilyoxyaminocephalosporanate Isomer 1

The 7α-methylthiocephem (from Example 56(a)) (0.6 g) in dimethylformamide (10 ml) was cooled to −50° C. under nitrogen and treated successively with a solution of mercuric acetate (0.24 g) in dimethylformamide (1 ml) followed by a solution of O-(t-butyldiphenylsilyl)-hydroxylamine (see Example 60a) (0.2 g) in dimethylformamide (1 ml). The mixture was warmed to 20° C. during 0.5 hours and added to ethyl acetate (100 ml). This solution was washed with water (3×50 ml), dried (Na₂SO₄), and evaporated in vacuo. The crude product was purified by chromatography (silica gel, hexane/ethyl acetate gradient) to give two separate isomers.

Isomer 1 (0.2 g) (D-isomer, eluted first).

I.R. (KBr) 1780 cm⁻¹.

N.M.R. (CDCl₃) δ=1.05 (s, 9H); 1.2 (t, J=6, 3H); 1.65 (s, 2H, H₂O); 2.07 (s, 3H); 2.3 (2×s, 6H); 2.95 and 3.18 (2H, ABq, J=14); 3.35-3.6 (m, 4H); 4.05 (m, 2H); 4.7 (s, 1H); 4.9 and 5.1 (2H, ABq, J=13); 5.75 (d, J=7, 1H); 6.65 (s, NH); 6.95 (s, 1H); 7.1-7.8 (m, 24H); 10.15 (d, J=7, NH).

Only "isomer 1", the D-form, was progressed through the subsequent stages set out in parts (c) and (d). "Isomer 2", eluted last, was discarded.

(c) Diphenylmethyl 7β-[D-2-(4-ethyl-2,3-dioxopiperazin-1-ylcarbonylamino)-2-(3,4-diacetoxyphenyl)acetamido]-7α-hydroxyaminocephalosporanic acid The D-isomer ("isomer I"), product from Example 56(b) (0.55 g) in acetonitrile (10 ml) was cooled to 0° C. with stirring. Aqueous hydrofluoric acid (40%) (4 ml) was added and after 1.0 hours the mixture was diluted with ethyl acetate (100 ml) and water (50 ml). Saturated aqueous sodium bicarbonate was added to pH 7 and the organic phase was separated, washed with brine and dried (Na₂SO₄). The solvent was evaporated in vacuo to give the crude product (0.43 g) which was purified by chromatography (silica gel, dichloromethane/ethyl acetate gradient) to afford the title compound, (0.27 g).

I.R. (film) 1770 cm⁻¹.

N.M.R. (CDCl₃) δ=1.25 (t, J=7, 3H); 1.6 (s, 2H, H₂O); 2.05 (s, 3H); 2.15 (s, 3H); 2.25 (s, 3H); 2.55 and 3.15 (2H, ABq, J=16); 3.4-3.7 (m, 4H); 3.95-4.2 (m, 2H); 4.95 and 5.2 (2H; ABq, J=13); 5.45 (s, 1H); 5.65 (d, J=6, 1H); 6.7 (s, NH); 6.9-6.95 (m, 2H); 7.0-7.5 (m, 13H); 8.9 (brs, NH); 10.2 (d, J=6, NH).

(d) 7β-[D-2-(4-Ethyl-2,3-dioxopiperazin-1-ylcarbonylamino-2-(3,4-dihydroxyphenyl)acetamido]-7α-hydroxyaminocephalosporanic acid The diphenylmethyl ester from part (c) (0.25 g) in dichloromethane (5 ml) and anisole (181 μl) was cooled to −60° C. under nitrogen. A solution of aluminium trichloride (0.224 g) in nitromethane (2 ml) was added dropwise during 2 minutes with rapid stirring and, after 1.0 hours, the mixture was diluted with ethyl acetate (50 ml) and 2M hydrochloric acid (25 ml). The ethyl acetate layer was back-extracted with saturated aqueous sodium bicarbonate (2×5 ml) which was saturated with NaCl, overlaid with ethyl acetate/tetrahydrofuran (1:1, 50 ml) and acidified to pH 1.5 with 2M hydrochloric acid. The organic extract was dried (Na₂SO₄) and evaporated in vacuo. The residue (0.12 g) in dilute sodium bicarbonate solution (5 ml) was adjusted to pH 8.5, stirred for 0.5 hours saturated with NaCl, overlaid with ethyl acetate/tetrahydrofuran (1:1, 50 ml) and the mixture acidified to pH 1.5 with 2M hydrochloric acid. The organic extract was dried (Na₂SO₄) and evaporated in vacuo to afford the title compound, (60 mg).

I.R. (KBr) 1775 cm⁻¹.

N.M.R. (DMSO-d₆) δ=1.10 (t, J=6, 3H); 2.18 (s, 3H); 3.2-3.4 (m, 4H) and HOD; 3.55 (m, 2H); 3.9 (m, 2H); 4.65 and 4.9 (2H, ABq, J=12); 5.1 (s, 1H); 5.4 (d, J=6, 1H); 6.65 and 6.9 (m, 3H, Ar); 8.85 (s, NH); 9.9 (d, J=6, NH).

EXAMPLE 57

7β-[D-2-(2,3-Dioxo-4-n-octylpiperazin-1-ylcarbonylamino)-2-phenylacetamido]-7α-hydroxyamino-3-[1-methyl-1H-tetrazol-5-yl)thiomethyl]ceph-3-em-4-carboxylic acid (a) 3-Acetoxymethyl-7β-[D-2-(2,3-dioxo-4-n-octylpiperazin-1-ylcarbonylamino)-2-phenylacetamido]-7α-methylthioceph-3-em-4-carboxylic acid The benzhydryl ester from Example 53(a) (1.45 g) in dichloromethane (50 ml) containing anisole (1.44 g) was cooled to −5° and trifluoroacetic acid (5 ml) was added dropwise over 2 minutes. After stirring at 0° for 2 hours, toluene (50 ml) was added and the solution was evaporated to dryness in vacuo below 25°. Further toluene (50 ml) was added and the solution was re-evaporated in the same way. Trituration of the residue with diethyl ether (100 ml) gave the title compound as a pale yellow solid (970 mg).

I.R. (KBr) 1785 cm⁻¹.

N.M.R. (DMSO-d₆) δ=0.85 (t, J=7, 3H); 1.24 (s, 10H); 1.48 (brs., 2H); 2.00 (s, 3H); 3.24-3.53 (m, 6H); 3.86-3.89 (m, 2H); 4.61 and 4.93 (ABq, J=18, 2H); 5.07 (s, 1H); 5.62 (d, J=8, 1H); 7.18-7.45 (m, 5H); 9.67 (s, 1H); 9.81 (d, J=8, 1H).

(b) 7β-[D-2-(2,3-Dioxo-4-n-octylpiperazin-1-ylcarbonylamino]-2-phenylacetamido]-3-[(1-methyl-1H-tetrazol-5-yl)thiomethyl]-7α-methylthioceph-3-em-4-carboxylic acid Reaction of the 3-acetoxymethylcephem obtained in the previous step (422 mg) with 1-methyl-1H-tetrazole-5-thiol (83 mg) by the procedure described for Example 6(b) gave the title compound as a white solid (123 mg).

I.R. (KBr) 1785 cm⁻¹.

N.M.R. (DMSO-d₆) δ=0.83 (t, J=7, 3H); 1.22 (s, 10H); 1.46 (brs., 2H); 2.18 (s, 3H); 3.30 (brs., 2H); 3.35 and 3.60 (ABq, J=18, 2H); 3.52 (brs., 2H); 3.82-3.86 (m, 2H); 3.88 (s, 3H); 4.12 and 4.36 (ABq, J=13, 2H); 5.01 (s, 1H); 5.60 (d, J=8, CHNH); 7.27-7.44 (m, 5H); 9.66 (s, 1H); 9.80 (d, J=7, NH).

(c) 7β-[D-2-(2,3-Dioxo-4-n-octylpiperazin-1-ylcarbonylamino)-2-phenylacetamido]-7α-hydroxyamino-3-[(1-methyl-1H-tetrazol-5-yl)thiomethyl]ceph-3-em-4-carboxylic acid The title compound (107 mg) was prepared from the 7α-methylthiocephem of part (b) (120 mg) by reaction with mercuric acetate and hydroxylamine hydrochloride and triethylamine as previously described for Example 9(b).

I.R. (KBr) 1780 cm⁻¹.

N.M.R. (DMSO-d₆) δ=0.85 (t, J=7, 3H); 1.24 (m, 10H); 1.48 (m, 2H); 3.26 and 3.57 (ABq, J=18, 2H); 3.31-3.38 (m, 2H); 3.46-3.52 (m, 2H); 3.86-3.90 (m, 2H);

3.90 (s, 3H); 4.10 and 4.37 (ABq, J=13, 2H); 4.99 (s, 1H); 5.66 (d, J=8, CHNH); 6.55 (brs., 1H); 7.27–7.45 (m, 5H); 8.18 (s, 1H); 9.54 (s, 1H); 9.60 (brs., 1H); 9.86 (d, J=7, NH).

EXAMPLE 58

7β-[2-(R)-(4-n-Butyl-2,3-dioxopiperazin-1-ylcarbonylamino)-3-(S)-hydroxybutanamido]-7α-hydroxyaminocephalosporanic acid (a) Benzhydryl 7β-[2-(R)-(4-n-butyl-2,3-dioxopiperazin-1-ylcarbonylamino)-3-(S)-hydroxybutanamido]-7α-methylthiocephalosporanate 2-(R)-(4-n-Butyl-2,3-dioxopiperazin-1-ylcarbonylamino)-3-(S)-hydroxybutyric acid (3.25 g) and benzhydryl 7β-amino-7α-methylthiocephalsoporanate (5.0 g) were coupled by the method of Example 46(a) to give the title compound, (3.23 g).

I.R. ($CH_2Cl_2$) 1783 $cm^{-1}$.

N.M.R. ($CDCl_3$) δ=0.94 (m, 3H); 1.2–1.60 (m, 7H); 2.05 (s, 3H); 2.35 (s, 3H); 3.41 (m, 6H); 4.11 (m, 2H); 4.50 (m, 2H); 4.93 and 5.16 (ABq, 2H, J=15); 4.96 (s, 1H); 6.89 (s, 1H); 7.27 to 7.49 (m, 10H); 7.88 (s, 1H); 9.59 (d, 1H, J=6).

(b) 7β-[2-(R)-(4-n-Butyl-2,3-dioxopiperazin-1-ylcarbonylamino)-3-(S)-hydroxybutanamido]-7α-methylthiocephalosporanic acid The title compound (2.9 g) was prepared from the benzhydryl ester (3.8 g) of part (a) using the procedure of Example 57(a).

I.R. (KBr) 1785 $cm^{-1}$.

N.M.R. (DMSO-$d_6$) δ=0.88 (t, 3H, J=7); 1.08 (m, 3H); 1.27 (q, 2H, J=7); 1.49 (m, 2H); 2.02 (s, 3H); 2.26 (s, 3H); 3.34 to 3.63 (m, 6H); 3.90 to 4.12 (m, 2H); 4.33 (m, 2H); 4.64 and 4.95 (ABq, 2H, J=13); 5.07 (s, 1H); 9.16 (s, 1H); 9.27 (d, 1H, J=6).

(c) 7β-[2-(R)-(4-n-Butyl-2,3-dioxopiperazin-1-ylcarbonylamino)-3-(S)-hydroxybutanamido]-7α-hydroxyaminocephalosporanic acid The title compound (220 mg) was prepared from the product of part (b) (300 mg) by the method of Example 9(b).

I.R. (KBr) 1778 $cm^{-1}$.

N.M.R. (DMSO-$d_6$) δ=0.87 (t, 3H, J=7.5); 1.07 (m, 3H); 1.26 (m, 2H); 1.47 (m, 2H); 2.01 (s, 3H); 3.28 to 3.54 (m, 6H); 3.89 (m, 2H); 4.33 (m, 2H); 4.61 and 4.89 (ABq, 2H, J=15); 5.09 (s, 1H); 8.88 (s, 1H); 9.27 (d, 1H, J=6).

EXAMPLE 59

7β-[D-2-(4-Benzyl-2,3-dioxopiperazin-1-ylcarbonylamino)-2-phenylacetamido]-3-[(5,6-dioxo-4-methyl-1,4,5,6-tetrahydro-1,2,4-triazin-3-yl)thiomethyl]-7α-hydroxyaminoceph-3-em-4-carboxylic acid (a) 7β-[D-2-(4-benzyl-2,3-dioxopiperazin-1-ylcarbonylamino)-2-phenylacetamido]-7α-methylthiocephalosporanic acid Benzhydryl 7β-[D-2-(4-benzyl-2,3-dioxopiperazin-1-ylcarbonylamino)-2-phenylacetamido]-7α-methylthiocephalsporanate (Example 52(a) (1.5 g) was treated with aluminium chloride (0.72 g) and anisole (1.17 g) in a similar manner to that described in Example 38(c) to give the title compound (0.96 g).

I.R. (KBr) 1785 $cm^{-1}$.

N.M.R. (DMSO-$d_6$)δ=1.98 (s, 3H); 2.19 (s, 3H); 3.07–3.69 (m, 4H); 3.78–3.98 (m, 2H); 4.58 (s, 2H); 4.60 and 4.92 (ABq, J=12, 2H); 5.06 (s, 1H); 5.62 (d, J=6, 1H); 7.14–7.66 (m, 10H); 9.67 (s, 1H); 9.81 (d, J=9, NH).

(b) 7β-[D-2-(4-Benzyl-2,3-dioxopiperazin-1-ylcarbonylamino-2-phenyl-acetamido]-3-[(5,6-dioxo-4-methyl-1,4,5,6-tetrahydro-1,2,4-triazin-3-yl)thiomethyl]-7α-methylthioceph-3-em-4-carboxylic acid The title compound (0.29 g) was prepared from the product of part (a) (0.31 g) by the method described in Example 14(a) from appropriate starting materials.

I.R. (KBr) 1780 $cm^{-1}$.

N.M.R. (DMSO-$d_6$)δ=2.21 (s, 3H); 3.11–3.67 (m, 4H); 3.25 (s, 3H); 3.78–3.99 (m, 2H); 3.95 and 4.12 (ABq, J=12, 2H); 4.59 (s, 2H); 5.04 (s, 1H); 5.63 (d, J=6, 1H); 7.17–7.58 (m, 10H); 9.69 (s, 1H); 9.82 (d, J=6, NH).

(c) 7β-[D-2-(4-Benzyl-2,3-dioxopiperazin-1-ylcarbonylamino)-2-phenylacetamido]-7α-tert-butyldiphenylsilyloxyamino-3-[(5,6-dioxo-4-methyl-1,4,5,6-tetrahydro-1,2,4-triazin-3-yl)thiomethyl]ceph-3-em-4-carboxylic acid The 7α-methylthiocephem from part (b) (330 mg) in dimethylformamide (5 ml) was cooled to −50° and treated successively with solution of mercuric acetate (162 mg) in dimethylformamide (1 ml) and O-(t-butyldiphenylsilyl)hydroxylamine in dimethylformamide (2 ml). The resultant clear solution was warmed to 0° over 1 hour and added slowly to diethyl ether (200 ml) with stirring. After filtration, the ether-damp solid was suspended in methanol (20 ml) and saturated with hydrogen sulphide. The mixture was filtered and evaporated under vacuum. Trituration of the residue with isopropanol gave the title compound as a white solid, (50 mg).

I.R. (KBr) 1785 $cm^{-1}$.

N.M.R. (DMSO-$d_6$)δ=0.97 (s, 9H); 2.95–3.66 (m, 4H); 3.24 (s, 3H); 3.81–3.92 (m, 2H); 3.96 and 4.09 (ABq, J=12, 2H); 4.58 (s, 2H); 5.01 (s, 1H); 5.74 (d, J=6, 1H); 7.02–7.79 (m, 20H); 9.85 (d, J=6, NH); 9.91 (s, 1H).

(d) 7β-[D-2-(4-Benzyl-2,3-dioxopiperazin-1-ylcarbonylamino)-2-phenyl-acetamido]-3-[(5,6-dioxo-4-methyl-1,4,5,6-tetrahydro-1,2,4-triazin-3-yl)thiomethyl]-7α-hydroxyaminoceph-3-em-4-carboxylic acid The 7α-tert-butyldiphenysilyloxyaminocephem from part (c) (50 mg) was treated with 40% aqueous hydrogen fluoride at 0° for 1 hour. Evaporation in vacuo and trituration of the residue with isopropanol gave the title compound. (38 mg).

I.R. (KBr) 1785 $cm^{-1}$.

N.M.R. (DMSO-$d_6$)δ=3.24 (s, 3H); 2.98–3.64 (m, 4H); 3.82–3.94 (m, 2H); 3.92 and 4.09 (ABq, J=12, 2H); 4.59 (s, 2H); 5.02 (s, 1H); 5.68 (d, J=6, 1H); 7.17–7.58 (m, 10H); 8.19 (s, 1H); 9.58 (s, 1H); 9.87 (d, J=6, NH).

EXAMPLE 60

7β-[D-2(4-Ethyl-2,3-dioxopiperazin-1-ylcarbonylamino)-2-phenylacetamido]-7α-hydroxyamino-3-[(5-chlorobenzothiazol-2-yl)thiomethyl]ceph-3-em-4-carboxylic acid (a) O-tert-butyldiphenylsilylhydroxylamine Hydroxylamine hydrochloride (3.48 g) and triethylamine (7 ml) were stirred for 0.25 hours in DMF (50 ml) at 0° C. tert-Butyldiphenylsilyl chloride (13 ml) was added and the mixture was stirred for 1 hour. The mixture was partitioned between pentane (500 ml) and water (100 ml), the layers separated and the aqueous phase extracted with ethyl acetate (2×100 ml). The organic layers were combined, washed with brine (50 ml), dried over magnesium sulphate and the solvent was removed in vacuo. The crude product was triturated with pentane (20 ml) yielding the pure title compound as white solid (4.04 g), m.p.t. 85°–87° C.

Analysis % Found: C, 70.67; H, 7.78; N, 4.87; Calculated for $C_{16}H_{21}NOSi$: C, 70.84; H, 7.75; N, 5.17.

(b) 7β-[D-2-(4-Ethyl-2,3-dioxopiperazin-1-ylcarbonylamino)-2-phenylacetamido]-7α-methylthio-3-[(5-chlorobenzothiazol-2-yl)thiomethyl]ceph-3-em-4-carboxylic acid This compound was prepared in a similar manner to the method described in Example 6(b) using 5-chloro-2-mercaptobenzothiazole and the same cephem.

I.R. (KBr) 1785 cm$^{-1}$.

N.M.R. (DMSO-d$_6$)δ=1.05 (t, J=6 Hz, 3H); 2.18 (s, 3H); 3.35 (m, 3H); 3.52 (m, 2H); 3.63 (½ ABq, J=18 Hz, 1H); 3.86 (m, 2H); 4.09 and 4.84 (ABq, J=12 Hz, 2H); 5.03 (s, 1H); 5.60 (d, J=6 Hz, 1H); 7.26–7.43 (m, 7H); 8.02 (d, J=6 Hz, 1H); 9.65 (s, 1H); 9.80 (d, J=6 Hz, 1H).

(c) 7β-[D-2-(4-Ethyl-2,3-dioxopiperazin-1-ylcarbonylamino)-2-phenylacetamido]-7α-tert-butyldiphenylsilyloxyamino-3-[(5-chlorobenzothiazol-2-yl)thiomethyl]ceph-3-em-4-carboxylic acid The 7α-methylthiocephem from part (b) in dimethylformamide (3 ml) was cooled to −60° C. A solution of mercuric acetate (0.200 g) in dimethylformamide was added followed immediately by a solution of O-tert-butyldiphenylsilylhydroxylamine (0.185 g) in dimethylformamide (3 ml). The reaction mixture was stirred for 0.75 hours while allowing it to warm to +20° C. The mixture was then added dropwise to a 2:1 mixture of ether:petroleum ether (300 ml), the solid filtered off and suspended in methanol (30 ml). Hydrogen sulphide was bubbled through the suspension for 0.20 hours with stirring, the mixture was filtered through "Hyflo" (Trade Mark) and the solvent removed in vacuo. The crude product was chromatographed over silica. Elution was carried out with dichloromethane and an increasing ratio of 1:1 isopropyl alcohol and acetic acid (up to 3% isopropyl alcohol, 3% acetic acid). Collection and evaporation of appropriate fractions gave the title compound, (0.225 g).

I.R. (KBr) 1785 cm$^{-1}$.

N.M.R. (DMSO-d$_6$)δ=0.94–1.06 (m, 12H); 3.15–3.45 (m, 4H); 3.50 (m, 2H); 3.82 (m, 2H); 4.07 and 4.90 (ABq, J=12 Hz, 2H); 4.91 (s, 1H); 5.72 (d, J=6 Hz, 1H); 7.00 (s, 1H); 7.27–7.65 (m, 17H); 7.93 (s, 1H); 8.00 (d, J=6 Hz, 1H); 9.81 (d, J=6 Hz, 1H); 9.85 (s, 1H).

(d) 7β-[D-2-(4-Ethyl-2,3-dioxopiperazin-1-ylcarbonylamino)-2-phenylacetamido]-7α-hydroxyamino-3-[(5-chlorobenzothiazol-2-yl)thiomethyl]ceph-3-em-4-carboxylic acid The 7α-tert-butyldiphenylsilyloxyaminocephem from part (c) [0.200 g] in acetonitrile (3 ml) was cooled to 0° C. and treated with 40% hydrofluoric acid (1 ml) for ½ hour. The reaction mixture was diluted with ethyl acetate (50 ml) and washed thoroughly with saturated brine (4×50 ml). The organic layer was dried over magnesium sulphate and the solvent removed in vacuo. The residue was triturated with ether (2×30 ml) and the title compound filtered off as a white solid (95 mg).

I.R. (KBr) 1775 cm$^{-1}$.

N.M.R. (DMSO-d$_6$)δ=1.07 (t, J=6 Hz, 3H); 3.20 and 3.58 (ABq, J=15 Hz, 2H); 3.3–3.45 (m, 2H); 3.53 (m, 2H); 3.85 (m, 2H); 4.08 and 4.79 (ABq, J=12 Hz, 2H); 4.98 (s, 1H); 5.65 (d, J=6 Hz, 1H); 6.46 (s, 1H); 7.23–7.43 (m, 7H); 7.91 s, 1H); 8.02 (d, J=6 Hz, 1H); 8.12 (s, 1H); 9.52 (s, 1H); 9.85 (d, J=6 Hz, 1H).

EXAMPLE 61

7β-[D-2-(4-Benzyl-2,3-dioxopiperazin-1-ylcarbonylamino)-2-phenylacetamido[-7α-hydroxyamino-3-[(1-methyl-1H-tetrazol-5-yl)thiomethyl]ceph-3-em-4-carboxylic acid (a) 7β-[D-2-(4-Benzyl-2,3-dioxopiperazin-1-ylcarbonylamino)-2-phenylacetamido]-3-[(1-methyl-1H-tetrazol-5-yl)thiomethyl]-7α-methylthioceph-3-em-4-carboxylic acid A solution of 7β-[D-2-(4-Benzyl-2,3-dioxopiperazin-1-ylcarbonylamino)-2-phenylacetamido]-7α-methylthiocephalosporanic acid (Example 59(a)) (0.31 g) and 5-mercapto-1-methyl-1H-tetrazole (0.16 g) in 1,2-dichloroethane (10 ml) was refluxed under nitrogen for 8 hours. The mixture was cooled to room temperature and the title compound was filtered off and dried in vacuo (0.15 g).

I.R. (KBr) 1785 cm$^{-1}$.

N.M.R. (DMSO-d$_6$)δ=2.18 (s, 3H); 3.37 and 3.61 (ABq, J=12, 2H); 3.42–3.52 (m, 2H); 3.78–3.99 (m, 2H); 3.89 (s, 3H); 4.13 and 4.36 (ABq, J=12, 2H); 4.58 (s, 2H); 5.02 (s, 1H); 5.61 (d, J=6, 1H); 7.18–7.54 (m, 10H); 9.67 (s, 1H); 9.81 (d, J=9, NH).

(b) 7β-[D-2-(4-Benzyl-2,3-dioxopiperazin-1-ylcarbonylamino)-2-phenylacetamido]-7α-t-butyldiphenylsilyloxyamino-3-[(1-methyl-1H-tetrazol-5-yl)thiomethyl]ceph-3-em-4-carboxylic acid The 7α-methylthiocephem (from Example 61(a)) (131 mg) in dimethylformamide (5 ml) was cooled to −20° and treated successively with mercuric acetate (68 mg) and O-t-butyldiphenylsilylhydroxylamine (58 mg). The resultant clear solution was warmed to room temperature over 1 hour and ethyl acetate (75 ml) was added. The solution was washed with 2N hydrochloric acid (4×25 ml) and saturated sodium chloride (2×25 ml), dried (Na$_2$SO$_4$) and evaporated in vacuo to give the title compound (169 mg) as a yellow solid.

I.R. (KBr) 1785 cm$^{-1}$.

N.M.R. (DMSO-d$_6$)δ=0.94 (m, 9H); 3.04–3.61 (m, 4H); 3.76–3.97 (m, 2H); 3.87 (s, 3H); 4.14 and 4.32 (ABq, J=12, 2H); 4.57 (s, 2H); 4.98 (s, 1H); 5.71 (d, J=6, 1H); 7.02 (s, 1H); 7.17–7.82 (m, 20H); 9.84 (d, J=9, NH); 9.89 (s, 1H).

(c) 7β-[D-2-(4-Benzyl-2,3-dioxopiperazin-1-ylcarbonylamino)-2-phenylacetamido]-7α-hydroxyamino-3-[(1-methyl-1H-tetrazol-S-yl)thiomethyl[ceph-3-em-4-carboxylic acid The title compound (85 mg) was prepared from the product of Example 61(b) (169 mg) by the method described in Example 59(d).

I.R. (KBr) 1785 cm$^{-1}$. N.M.R. (DMSO-d$_6$)δ=2.95–3.68 (m, 4H); 3.75–3.99 (m, 2H); 3.89 (s, 3H); 4.09 and 4.33 (ABq, J=12, 2H); 4.57 (s, 2H); 4.98 (s, 1H); 5.66 (d, J=6, 1H); 7.08–7.58 (m, 10H); 8.18 (brs., 1H); 9.52 (s, 1H); 9.86 (d, J=9, NH).

EXAMPLES 62–68

The following compounds of the formula (I) were prepared from the appropriate starting materials using the method of Example 61 parts (a) to (c).

| Example No. and side chain stereo-chemistry | R | R¹ | R² | I.R. (KBr) cm⁻¹ | N.M.R. (DMSO—d₆) |
|---|---|---|---|---|---|
| 62 D- | Ph— | -C(=O)-N⟨CH₂CH₂⟩N-benzyl (2-oxoimidazolidinyl) | -CH₂-S-(1-(2-hydroxyethyl)-tetrazol-5-yl) | 1785 | δ = 2.85–4.01 (m, 8H); 4.09 and 4.38 (ABq, J = 12, 2H); 4.21–4.37 (m, 2H); 4.57 (s, 2H); 4.96 (s, 1H); 5.66 (d, J = 6, 1H); 7.12–7.61 (m, 10H); 9.53 (s, 1H); 9.86 (d, J = 9, NH); |
| 63 D- | Ph— | -C(=O)-N⟨CH₂CH₂⟩N-Et (2-oxoimidazolidinyl) | -CH₂-S-(2-hydroxyphenyl-benzothiazol-2-yl) | 1780 | δ = 1.06 (t, J = 6Hz, 3H); 3.19 (½ ABq, J = 18Hz, 1H); 3.23–3.52 (m, 5H); 3.87 (m, 2H); 4.09 and 4.64 (ABq, J = 12Hz, 2H); 4.99 (s, 1H); 5.66 (d, J = 6Hz, 1H); 6.87–7.66 (m, 10H); 9.54 (s, 1H); 9.79 (br. 1H); 9.86 (d, J = 6Hz, NH). |
| 64 D- | Ph— | -C(=O)-N⟨CH₂CH₂⟩N-benzyl | -CH₂-S-benzothiazol-2-yl | 1780 | δ = 2.84–4.01 (m, 6H); 4.13 and 4.74 (ABq, J = 12, 2H); 4.59 (s, 2H); 5.00 (s, 1H); 5.66 (d, J = 9, 1H); 7.04–7.62 (m, 12H); 7.87 (d, J = 6, 1H); 8.01 (d, J = 6, 1H); 8.18 (brs. 1H); 9.54 (s, 1H); 9.87 (d, J = 6, NH). |
| 65 D- | Ph— | -C(=O)-N⟨CH₂CH₂⟩N-benzyl | -CH₂-S-(5-methyl-1,3,4-thiadiazol-2-yl) | 1785 | δ = 2.67 (s, 3H); 3.22 and 3.56 (ABq, J = 12, 2H); 3.42–3.56 (m, 2H); 3.76–3.99 (m, 2H); 4.10 and 4.47 (ABq, J = 15, 2H); 4.59 (s, 2H); 5.01 (s, 1H); 5.67 (d, J = 9, 1H); 6.99–7.61 (m, 10H); 9.55 (s, 1H); 9.88 (d, J = 6, NH). |
| 66 D- | Ph— | -C(=O)-N⟨CH₂CH₂⟩N-benzyl | -CH₂-S-(1-carboxymethyl-tetrazol-5-yl) (CH₂COOH) | 1785 | δ = 3.02–3.87 (m, 4H); 3.89–3.97 (m, 2H); 4.10 and 4.44 (ABq, J = 15, 2H); 4.58 (s, 2H); 4.94 (s, 1H); 5.25 and 5.29 (ABq, J = 12, 2H); 5.66 (d, J = 6, 1H); 7.03–7.58 (m, 10H); 9.53 (s, 1H); 9.86 (d, J = 6, NH). |
| 67 D- | Ph— | -C(=O)-N⟨CH₂CH₂⟩N-Et | -CH₂-S-thiazol-2-yl | 1785 | δ = 1.02 (t, J = 6, 3H); 3.08–3.78 (m, 6H + HOD); 3.87 (m, 2H); 4.06 and 4.42 (ABq, J = 12, 2H); 4.97 (s, 1H); 5.67 (d, J = 6, 1H); 7.12–7.58 (m, 5H) 7.61–7.78 (m, 2H); 9.56 (s, 1H); 9.86 (d, J = 6, NH). |
| 68 D- | Ph— | -C(=O)-N⟨CH₂CH₂⟩N-Et | -CH₂-S-(4-methyl-thiazol-2-yl) | 1785 | δ = 1.05 (t, J = 6, 3H); 2.48 (s, 3H); 2.98–3.63 (m, 6H); 3.87 (m, 2H); 4.13 and 4.56 (ABq, J = 15, 2H); 5.00 (s, 1H); 5.66 (d, J = 9, 1H); 7.16–7.57 (m, 5H); 8.17 (brs. 1H); 9.53 (s, 1H); 9.86 (d, J = 9, NH). |

EXAMPLE 69

3-[(1-Carboxymethyl-1H-tetrazol-5-ylthiomethyl]-7β-[(2R,3S)-3-hydroxy-2-(2-oxo-3-methanesulphonylimidazolidin-1-ylcarbonylamino)butanamido[-7α-hydroxyaminoceph-3-em-4-carboxylic acid (a) (2R,3S)-3-Hydroxy-2-(2-oxo-3-methanesulphonylimidazolidin-1-ylcarbonylamino)butanoic acid D-Threonine (5.0 g) was suspended in water (50 ml) and treated with 2M aqueous sodium hydroxide solution to pH 10, forming a clear solution. The pH was then re-adjusted to 7.5 with concentrated hydrochloric acid and the still clear solution cooled to 15°. 3-Methanesulphonyl-2-oxoimidazolidine-1-carbonyl chloride (9.5 g) was then added portionwise over 2 minutes, with simultaneous addition of 2M aqueous sodium hydroxide to maintain the pH at 6.0–7.5. Following this, acetone (30 ml) was added to give a clear solution which was then stirred at room temperature for 1 hour whilst still maintaining the pH at 6.0–7.5. After evaporation of the acetone in vacuo the aqueous residue was extracted well with ethyl acetate and the organic extracts were discarded. The pH of the aqueous phase was then adjusted to 1.5 with concentrated hydrochloric acid and the mixture was extracted using 3×50 ml portions of ethyl acetate:tetrahydrofuran (1:1). The organic extracts were dried and the solvent was evaporated to give the title compound as a white solid, (7.3 g).

I.R. (KBr) 1735 cm$^{-1}$.

N.M.R. (DMSO-d$_6$)δ1.08 (d, J=6, 3H); 3.35 (s, 3H); 3.72–3.85 (m, 4H); 4.11–4.21 (m, 2H); 8.21 (d, J=8, NH).

(b) Benzhydryl 3-acetoxymethyl-7β-[(2R,3S)-3-hydroxy-2-(2-oxo-3-methanesulphonylimidazolidin-1-ylcarbonylamino)butanamido]-7α-methylthioceph-3-em-4-carboxylate The product from the previous step (69(a)) was coupled to benzhydryl 7β-amino-7α-methylthiocephalosporanate (9.5 g) by the procedure used for Example 46(a). Silica gel chromatography (methylene chloride-ethyl acetate gradient) gave the title compound as a yellow foam, (6.5 g).

I.R. (KBr) 1785 cm$^{-1}$.

N.M.R. (CDCl$_3$)δ=1.29 (d, J=6, 3H); 2.05 (s, 3H); 2.36 (s, 3H); 2.94 and 3.33 (ABq, J=21, 2H); 3.01 (d, J=3, 1H exch.); 3.35 (s, 3H); 3.96 (s, 4H); 4.43–4.49 (m, 2H); 4.90 and 5.14 (ABq, J=13, 2H); 4.97 (s, 1H); 6.92 (s, 1H); 7.29–7.50 (m, 11H, 2×C$_6$H$_5$ and CONH); 8.62 (d, J=6, CHNH).

(c) 3-Acetoxymethyl-7β-[(2R,3S)-3-hydroxy-2-(2-oxo-3-methanesulphonylimidazolidin-1-ylcarbonylamino)butanamido]-7α-methylthioceph-3-em-4-carboxylic acid Treatment of the benzhydryl ester (from Example 69(b)) (4.5 g) with trifluoroacetic acid and anisole as in Example 57(a) gave the title compound (2.85 g) as a white solid from dichloromethane-diethyl ether.

I.R. (KBr) 1785 cm$^{-1}$.

N.M.R. (DMSO-d$_6$)δ=1.09 (d, J=6, 3H); 2.02 (s, 3H); 2.26 (s, 3H); 3.36 (s, 3H); 3.38 and 3.59 (ABq, J=18, 2H); 3.74–3.84 (m, 4H); 3.96–4.00 (m, 1H); 4.29–4.35 (m, 1H); 4.65 and 4.95 (ABq, J=14, 2H); 5.06 (s, 1H); 8.25 (d, J=7, NH); 9.17 (s, 1H).

(d) 3-[(1-Carboxymethyl-1H-tetrazol-5-yl)thiomethyl]-7β-[(2R,3S)-3-hydroxy-2-(2-oxo-3-methanesulphonylimidazolidin-1-ylcarbonylamino)butanamido]-7α-methylthioceph-3-em-4-carboxylic acid The product from the previous Example (69(c) (426 mg) was reacted with 1-carboxymethyl-1H-tetrazole-5-thiol (134 mg) as in Example 9(a) to afford the title compound as a light buff solid after trituration with diethyl ether (20 ml) (310 mg).

I.R. (KBr) 1780 cm$^{-1}$.

N.M.R. (DMSO-d$_6$)δ=1.08 (d, J=6, 3H); 2.23 (s, 3H); 3.20–3.49 (m, 5H); 3.73–3.79 (m, 4H); 3.97 (m, 1H); 4.16 and 4.45 (ABq, J=14, 2H); 4.27–4.28 (m, 1H); 4.98 (s, 1H); 5.04–5.05 (m, 1H exch.); 5.29–5.30 (m, 2H); 8.23 (d, J=6, NH); 9.17 (s, 1H, exch.).

(e) 7α-[t-Butyldiphenylsilyloxyamino)-3-[(1-carboxymethyl-1H-tetrazol-5-yl)thiomethyl]-7β-[(2R,3S)-3-hydroxy-2-(2-oxo-3-methanesulphonylimidazolidin-1-ylcarbonylamino)butanamido]ceph-3-em-4-carboxylic acid A solution of the 7α-methylthiocephem (from Example 69(d)) (310 mg) in dimethylformamide (5 ml) was cooled to −30° and treated with mercuric acetate (280 mg), followed by O-t-butyldiphenylsilylhydroxylamine (143 mg). The clear solution was warmed to 0° during 0.5 hours, added to 0.5M hydrochloric acid (25 ml) and extracted with 2×20 ml portions of ethyl acetate:tetrahydrofuran (2:1). The combined organic extracts were washed with 3×20 ml water, 1×20 ml brine, dried and the solvent was evaporated to give a light brown solid. Trituration with diethyl ether afforded the title comlpound (210 mg).

I.R. (KBr) 1785 cm$^{-1}$.

N.M.R. (DMSO-d$_6$)δ=0.96 (s, 9H); 1.08 (d, J=6, 3H); 3.35 (s, 3H); 3.37–3.79 (m, 6H); 4.02 (brs., 1H); 4.19 and 4.38 (ABq, J=12, 2H); 4.34 (m, 1H); 4.99 (s, 1H); 5.00 (brs., 1H exch.); 5.27 (s, 2H); 6.98 (s, 1H); 7.35–7.66 (m, 10H); 8.24 (d, J=7, NH); 9.33 (s, 1H).

(f) 3-[(1-Carboxymethyl-1H-tetrazol-5-ylthiomethyl]-7α-hydroxyamino-7β-[(2R,3S)-3-hydroxy-2-[2-oxo-3-methanesulphonylimidazolidin-1-ylcarbonylamino)-butanamido]ceph-3-em-4-carboxylic acid The protected hydroxylamine derivative from the previous step (69(e)) (205 mg) in acetonitrile:tetrahydrofuran (4 ml of 1:1) was cooled to 0°–5° and then treated with 40% aqueous hydrofluoric acid (0.25 ml). After 0.5 hours the solution was evaporated to dryness in vacuo, the residue dissolved in 1:1 isopropanol:methanol (20 ml), and again evaporated. The crude product was dissolved in methanol (10 ml), filtered and the solution was evaporated to about 2 ml. It was then added dropwise to stirred diethyl ether (25 ml) giving the title compound as a white solid after filtration and drying in vacuo, (137 mg).

I.R. (KBr) 1780 cm$^{-1}$.

N.M.R. (DMSO-d$_6$)δ=1.08 (d, J=6, 3H); 3.35 (s, 3H); 3.42–3.89 (m, 6H); 4.02–4.03 (m, 1H); 4.15 and 4.41 (ABq, J=15, 2H); 4.32–4.34 (m, 1H); 5.03 (s, 1H); 5.30 (s, 2H); 8.26 (d, J=6, CHNH); 8.92 (s, 1H).

EXAMPLE 70

3-Acetoxymethyl-7β-[(2R,3S)-3-hydroxy-2-(2-oxo-3-methanesulphonylimidazolidin-1-ylcarbonylamino)-butanamido]-7α-hydroxyaminoceph-3-em-4-carboxylic acid (a) 3-Acetoxymethyl-7α-(t-butyldiphenylsilyloxyamino)-7β-[(2R,3S)-3-hydroxy-2-(2-oxo-3-methanesulphonylimidazolidin-1-ylcarbonylamino)-butanamido]ceph-3-em-4-carboxylic acid The title compound (315 mg) was prepared by reaction of the 7-methylthiocephem (from Example 69(c)) (305 mg) with O-t-butyldiphenylsilylhydroxylamine and mercuric acetate as previously described in Example 69(e).

I.R. (KBr) 1790 cm$^{-1}$.

N.M.R. (DMSO-d$_6$)δ=0.99 (s, 9H); 1.11 (d, J=6, 3H); 2.02 (s, 3H); 3.33 and 3.52 (ABq, J=18, 2H); 3.34 (s, 3H); 3.67–3.78 (m, 4H); 4.01–4.05 (m, 1H); 4.34–4.37 (m, 1H+1H exch.); 4.66 and 4.93 (ABq, J=12, 2H); 5.03 (s, 1H); 7.02 (s, 1H); 7.31–7.69 (m, 10H); 8.27 (d, J=8, CHNH); 9.33 (s, 1H).

(b) 3-Acetoxymethyl-7β-[(2R,3S)-3-hydroxy-2-(2-oxo-3-methanesulphonylimidazolidin-1-ylcarbonylamino)-butanamido]-7α-hydroxyaminoceph-3-em-4-carboxylic acid The protected 7α-hydroxyaminocephem from the previous Example (70(a)) (310 mg) was treated with 40% aqueous hydrofluoric acid by the procedure given previously in Example 69(f). Trituration of the crude product with dichloromethane (10 ml) at 0° gave the title compound as a near-white solid, (205 mg).

I.R. (KBr) 1785 cm$^{-1}$.

N.M.R. (DMSO-d$_6$)δ=1.09 (d, J=6, 3H); 2.02 (s, 3H); 3.35 (s, 3H); 3.32 and 3.52 (ABq, J=18, 2H); 3.77–3.83 (m, 4H); 4.02–4.05 (m, 1H); 4.31–4.35 (m, 1H); 4.61 and 4.90 (ABq, J=14, 2H); 5.10 (s, 1H); 8.26 (d, J=7, CHNH); 8.90 (s, 1H exch.).

EXAMPLE 71

7β-[D-2-(4-Benzyl-2,3-dioxopiperazin-1-ylcarbonylamino)-2-phenylacetamido]-3-[(5-carboxymethyl-4-methylthiazol-2-yl)thiomethyl]-7α-hydroxyaminoceph-3-em-4-carboxylic acid (a) 7β-[D-2-(4-Benzyl-2,3-dioxopiperazin-1-ylcarbonylamino)-2-phenylacetamido]-3-[(5-carboxymethyl-4-methylthiazol-2-yl)thiomethyl]-7α-methylthioceph-3-em-4-carboxylic acid The title compound (155 mg) was prepared by reaction of the corresponding 3-acetoxymethylcephem (Example 59(a)) (204 mg) with 5-carboxymethyl-4-methylthiazole-2-thiol (85 mg) by the method described previously in Example 9(a).

I.R. (KBr) 1785 cm$^{-1}$.

N.M.R. (DMSO-d$_6$)δ=2.19 (s, 6H, 2×CH$_3$); 3.22–3.58 (m, 4H); 3.73 (s, 2H); 3.86–3.87 (m, 2H) 3.98 and 4.46 (ABq, J=16, 2H); 4.58 (s, 2H); 5.02 (s, 1H); 5.62 (d, J=7, C$\underline{H}$NH); 7.25–7.44 (m, 10H); 9.66 (s, 1H); 9.82 (d, J=7, N$\underline{H}$).

(b) 7β-[D-2-(4-Benzyl-2,3-dioxopiperazin-1-ylcarbonylamino)-2-phenylacetamido]-7αt-butyldiphenylsilyloxyamino-3[(5-carboxymethyl-4-methylthiazol-2-yl)thiomethyl]ceph-3-em-4-carboxylic acid The 7α-methylthiocephem from the preceeding example (71(a)) (280 mg) was treated with mercuric acetate and O-t-butyldiphenylsilylhydroxylamine as described previously for Example 69(e). Trituration of the crude product with diethyl ether gave the title compound (255 mg).

I.R. (KBr) 1785 cm$^{-1}$.

N.M.R. (DMSO-d$_6$) δ=0.96 (s, 9H); 2.19 (s, 3H); 3.11–3.45 (m, 4H); 3.72 (s, 2H); 3.86 (m, 2H); 4.00 and 4.46 (ABq, J=16, 2H); 4.58 (s, 2H); 4.98 (s, 1H); 5.71 (d, J=7, C$\underline{H}$NH); 7.02 (s, 1H); 7.29–7.68 (m, 20H); 9.84–9.88 (m, 2H).

(c) 7β-[D-2-(4-Benzyl-2,3-dioxopiperazin-1-ylcarbonylamino)-2-phenylacetamido]-3-[(5-carboxymethyl-4-methylthiazol-2-yl)thiomethyl]-7α-hydroxyaminoceph-3-em-4-carboxylic acid Deprotection of the 7α-t-butyldiphenylsilyloxyaminocephem obtained in the above example (71(b)) (250 mg) with 40% aqueous hydrofluoric acid, as described previously for Example 69(f), afforded the title compound as a white solid (172 mg).

I.R. (KBr) 1785 cm$^{-1}$.

N.M.R. (DMSO-d$_6$) δ=2.19 (s, 3H); 3.15 and 3.56 (ABq, J=18, 2H); 3.47 (m, 2H); 3.73 (s, 2H); 3.86–3.87 (m, 2H); 3.96 and 4.42 (ABq, J=16, 2H); 4.57 (s, 2H); 4.98 (s, 1H); 5.66 (d, J=7, C$\underline{H}$NH); 7.30–7.45 (m, 10H); 9.53 (s, 1H); 9.87 (d, J=7, C$\underline{H}$N$\underline{H}$).

EXAMPLE 72

7β-[D-2-(4-Benzyl-2,3-dioxopiperazin-1-ylcarbonylamino)-2-phenylacetamido]-3-[(5-carboxymethyl-4H-1,2,4-triazol-3-yl)thiomethyl]-7α-hydroxyaminoceph-3-em-4-carboxylic acid (a) 7β-[D-2-(4-Benzyl-2,3-dioxopiperazin-1-ylcarbonylamino)-2-phenylacetamido]-3-[(5-carboxymethyl-4H-1,2,4-triazol-3-yl)thiomethyl]-7α-methylthioceph-3-em-4-carboxylic acid The 3-acetoxymethylcephem obtained in Example 59(a) (204 mg) was suspended in water (7 ml) and acetone (3 ml) and treated with 5-carboxymethyl-4H-1,2,4-triazole-3-thiol (57 mg). Sodium bicarbonate (55 mg) was added to give a clear solution (pH 6.5) which was heated at 60° under nitrogen atmosphere for 5 hours with the addition of 5% aqueous sodium bicarbonate to maintain the pH at 6.0–6.5. The solution was cooled to room temperature, extracted with ethyl acetate and the organic extracts discarded. The aqueous phase was then acidified (pH 2) with a concentrated hydrochloric acid and the precipitated oily solid was extracted with 2×20 ml portions of ethyl acetate/tetrahydrofuran. The extracts were dried and evaporated giving a pale yellow solid which, on trituration with ethyl acetate (5 ml), gave the title compound as a white solid (115 mg).

I.R. (KBr) 1780 cm$^{-1}$.

N.M.R. (DMSO-d$_6$) δ=2.20 (s, 3H); 3.23–4.27 (m, 11H, 2×piperazine C$\underline{H}_2$, C$_2$-2$\underline{H}$, CH$_2$S-Het-C$\underline{H}_2$CO$_2$H) and triazole N$\underline{H}$); 4.59 (s, 2H); 5.01 (s, 1$\underline{H}$); 5.62 (d, J=7), C$\underline{H}$N$\underline{H}$); 7.32–7.45 (m, 10H); 9.67 (s, 1H); 9.83 (d, J=7, N$\underline{H}$).

(b) 7β-[D-2-(4-Benzyl-2,3-dioxopiperazin-1-ylcarbonylamino)-2-phenylacetamido]-7α-t-butyldiphenylsilyloxyamino-3-[(5-carboxymethyl-4H-1,2,4-triazol-3-yl)thiomethyl]ceph-3-em-4-carboxylic acid The product from the preceeding example (72(a)) (100 mg) was treated with mercuric acetate and O-t-butyldiphenylsilylhydroxylamine as described previously for Example 69(e). Trituration of the crude product with diethyl ether (5 ml) gave the title compound as a white solid (87 mg).

I.R. (KBr) 1785 cm$^{-1}$.

N.M.R. (DMSO-d$_6$) δ=0.95 (s, 9H); 3.09–3.45 (m, 6H, C$_2$-2$\underline{H}$, piperazine C$\underline{H}_2$ and Het-C$\underline{H}_2$CO$_2$H); 3.73 (s, 1H); 3.83–3.86 (m, 2H); 3.95 and 4.21 (ABq, J=16, 2H); 4.57 (s, 2H); 4.97 (s, 5.70 (d, J=7, C$\underline{H}$NH); 7.00 (s, 1H); 7.27–7.67 (m, 20H); 9.85 (d, J=7, N$\underline{H}$); 9.89 (s, 1H).

(c) 7β-[D-2-(4-Benzyl-2,3-dioxopiperazin-1-ylcarbonylamino)-2-phenylacetamido]-3-[(5-carboxymethyl-4H-1,2,4-triazol-3-yl)thiomethyl]-7α-hydroxyaminoceph-3-em-4-carboxylic acid Deprotection of the 7α-t-butyldiphenylsilyloxyamino-cephem obtained in the previous example (72(b)) (80 mg) with 40% aqueous hydrofluoric acid, as described for Example 69(f), gave the title compound, (47 mg).

I.R. (KBr) 1780 cm$^{-1}$.

N.M.R. (DMSO-d$_6$) δ=3.11–4.35 (m, 11H, C$_2$-2$\underline{H}$, 2×piperazine C$\underline{H}_2$, C$\underline{H}_2$S-Het-C$\underline{H}_2$CO$_2$H and triazole N$\underline{H}$); 4.57 (s, 2$\underline{H}$); 4.96 (s, 1H); 5.65 (d, J=6, C$\underline{H}$NH); 6.45 (s, 1H); 7.25–7.44 (m, 10H); 8.13 (s, 1H); 9.53 (s, 1H); 9.86 (d, J=6, CHN$\underline{H}$).

EXAMPLE 73

(a) 7β-[D-2-(4-Benzyl-2,3-dioxopiperazin-1-ylcarbonylamino)-2-phenylacetamido]-7α-methylthio-3-[(1-potassiumsulphomethyl-1H-tetrazol-5-yl)thiomethyl]-ceph-3-em-4-carboxylic acid 7β-[D-2-(4-Benzyl-2,3-dioxopiperazin-1-ylcarbonylamino)-2-phenylacetamido]-7α-methylthiocephalosporanic acid (Example 59(a)) (306 mg) was treated with 1-sulphomethyl-1H-tetrazole-5-thiol sodium salt (196 mg) in a similar manner to that described in Example 36(a) to give the title compound (278 mg).

I.R. (KBr) 1780 cm$^{-1}$.

N.M.R. (DMSO-d$_6$) δ=2.18 (s, 3H); 3.16 and 3.56 (ABq, J=9, 2H); 3.41–3.55 (m, 2H); 3.80–3.97 (m, 2H); 4.05 and 4.43 (ABq, J=9, 2H); 4.57 (s, 2H); 4.88–5.13 (m, 3H); 5.61 (d, J=6, 1H); 7.16–7.62 (m, 10H); 9.65 (s, 1H); 9.80 (d, J=6, NH).

(b) 7β-[D-2-(4-Benzyl-2,3-dioxopiperazin-1-ylcarbonylamino)-2-phenylacetamido]-7α-(t-butyldiphenylsilyloxyamino)-3-[(1-sulphomethyl-1H-tetrazol-5-yl)thiomethyl]ceph-3-em-4-carboxylic acid The title compound (208 mg) was prepared from the 7-methylthiocephem (Example 73(a)) (272 mg) by the method described in Example 61(b).

I.R. (KBr) 1785 cm$^{-1}$.

N.M.R. (DMSO-d$_6$) δ=0.96 (s, 9H); 3.09–3.62 (m, 4H); 3.78–3.97 (m, 2H); 4.07 and 4.38 (ABq, J=12, 2H); 4.58 (s, 2H); 4.88–5.10 (m, 3H); 5.71 (d, J=6, 1H); 7.02 (s, 1H); 7.16–7.82 (m, 20H); 9.86 (d, J=6, NH); 9.92 (s, 1H).

(c) 7β-[D-2-(4-Benzyl-2,3-dioxopiperazin-1-ylcarbonylamino)-2-phenylacetamido]-7α-hydroxyamino-3-[(1-sulphomethyl-1H-tetrazol-5-yl)thiomethyl]ceph-3-em-4-carboxylic acid The title compound (58 mg) was prepared from the product of Example 73(b) (200 mg) by the method described in Example 59(d).

I.R. (KBr) 1790 cm$^{-1}$.

N.M.R. (DMSO-d$_6$) δ=2.95–3.78 (m, 4H+HOD); 3.79–3.96 (m, 2H); 4.02 and 4.41 (ABq, J=12, 2H); 4.58 (s, 2H); 4.87–5.13 (m, 3H); 5.67 (d, J=6, 1H); 7.01–7.62 (m, 10H); 9.56 (s, 1H); 9.86 (d, J=6, NH).

EXAMPLE 74

7β-[D-2-(4-Ethyl-2,3-dioxopiperazin-1-ylcarbonylamino)-2-phenylacetamido]-7α-hydroxyamino-3-[(4-carboxy-3-hydroxyisothiazol-5-yl)thiomethyl]ceph-3-em-4-carboxylic acid (a) 7β-[D-2-(4-Ethyl-2,3-dioxopiperazin-1-ylcarbonylamino)-2-phenylacetamido]-7α-methylthio-3-[(4-carboxy-3-hydroxyisothiazol-5-yl)thiomethyl]ceph-3-em-4-carboxylic acid This compound was prepared from the appropriate starting materials by the method of Example 9(a).

I.R. (KBr) 1770 cm$^{-1}$.

N.M.R. (DMSO-d$_6$) δ=1.05 (t, J=7, 3H); 2.25 (s, 3H); 2.9–3.9 (m, 8H+HOD); 3.95 and 4.25 (2H, ABq, J=12); 5.1 (s, 1H); 5.65 (d, J=6, 1H); 7.2–7.5 (m, 5H); 9.65 (s, NH); 9.8 (d, J=6, NH).

(b) 7β-[D-2-(4-Ethyl-2,3-dioxopiperazin-1-ylcarbonylamino)-2-phenylacetamido]-7α-t-butyldiphenylsilyloxyamino-3-[(4-carboxy-3-hydroxyisothiazol-5-yl)thiomethyl]ceph-3-em-4-carboxylic acid The above compound was prepared from the product from the previous step (74(a)) by the method of Example 59(c).

I.R. (KBr) 1770 cm$^{-1}$.

N.M.R. (DMSO-d$_6$) δ=0.95 (s, 9H); 1.05 (t, J=7, 3H); 3.1–4.3 (m, 10+HOD); 4.81 (s, 1H); 5.75 (d, J=6, 1H); 6.95 (s, NH-OH); 7.2–7.8 (m, 15H); 9.75 (s, NH); 9.85 (d, J=6, NH).

(c) 7β-[D-2-(4-Ethyl-2,3-dioxopiperazin-1-ylcarbonylamino)-2-phenyl acetamido]-7α-hydroxyamino-3-[(4-carboxy-3-hydroxyisothiazol-5-yl)thiomethyl]ceph-3-em-4-carboxylic acid The above compound was prepared from the product of the previous step (74(b)) by the method of Example 59(d).

I.R. (KBr) 1780 cm$^{-1}$.

N.M.R. (DMSO-d$_6$) δ=1.03 (t, J=7, 3H); 3.1–3.7 (m, 6H); 3.85–3.90 (m, 2H); 3.95 and 4.2 (2H, ABq, J=12); 5.03 (s, 1H); 5.66 (d, J=6, 1H); 6.5 (brs, NH-OH); 7.1–7.5 (m, 5H); 8.18 (s, NHOH); 9.54 (s, NH); 9.86 (d, J=6, NH).

EXAMPLE 75

7β-[2-(R)-(4-Ethyl-2,3-dioxopiperazin-1-ylcarbonylamino)-3-(S)-hydroxybutanamido]-7α-hydroxyamino-3-[(1-potassiumsulphomethyl-1H-tetrazol-5-yl)thiomethyl]-ceph-3-em-4-carboxylate acid (a) 7β-[2-(R)-(4-Ethyl-2,3-dioxopiperazin-1-ylcarbonylamino)-3-(S)-t-butyldimethylsilyloxybutanamido]-7α-methylthiocephalosporanic acid A suspension of 7β-[2-(R)-(4-ethyl-2,3-dioxopiperazin-1-ylcarbonylamino)-3-(S)-hydroxybutanamido]-7α-methylthiocephalosporanic acid (2.0 g) in methylene chloride (50 ml) was stirred at room temperature under a nitrogen atmosphere and treated with 2,6-lutidine (1.19 ml) to give a clear solution. To this solution was added t-butyldimethylsilyltrifluoromethylsulphonate (2.35 ml) and the mixture was stirred for five minutes, washed with 1M hydrochloric acid, dried (MgSO$_4$) and evaporated to dryness. The residue was triturated with hexane and filtered to give the title compound (1.56 g).

I.R. (KBr) 1786 cm$^{-1}$.

N.M.R. (DMSO-d$_6$) δ=0.05 (s, 6H); 0.85 (s, 9H); 1.08 (t, 3H, J=6); 1.14 (d, 3H, J=6); 2.02 (s, 3H); 2.24 (s, 3H); 3.29 to 3.62 (m, 6H); 3.91 (m, 2H); 4.20 (m, 1H); 4.41 (m, 1H); 4.64 and 4.94 (ABq, 2H, J=12); 5.02 (s, 1H); 9.03 (s, 1H); 9.30 (d, 1H, J=6).

(b) 7β-[2-(R)-(4-Ethyl-2,3-dioxopiperazin-1-ylcarbonylamino)-3-(S)-t-butyldimethylsilyloxybutanamido]-7α-methylthio-3-[(1-potassiumsulphomethyl-1H-tetrazol-5-yl)thiomethyl]-ceph-3-em-4-carboxylic acid This compound was prepared from the product of the previous step by the method of Example 36(a) using appropriate starting materials.

I.R. (KBr) 1783 cm$^{-1}$.

N.M.R. (DMSO-d$_6$) δ=0.04 (s, 6H); 0.83 (s, 9H); 1.07 (t, 3H); J=6); 1.14 (d, 3H, J=6); 2.23 (s, 3H); 3.29 to 3.72 (m, 6H); 3.88 (m, 2H); 4.05 and 4.47 (ABq, 2H, J=15); 4.19 (m, 1H); 4.40 (m, 1H); 4.95 (m, 2H); 4.99 (s, 1H); 9.05 (s, 1H); 9.27 (d, 1H, J=9).

(c) 7β-[2-(R)-(4-Ethyl-2,3-dioxopiperazin-1-ylcarbonylamino(-3-(S)-t-butyldimethylsilyloxybutanamido]-7α-hydroxyamino-3-[(1-potassiumsulphomethyl-1H-tetrazol-5-yl)thiomethyl]-ceph-3-em-4-carboxylic acid This compound was prepared from the product of the previous step by the method of Example 9(b).

I.R. (KBr) 1780 cm$^{-1}$.

N.M.R. (DMSO-d$_6$) δ=0.03 (s, 6H); 0.84 (s, 9H); 1.08 (t, 3H, J=6); 1.18 (d, 3H, J=6); 3.21 to 3.63 (m, 6H); 3.90 (m, 2H); 4.08 to 4.48 (m, 4H); 4.99 (m, 3H); 6.38 (brs, 1H); 7.95 (s, 1H); 8.83 (brs, 1H); 9.31 (d, 2H, J=6).

(d) 7β-[2-(R)-(4-Ethyl-2,3-dioxopiperazin-1-ylcarbonylamino)-3-(S)-hydroxybutanamido]-7α-hydroxyamino-3-[(1-potassiumsulphomethyl-1H-tetrazol-5-yl)-thiomethyl]-ceph-3-em-4-carboxylic acid A suspension of the silylated cephem of part (c) (80 mg) in acetonitrile (5 cm$^3$) was treated with aqueous hydrogen fluoride (2 ml of 40% HF) in a dropwise manner over two minutes to give a clear solution. The mixture was stirred for five minutes, evaporated to dryness, the residue taken up in methanol (5 cm$^3$), filtered, evaporated to dryness, triturated with methylene chloride and the solid separated by filtration to give the title compound, (38 mg).

I.R. (KBr) 1785 cm$^{-1}$.

N.M.R. (DMSO-d$_6$) δ=1.06 (m, 6H); 3.36 to 4.40 (m, 12H); 4.98 (m, 3H); 8.96 (s, 1H); 9.26 (d, 1H, J=6).

EXAMPLE 76

3-Acetoxymethyl-7β-[DL-2-[3-(2-hydroxyethyl)-2-oxoimidazolidin-1-ylcarbonylamino]-2-phenylacetamido]-7α-hydroxyaminoceph-3-em-4-carboxylic acid (a) 1-(2-t-Butyldiphenylsilyloxyethyl)-2-oxoimidazolidine A solution of 1-(2-hydroxyethyl)-2-oxoimidazolidine (13 g) in dimethylformamide (50 ml) containing imidazole (7.5 g) was treated with t-butylchlorodiphenylsilane (28.6 ml) and the clear solution stirred for 3 hours at ambient temperature. The white suspension formed was dissolved in water (200 ml) and ethyl acetate (500 ml). The aqueous phase was re-extracted with ethyl acetate (100 ml) and the combined organic phases were washed with 3×100 ml portions of water, 1×100 ml brine, dried and evaporated to give a solid. Trituration of the solid with diethyl ether (100 ml) afforded the title compound as a white solid, (33.7 g).

I.R. (KBr) 1680 cm$^{-1}$.

N.M.R. (CDCl$_3$) δ=1.08 (s, 9H); 3.35–3.42 (m, 4H); 3.57–3.62 (m, 2H); 3.81 (t, J=s, 2H); 4.47 (brs., 1H); 7.38–7.69 (m, 10H).

(b) 3-(2-t-Butyldiphenylsilyloxyethyl)-2-oxoimidazolidine-1-carbonyl chloride

The product from the previous step (7.36 g) in 1,2-dichloroethane (50 ml) was treated with N-trimethylsilyldiethylamine (7.6 g) and the solution was heated at reflux for 0.5 hours. After cooling the solvent was removed by evaporation in vacuo and the residue was re-evaporated from 2×50 ml portions of carbon tetrachloride to give the 1-trimethylsilyl derivative as a light orange oil (8.8 g). This was dissolved in dry dichloromethane (50 ml) and treated with 2,2,2-trichloroethyl chloroformate (1.33 ml). The solution was stirred 18 hours at ambient temperature, evaporated to dryness and the residue re-evaporated from 2×50 ml portions of dichloromethane/carbon tetrachloride (1:1) to afford the title compound as an orange-brown foam (8.45 g).

I.R. (film) 1805 cm$^{-1}$.

N.M.R. (CDCl$_3$) δ=1.05 (s, 9H); 3.27–3.96 (m, 8H); 7.15–7.60 (m, 10H).

(c) D-2-[3-(2-t-butyldiphenylsilyloxyethyl)-2-oxoimidazolidin-1-ylcarbonylamino]-2-phenylacetic acid D-phenylglycine (3.02 g) and N,N-diethyltrimethylsilylamine (15.1 ml) were stirred at reflux for 5 hours and the resultant clear solution was evaporated to dryness in vacuo. The residue was re-evaporated from 2×40 ml portions of carbon tetrachloride giving a viscous oil. This oil was dissolved in dichloromethane (10 ml) and added dropwise over 2 minutes to a precooled (−20°) solution of 3-(2-t-butyldiphenylsilyloxyethyl)-2-oxoimidazolidine-1-carbonylchloride from part (b) (8.45 g) in dichloroethane (30 ml). The solution was warmed to 20° over 1 hour, stirred for 18 hours then washed with water (3×20 ml), dried and evaporated to dryness in vacuo. The crude product was purified by silica gel chromatography (dichloromethane-isopropanol gradient) to give the title compound as a white foam, (8.7 g).

I.R. (KBr) 1740 cm$^{-1}$.

N.M.R. (CDCl$_3$) δ=1.07 (s, 9H); 3.35–3.50(m, 4H); 5.54 (d, J=7, C$\underline{H}$NH); 7.32–7.68 (m, 15H); 8.95 (brs., 1H); 9.16 (d, J=7, NH).

(d) Benzhydryl 3-acetoxymethyl-7β-[DL-2-[3-(2-t-butyldiphenylsilyloxyethyl)-2-oxoimidazolidin-1-ylcarbonylamino]-2-phenylacetamido]-7α-methylthioceph-3-em-4-carboxylate The product from the previous step (1.09 g) was coupled with benzhydryl 7β-amino-7α-methylthiocephalosporanate (968 mg) by the procedure described in Example 50(a). Silica gel chromatography/dichloroethane-ethyl acetate gradient) gave the title compound as a pale yellow foam, (840 mg).

I.R. (KBr) 1785 cm$^{-1}$.

N.M.R. (CDCl$_3$) δ=1.05 and 1.06 (2×s, 9H); 2.02, 2.03, 2.14 and 2.27 (4×s, 6H, OCOC$\underline{H}_3$ and SC$\underline{H}_3$); 3.31–3.54 (m, 6H); 3.69–3.83 (m, 4H); 4.86 and 5.11, 4.88 and 5.12 (2×ABq, J=14, 2H); 4.91 and 4.92 (2×s, 1H); 5.60 and 5.62 (2×d, J=7, C$\underline{H}$NH); 6.88 (s, 1H); 6.92 and 6.93 (2×s, 1H); 7.25–7.68 (m, 25H); 9.19–9.23 (m, NH).

(e) Benzhydryl 3-acetoxymethyl-7β-[DL-2-[3-(2-hydroxyethyl)-2-oxoimidazolidin-1-ylcarbonylamino]-2-phenylacetamido]-7α-methylthioceph-3-em-4-carboxylate The t-butyldiphenylsilyloxyethyl derivative from the previous part (Example 76(d) (650 mg) in acetonitrile (10 ml) was treated at 0°–5° with 40% aqueous hydrofluoric acid (2 ml). The solution was stirred for 3 hours at this temperature and then for a further 3 hours at room temperature. After adding to excess saturated aqueous sodium bicarbonate, the mixture was extracted with ethyl acetate (50 ml) and the organic extract was dried and evaporated. Purification of the crude product by silica gel chromatography (ethyl acetate-isopropanol gradient) gave the title compound, (340 mg).

I.R. (KBr) 1785 cm$^{-1}$.

N.M.R. (CDCl$_3$) δ=1.98, 2.00 and 2.22 (3×s, 6H, SC$\underline{H}_3$ and OCOC$\underline{H}_3$); 2.97 (brs., 1H); 3.17–3.46 (m, 6H); 3.72–3.84 (m, 4H); 4.81 and 5.04, 4.81 and 5.05 (2×ABq, J=14, 2H); 4.86 and 4.90 (2×s, 1H); 5.80 and 5.82 (2×d, J=7, C$\underline{H}$NH); 6.86 and 6.87 (2×s, 1H); 7.22–7.50 (m, 15H); 7.64 and 7.68 (2×s, 1H); 9.28 and 9.29 (2×d, J=7, NH).

(f) 3-Acetoxymethyl-7β-[DL-2-[3-(2-hydroxyethyl)-2-oxoimidazolidin-1-ylcarbonylamino]-2-phenylacetamido]-7α-methylthioceph-3-em-4-carboxylic acid Treatment of the benzhydryl ester from the previous step (340 mg) with trifluoroacetic acd, as described in Example 57(a), gave the title compound (215 mg).

I.R. (KBr) 1780 cm$^{-1}$.

N.M.R. (DMSO-d$_6$) δ=1.88, 1.98, 2.00 and 2.18 (4×s, 6H, SC$\underline{H}_3$ and OCOC$\underline{H}_3$); 3.19–3.72 (m, 10H); 4.60 and 4.91, 4.64 and 4.97 (2×ABq, J=13, 2H); 4.76 (brs., OH); 5.03 and 5.04 (2×s, 1H); 5.59 and 5.61 (2×d, J=7, C$\underline{H}$NH); 7.24–7.41 (m, 5H); 9.02 and 9.11 (2×d, J=7, N$\underline{H}$); 9.57 and 9.60 (2×s, 1H).

(g) 3-Acetoxymethyl-7β-[DL-2-[3-(2-hydroxyethyl)-2-oxoimidazolidin-1-ylcarbonylamino]-2-phenylacetamido]-7α-hydroxyaminoceph-3-em-4-carboxylic acid The title compound (53 mg) was prepared by treatment of the 7α-methylthiocephem obtained in the previous step (210 mg) with mercuric acetate and hydroxylamine hydrochloride and triethylamine as described previously for Example 9(b).

I.R. (KBr) 1785 cm$^{-1}$.

N.M.R. (DMSO-d$_6$) δ=1.98 and 2.00 (2×s, 3H); 3.13–3.66 (m, 10H); 4.56 and 4.86, 4.60 and 4.90 (2×ABq, J=13, 2H); 5.00 and 5.06 (2×s, 1H); 5.62–5.64 (m, CHNH); 7.24–7.41 (m, 5H); 8.07–8.15 (brm., 1H); 9.05–9.10 (m, NH); 9.35 and 9.45 (2×s, 1H).

EXAMPLE 77

7β-[D-2-(4-Ethyl-2,3-dioxopiperazin-1-ylcarbonylamino)-2-phenylacetamido]-7α-hydroxyamino-3-carbamoyloxymethyl-ceph-3-em-4-carboxylic acid (a) Sodium 7β-[D-2-(4-Ethyl-2,3-dioxopiperazin-1-ylcarbonylamino)-2-phenylacetamildo]-7α-methylthio-3-hydroxymethyl-ceph-3-em-carboxylate The 3-acetoxymethyl compound of Example 6(a) (1.5 g) in water (60 ml) was treated with sodium bicarbonate (0.2 g) followed by a solution of wheat germ lipase (Sigma L 3001 [Trade Mark]; 1.0 g) in water (15 ml) and the mixture was adjusted to pH 7.0 and heated at 37° C. for 3½ hours whilst maintaining the solution at pH 7.0. The reaction mixture was cooled to 0° C., overlaid with ethylacetate:tetrahydrofuran (1:1) (100 ml), treated with 2M hydrochloric acid to pH2 then filtered through "Hyflo". The filtrate was separated and the aqueous phase was saturated with sodium chloride and re-extracted with the said solvent mixture. The organic extracts were combined, underlaid with water (50 ml) and basified with aqueous sodium bicarbonate to pH 7.0. The aqueous layer was separated and the water was removed in vacuo. The crude product was triturated with acetone (50 ml) then ether (100 ml) and filtered to give the title compound (1.03 g) as an off white powder.

I.R. (KBr) 1765 cm$^{-1}$.

N.M.R. (DMSO-d$_6$) δ=1.07 (t, J=7, 3H); 1.6 (s, 2H, H$_2$O); 2.25 (s, 3H); 2.95 and 3.25 (2H, ABq, J=17); 3.3–3.7 (m, 4H); 3.75 and 4.1 (2H, ABq, J=12); 3.8–4.0 (m, 2H); 4.78 (s, 1H); 5.65 (d, J=6, 1H); 7.2–7.5 (m, 5H); 7.58 (s, NH); 9.8 (d, J=6, NH).

(b) Sodium 7β-[D-2-(4-ethyl-2,3-dioxopiperazin-1-ylcarbonylamino)-2-phenyl acetamido]-7α-methylthio-3-carbamoyloxymethyl-ceph-3-em-4-carboxylate The product from part (a) (1.0 g) suspended in dry acetonitrile (50 ml) was cooled to 0° C. under nitrogen and treated with chlorosulphonyl isocyanate (1 ml). After 2 hours the mixture was added to 2M hydrochloric acid (100 ml) and ethyl acetate/tetrahydrofuran (150 ml) and rapidly stirred for 10 minutes at 0° C. The organic phase was separated, washed with brine (100 ml), underlaid with water (100 ml) and adjusted to pH 7 with aqueous sodium bicarbonate. This aqueous phase was freeze dried and afforded 1.86 g of a white powder being the crude title compound.

I.R. (KBr) 1770 cm$^{-1}$.

N.M.R. (DMSO-d$_6$) δ=1.06 (t, J=7, 3H); 1.63 (s, 2H, H$_2$O); 2.25 (s, 3H); 2.95 and 3.18 (2H, ABq, J=17); 3.2–3.7 (m, 4H and HOD); 3.85 (m, 2H); 4.65 (m, 2H); 4.85 (s, 1H); 5.65 (d, J=6, 1H); 6.3–6.8 (brs, NH$_2$); 7.2–7.5 (m, 5H); 9.6 (brs., NH); 9.8 (d, J=6, NH).

(c) 7β-[D-2-(4-Ethyl-2,3-dioxopiperazin-1-ylcarbonylamino)-2-phenylacetamido]-7α-t-butyldiphenylsilyloxyamino-3-carbamoyloxymethyl-ceph-3-em-4-carboxylic acid The crude product from part (b) (1.86 g) was slurried with dimethylformamide (20 ml) and filtered. The filtrate was cooled to −50° C. under nitrogen and treated sequentially with a solution of mercuric acetate (0.61 g) in dimethylformamide (2 ml) then a solution of O-(t-butyldiphenylsilyl)hydroxylamine (0.52 g) in dimethylformamide (2 ml). The mixture was warmed to 20° C. over 30 minutes and added to ethyl acetate:tetrahydrofuran (1:1, 200 ml). This solution was washed with 2M hydrochloric acid (4×100 ml), brine (100 ml), dried (Na$_2$SO$_4$); and evaporated in vacuo. The crude product was purified by chromatography (silica gel, acetone/2% acetic acid) to afford 160 mg of the title compound.

I.R. (KBr) 1780 cm$^{-1}$.

N.M.R. (DMSO-d$_6$) δ=0.97 (s, 9H); 1.04 (t, J=7, 3H); 3.05 and 3.3 (2H, ABq, J=17); 3.2–3.45 (m, 2H); 3.5 (m, 2H); 3.85 (m, 2H); 4.56 and 4.75 (2H, ABq, J=13); 4.99 (s, 1H); 5.69–5.74 (m, 1H); 6.4–6.8 (brs, NH$_2$); 7.25–7.55 (m, 11H); 7.67 (d, J=6, 4H); 9.81–9.86 (m, NH).

(d) 7β-[D-2-(4-Ethyl-2,3-dioxopiperazin-1-ylcarbonylamino)-2-phenylacetamido]-7α-hydroxyamino-3-carbamoyloxymethyl-ceph-3-em-4-carboxylic acid The product from part (c) (160 mg) in acetonitrile (1.51 ml) and tetrahydrofuran (1.5 ml) was cooled to 0° C. and treated with aqueous hydrofluoric acid (40%) (0.5 ml). After 45 minutes the solvent was removed in vacuo and toluene (3 ml) and methanol (2 ml) were added. The resultant solution was evaporated in vacuo and the residue was dissolved in methanol (2 ml), filtered and diethyl ether (50 ml) was added dropwise to the filtrate with rapid stirring. The precipitate was filtered off, washed with diethyl ether (25 ml) and dried in vacuo to afford the title compound, (104 mg).

I.R. (KBr) 1780 cm$^{-1}$.

N.M.R. (DMSO-d$_6$) δ=1.05 (t, J=7, 3H); 3.10 and 3.42 (2H, ABq, J=17.5); 3.36 (q, J=6, 2H); 3.52 (m, 2H); 3.86 (m, 2H); 4.50 and 4.73 (2H, ABq, J=12.5); 5.01 (s, 1H); 5.65 (d, J=7.5, 1H); 6.4–6.8 (brs, NH$_2$); 7.2–7.5 (m, 5H); 9.51 (s, NH); 9.85 (d, J=7.5, NH).

EXAMPLE 78

(Alternative route to Example 2)

7β-[D-2-(4-Ethyl-2,3-dioxopiperazin-1-ylcarbonylamino-2-phenylacetamido]-7α-hydroxyaminocephalosporanic acid (a) Benzhydryl 7β-[(3,5-Di-t-butyl-4-hydroxyphenyl)-methyleneamino]cephalosporanate Benzhydryl 7β-aminocephalosporanate (4.38 g) and 3,5-di-t-butyl-4-hydroxybenzaldehyde (2.34 g) were dissolved in tetrahydrofuran (25 ml) and the solution evaporated to dryness in vacuo after 10 minutes. The residue was dissolved in 1:1 dichloromethane-carbon tetrachloride (50 ml) and re-evaporated. The process was repeated to give the title compound as a yellow-brown foam (6.54 g).

I.R. (KBr) 1775 cm$^{-1}$.

N.M.R. (CDCl$_3$) δ=1.46 (s, 18H); 2.02 (s, 3H); 3.36 and 3.56 (ABq, J=18, 2H); 4.75 and 5.00 (ABq, J=13, 2H); 5.16 (d, J=5, 1H); 5.45 (d, J=5, 1H); 5.56 (s, OH); 6.97 (s, 1H); 7.29–7.73 (m, 12H); 8.54 (s, 1H).

(b) Benzhydryl 7-[(3,5-di-t-butyl-4-oxo-2,5-cyclohexadien-1-ylidene)methylimino]cephalosporanic acid A solution of the imine from the previous stage (78a) (6.54 g) in dichloromethane (100 ml) containing anhydrous magnesium sulphate (9.6 g) was treated with nickel peroxide (6.6 g) and the suspension was stirred vigorously at room temperature for 1 hour. Filtration followed by evaporation of the solvent in vacuo gave the title compound as a dark red foam, (6.23 g).

I.R. (KBr) 1775 cm$^{-1}$.

N.M.R. (CDCl₃) δ=1.32 (s, 9H); 1.34 (s, 9H); 2.04 (s, 3H); 3.46 and 3.65 (ABq, J=18, 2H); 4.79 and 5.03 (ABq, J=13, 2H); 5.40 (brs., 1H); 7.00 (s, 1H); 7.02 (s, 1H); 7.30–7.50 (m, 10H); 7.90 (s, 1H); 8.03 (brs., 1H).

(c) Benzhydryl 7β-amino-7α-(t-butyldiphenylsilyloxyamino)cephalosporanate

The product from the previous stage (78b) (2.53 g) in dichloromethane (15 ml) was treated with O-t-butyldiphenylsilylhydroxylamine (1.16 g) and the solution was stirred at 25° for 18 hours. After evaporation of the solvent in vacuo the residue was dissolved in methanol (25 ml), treated with Girard-T reagent (2-hydrazino-N,N,N-trimethyl-2-oxoethanaminiumchloride) (975 mg) and kept at 0° for 18 hours. Evaporation of the solvent gave a red foam which was dissolved in ethyl acetate (25 ml) and water (25 ml). The aqueous layer was re-extracted with ethyl acetate (25 ml) and the combined organic extracts were dried and evaporated to give the crude product. Silica gel chromatography (dichloromethane-ethyl acetate) gradient gave the title compound as a pale yellow foam, (515 mg).

I.R. (KBr) 1780 cm⁻¹.

N.M.R. (CDCl₃) δ=1.05 (s, 9H); 2.00 (brs., 5H, OCOCH₃ and NH₂; 3.24 (s, 2H); 4.47 (s, 1H); 4.73 and 4.90 (ABq, J=13, 2H); 5.53 (s, 1H); 6.95 (s, 1H); 7.26–7.69 (m, 20H).

(d) Benzhydryl 7α-(t-butyldiphenylsilyloxyamino)-7β-[D-2-(4-ethyl-2,3-dioxopiperazin-1-ylcarbonylamino)-2-phenylacetamido]cephalosporanate The title compound (415 mg) was prepared by the reaction of the 7β-aminocephem from the previous stage (78(c)) (500 mg) with D-2-(4-ethyl-2,3-dioxopiperazin-1-ylcarbonylamino)-2-phenylacetic acid (250 mg) by the method described for Example (45a).

I.R. (KBr) 1790 cm⁻¹.

N.M.R. (CDCl₃) δ=0.95 (s, 9H); 1.12 (t, J=7, 3H); 1.96 (s, 3H); 3.04 and 3.12 (ABq, J=17, 2H); 3.32–3.50 (m, 4H, CH₂CH₃ and piperazine CH₂); 3.85–4.06 (m, 2H); 4.35 (s, 1H); 4.80 and 4.97 (ABq, J=14, 2H); 5.44 (d, J=7, CHNH); 6.53 (s, 1H); 6.84 (s, 1H); 6.85 (s, 1H); 7.12–7.62 (m, 25H); 9.89 (d, J=7, NH).

(e) 7α-(t-Butyldiphenylsilyloxyamino)-7β-[D-2-(4-ethyl-2,3-dioxopiperazin-1-ylcarbonylamino)-2-phenylacetamido]cephalosporanic acid The product from the previous step (Example 78(d)) (200 mg) was treated with trifluoroacetic acid-anisole by the method described in Example 57(a) to give the title compound (95 mg).

I.R. (KBr) 1785 cm⁻¹.

N.M.R. (DMSO-d₆) δ=0.96 (s, 9H); 1.06 (t, J=7, 3H); 1.96 (s, 3H); 3.09–3.38 (m, 4H); 3.45–3.51 (m, 2H); 3.82–3.86 (m, 2H); 4.60 and 4.88 (ABq, J=13, 2H); 4.99 (s, 1H); 5.69 (d, J=7, CHNH); 7.01 (s, 1H); 7.25–7.66 (m, 15H); 9.81 (d, J=7, NH); 9.86 (s, 1H).

(f) [D-2-(4-Ethyl-2,3-dioxopiperazin-ylcarbonylamino)-2-phenylacetamido]-7α-hydroxyaminocephalosporanic acid The title compound (54 mg) was prepared by treatment of the 7-t-butyldiphenylsilyloxyaminocephem from the previous step (78(e)) (90 mg) with 40% aqueos hydrofluoric acid as described for Example 69(f).

I.R. (KBr) 1780 cm⁻¹.

N.M.R. (DMSO-d₆) δ=1.09 (t, J=7, 3H); 2.04 (s, 3H); 3.16–3.56 (m, 6H); 3.89–3.93 (m, 2H); 4.60 and 4.91 (ABq, J=13, 2H); 5.06 (s, 1H); 5.69 (d, J=7, CHNH); 6.50 (brs., 1H); 7.30–7.49 (m, 5H); 8.21 (brs., 1H); 9.89 (d, J=7, NH).

We claim:

1. A cephalosporin having the formula wherein

Q is hydrogen or a radical forming an in vivo hydrolyzable ester;

R is phenyl, hydroxyphenyl, dihydroxyphenyl, benzyloxycarbonyloxyphenyl, 2-thienyl or 3-thienyl; and the amide side chain is in the D- or the DL-stereochemical form; or R is CH₃—CH(OH)—, CH₃—CH(OSO₃H)— or CH₃—CH(OCH₃)—; and the amide side chain is in the 2R,3S stereochemical form;

R¹ is —CONH₂, and

R¹⁰ is hydrogen, C₁–C₈ alkyl, phenyl, benzyl or —SO₂(C₁–C₄ alkyl);

R² is —CH₂OCOCH₃, —CH₂N₃, —CH₂S-Het, n is 3 or 4; and

Het is a heterocyclic group which is a triazolyl, tetrazolyl, thiazolyl, isothiazolyl, oxazolyl, oxadiazolyl, triazinyl, oxodihydrotriazinyl, dioxotetrahydrotriazinyl, thiadiazolyl, benzoxazolyl, benzothiazolyl or tetrazolopyridazinyl group; one of said heterocyclic groups monosubstituted by C₁–C₄ alkoxy, halo or a group of the formula —(CH₂)ₚR¹⁶ where p is 0, 1, 2 or 3 and R¹⁶ is —COOH, —OSO₂OH, —SO₂OH or —OH, with the proviso that p is other than zero when Het is tetrazolyl; or one of said monosubstituted heterocyclic groups further substituted by a methyl group; said heterocyclic groups attached to the adjacent S atom by a carbon atom of the heterocyclic ring;

or a pharmaceutically acceptable cationic salt thereof when Q is hydrogen or the group R¹ contains a further acidic functionality.

2. A compound of claim 1 wherein Q is a radical forming an in vivo hydrolyzable ester which is —CH₂OCO(t-butyl), —CH₂OCOCH₃, —CH(CH₃)OCOCH₃, —CH(CH₃)OCOOEt,

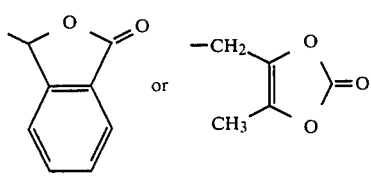

3. A compound of claim 1 wherein Q is hydrogen.

4. A compound of claim 2 wherein when R² is —CH₂S—Het, Het is 1-[(C₁-C₄ alkyl), carboxymethyl, sulfomethyl, (2-sulfoxyethyl), hydroxymethyl or (2-hydroxyethyl)]tetrazol-5-yl, thiazol-2-yl, 5-(carboxymethyl)-4-methylthiazol-2-yl, 2,5-dihydro-6-hydroxy-2-methyl-5-oxo-1,2,4-triazin-3-yl, 5,6-dioxo-4-methyl-1,4,5,6-tetrahydro-1,2,4-triazin-3-yl, 1,2,3-thiadiazol-5-yl, 1,3,4-thiadiazol-2-yl, 5-[methyl or (2-hydroxyethyl)]-1,3,4-thiadiazol-2-yl, 3-methyl-1,2,5-thiadiazol-5-yl, benzoxazol-2-yl, benzothiazol-2-yl, or (5-chloro, 6-hydroxy, or 6-ethoxy)benzothiazol-2-yl.

5. A compound of claim 3 wherein when R² is —CH₂S—Het, Het is 1-[(C₁-C₄ alkyl), carboxymethyl, sulfomethyl, (2-sulfoxyethyl), hydroxymethyl or (2-hydroxyethyl)]tetrazol-5-yl, thiazol-2-yl, 5-(carboxymethyl)-4-methylthiazol-2-yl, 2,5-dihydro-6-hydroxy-2-methyl-5-oxo-1,2,4-triazin-3-yl, 5,6-dioxo-4-methyl-1,4,5,6-tetrahydro-1,2,4-triazin-3-yl, 1,2,3-thiadiazol-5-yl, 1,3,4-thiadiazol-2-yl, 5-[methyl or (2-hydroxyethyl)]-13,4-thiadiazol-2-yl, 3-methyl-1,2,5-thiadiazol-5-yl, benzoxazol-2-yl, benzothiazol-2-yl, or (5-chloro, 6-hydroxy, or 6-ethoxy)benzothiazol-2-yl.

6. A compound as claimed in claim 2 wherein R is phenyl, 4-hydroxyphenyl, 4-benzyloxycarbonyloxyphenyl, 3,4-dihydroxyphenyl, 2-thienyl, 3-thienyl, CH₃CH(OH)—, CH₃CH(OCH₃)— or CH₃CH(OSO₂OH).

7. A compound as claimed in claim 3 wherein R is phenyl, 4-hydroxyphenyl, 4-benzyloxycarbonyloxyphenyl, 3,4-dihydroxyphenyl, 2-thienyl, 3-thienyl. CH₃CH(OH)—, CH₃CH(OCH₃)— or CH₃CH(OSO₂OH)—.

8. A compound as claimed in claim 5 wherein R is phenyl, 4-hydroxyphenyl, 4-benzyloxycarbonyloxyphenyl, 3,4-dihydroxyphenyl, 2-thienyl, 3-thienyl, CH₃CH(OH)—, CH₃CH(OCH₃) or CH₃CH(OSO₂OH)—.

9. A compound of claim 8 wherein R is phenyl and the amide side chain is in the D-form or R is CH₃CHOH—; R¹ is

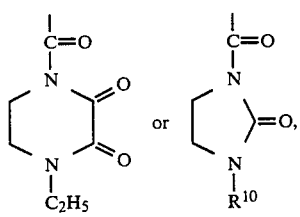

R¹⁰ is hydrogen, ethyl or methanesulfonyl; and R² is

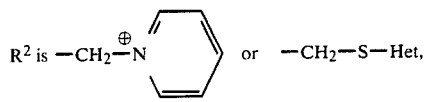

and Het is 1-[carboxymethyl, sulfomethyl, or (2-hydroxyethyl)]tetrazol-5-yl, 2,5-dihydro-6-hydroxy-2-methyl-5-oxo-1,2,4-triazin-3-yl or 5,6-dioxo-4-methyl-1,4,5,6-tetrahydro-1,2,4-triazin-3-yl.

10. The compound of claim 9 wherein R is CH₃CH(OH)—, R¹ is

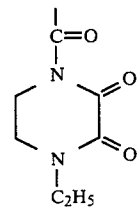

and R² is 1-(carboxymethyl)tetrazol-5-yl.

11. The compound of claim 9 wherein R is CH₃CH(OH)—, R¹ is

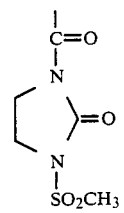

and R² is 1-(carboxymethyl)tetrazol-5-yl.

12. The compound of claim 9 wherein R is phenyl, R¹ is

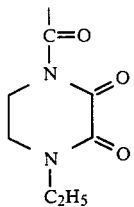

and R² is

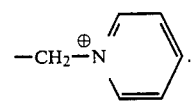

13. A pharmaceutical composition comprising an antibacterially effective amount of a compound of claim 1 and a pharmaceutically acceptable diluent or carrier suitable for parenteral administration in the treatment of bacterial infection in man.

14. A method of treating a bacterial infection in man which comprises parenteral administration of an antibacterially effective amount of a compound of claim 1.

15. A cephalosporin ester having the formula

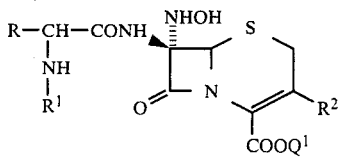

wherein $Q^1$ is t-butyl, benzhydryl, benzyl, p-methoxybenzyl or p-nitrobenzyl;

R is phenyl, hydroxyphenyl, dihydroxyphenyl, benzyloxycarbonyloxyphenyl, 2-thienyl or 3-thienyl; and the amide side chain is in the D- or the DL- stereochemical form; or R is $CH_3—CH(OH)—$, $CH_3—CH(OSO_3H)—$ or $CH_3—CH(OCH_3)—$; and the amide side chain is in the 2R,3S stereochemical form;

$R^1$ is $—CONH_2$,

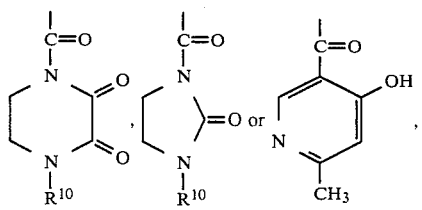

and $R^{10}$ is $C_1–C_8$ alkyl, phenyl, benzyl or $—SO_2(-C_1–C_4$ alkyl);

$R^2$ is $—CH_2OCOCH_3$, $—CH_2N_3$, $—CH_2S—Het$,

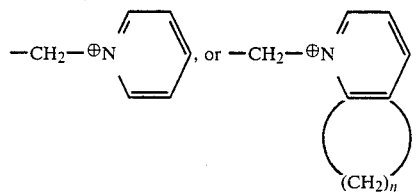

n is 3 or 4; and

Het is a heterocyclic group which is a triazolyl, tetrazolyl, thiazolyl, isothiazolyl, oxazolyl, oxadiazolyl, triazinyl, oxodihydrotriazinyl, dioxotetrahydrotriazinyl, thiadiazolyl, benzoxazolyl, benzothiazolyl or tetrazolopyridazinyl group; one of said heterocyclic groups monosubstituted by $C_1–C_4$ alkoxy, halo or a group of the formula $—(CH_2)_pR^{16}$ where p is 0, 1, 2 or 3 and $R^{16}$ is $—COOH$, $—OSO_2OH$, $—SO_2OH$ or $—OH$, with the proviso that p is other than zero when Het is tetrazolyl; or one of said monosubstituted heterocyclic groups further substituted by a methyl group; said heterocyclic groups attached to the adjacent S atom by a carbon atom of the heterocyclic ring.

16. A compound of claim 15 wherein $Q^1$ is t-butyl or benzhydryl.

17. A compound of claim 16 wherein $Q^1$ is t-butyl, R is phenyl or 2-thienyl, $R^1$ is

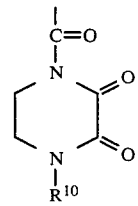

and $R^2$ is $—CH_2OCOCH_3$ or 1,2,3-thiadiazol-5-yl.

18. A compound of claim 16 wherein $Q^1$ is benzhydryl; R is phenyl, 3-thienyl, 4-hydroxyphenyl, 3,4-dihydroxyphenyl and the amide side chain is in the D-form, or R is $CH_3CH(OH)—$; $R^1$ is $—CONH_2$,

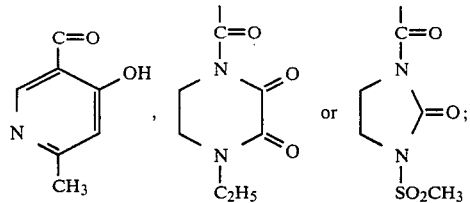

and $R^2$ is $—CH_2OCOCH_3$.

19. A compound of the formula

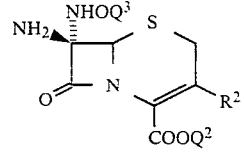

where $R^2$ is as defined in claim 1 and $Q^2$ is hydrogen or a radical forming an in vivo hydrolyzable ester, or a conventional carboxy protecting group and $Q^3$ hydrogen or a conventional hydroxy protecting group.

20. The compound of claim 19 wherein $Q^2$ and $Q^3$ are each hydrogen.

* * * * *